(12) United States Patent
Mack et al.

(10) Patent No.: US 8,974,814 B2
(45) Date of Patent: Mar. 10, 2015

(54) LAYERED DRUG DELIVERY POLYMER MONOFILAMENT FIBERS

(75) Inventors: Brendan C. Mack, Alhambra, CA (US);
Mark E. Davis, Pasadena, CA (US);
Kenneth W. Wright, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 865 days.

(21) Appl. No.: 12/269,838

(22) Filed: Nov. 12, 2008

(65) Prior Publication Data

US 2009/0155326 A1    Jun. 18, 2009

Related U.S. Application Data

(60) Provisional application No. 61/002,874, filed on Nov. 12, 2007, provisional application No. 61/124,173, filed on Apr. 15, 2008.

(51) Int. Cl.
| | |
|---|---|
| *A61K 9/70* | (2006.01) |
| *A01N 25/34* | (2006.01) |
| *A61K 31/155* | (2006.01) |
| *A61K 9/00* | (2006.01) |
| *A61K 31/4164* | (2006.01) |
| *A61K 31/496* | (2006.01) |
| *A61K 31/505* | (2006.01) |
| *A61K 31/5365* | (2006.01) |
| *A61K 31/56* | (2006.01) |
| *A61K 31/65* | (2006.01) |
| *A61K 31/7008* | (2006.01) |
| *A61K 31/7052* | (2006.01) |
| *A61K 38/00* | (2006.01) |

(52) U.S. Cl.
CPC ............ *A61K 31/155* (2013.01); *A61K 9/0051* (2013.01); *A61K 9/70* (2013.01); *A61K 31/4164* (2013.01); *A61K 31/496* (2013.01); *A61K 31/505* (2013.01); *A61K 31/5365* (2013.01); *A61K 31/56* (2013.01); *A61K 31/65* (2013.01); *A61K 31/7008* (2013.01); *A61K 31/7052* (2013.01); *A61K 38/00* (2013.01)
USPC ............ 424/443; 424/484; 424/402; 424/409

(58) Field of Classification Search
None
See application file for complete search history.

(56) References Cited

U.S. PATENT DOCUMENTS

| | | | |
|---|---|---|---|
| 3,833,002 A | 9/1974 | Palma | |
| 4,116,955 A | 9/1978 | Ichikawa et al. | |
| 4,170,601 A | 10/1979 | Leadbetter | |
| 4,190,720 A | 2/1980 | Shalaby | |
| 4,367,072 A | 1/1983 | Vogtle et al. | |
| 4,582,052 A | 4/1986 | Dunn et al. | |
| 4,605,730 A | 8/1986 | Shalaby et al. | |
| 4,624,256 A | 11/1986 | Messier et al. | |
| 4,700,704 A | 10/1987 | Jamiolkowski et al. | |
| 4,705,820 A | 11/1987 | Wang et al. | |
| 4,711,241 A | 12/1987 | Lehmann | |
| 4,776,984 A | 10/1988 | Traitler et al. | |
| 4,788,979 A | 12/1988 | Jarrett et al. | |
| 6,432,438 B1 * | 8/2002 | Shukla ........................ 424/426 |
| 2003/0008818 A1 | 1/2003 | Pun et al. | |
| 2003/0017972 A1 | 1/2003 | Pun et al. | |
| 2005/0019568 A1 * | 1/2005 | Foss et al. ..................... 428/373 |
| 2005/0276841 A1 * | 12/2005 | Davis et al. ................... 424/443 |

OTHER PUBLICATIONS

Zhou (Development of a multiple-drug delivery implant for intraocular management of proliferative vitreoretinopathy, 55 J. Controlled Release 281 (1998), on p. 5 of IDS dated Aug. 17, 2009).*
Aderriotis et al., "Outcomes of Irradiated Polyglactin 910 Vicryl Raptide Fast-Absorbing Suture in Oral and Scalp Wounds", Journal of the Canadian Dental Association, Jun. 1999, vol. 65, No. 6, pp. 345-347.
Albers et al., "Cyclodextrin Derivatives in Pharmaceutics", Critical Reviews in Therapeutic Drug Carrier Systems, 1995, vol. 12, No. 4, pp. 311-337.
Alexis, "Factors affecting the degradation and drug-release mechanism of poly(lactic acid) and poly[(lactic acid)-co-(glycolic acid)]", Polymer International, 2005, vol. 54, pp. 36-46.
Alvarez-Lorenzo et al., "Soft Contact Lenses Capable of Sustained Delivery of Timolol", Journal of Pharmaceutical Sciences, Oct. 2002, vol. 91, No. 10, pp. 2182-2192.
Baltch et al., "Inhibitory and Bactericidal Activities of Levofloxacin, Ofloxacin, Erythromycin, and Rifampin Used Singly and in Combination Against Legionella Pneumophila", Antimicrobial Agents and Chemotherapy, Aug. 1995, vol. 39, No. 8, pp. 1661-1666.
Batycky et al., "A Theoretical Model of Erosion and Macromolecular Drug Release from Biodegrading Microspheres", Journal of Pharmaceutical Services, Dec. 1997, vol. 86, No. 12, pp. 1464-1477.
Boussif et al., "A versatile vector for gene and oligonucleotide transfer into cells in culture and in vivo: Polyethylenimine", Proc. Natl. Acad. Sci. USA, Aug. 1995, vol. 92, pp. 7297-7301.

(Continued)

*Primary Examiner* — H. Sarah Park
(74) *Attorney, Agent, or Firm* — KPPB LLP

(57) ABSTRACT

The present invention is directed generally to a layered polymeric monofilament fiber drug delivery device, where each layer of the device can contain a different polymer, drug, additive, or any combination or mixture thereof. The layered nature of the current monofilament polymeric monofilament device provides the capability to modulate the release of one or more drugs and/or the mechanical properties of the fiber so that drug release and device failure can be separately tuned to provide for the tailored introduction of therapeutically effective drugs or agents to a target tissue. Moreover, the fiber may comprise more than one distinct segments along its length, each segment itself having different combinations and/or numbers of layers thereby providing even greater freedom in the design of the therapeutic delivery device. The invention is also directed to a method of manufacturing such a layered polymeric monofilament fiber drug delivery device, and methods of treatment using such devices.

43 Claims, 42 Drawing Sheets

(56) References Cited

OTHER PUBLICATIONS

Ceulemans et al, "Evaluation of a mucoadhesive tablet for ocular use", Journal of Controlled Release, 2001, vol. 77, pp. 333-344.

Chiang et al., "In Vitro and In Vivo evaluation of an Ocular Delivery System of 5-Fluorouracil Microspheres", Journal of Ocular Pharmacology and Therapeutics, 2001, vol. 17, No. 6, pp. 545-554.

Cleland et al., "Recombinant human growth hormone poly(lactic-co-glycolic acid) (PLGA) microspheres provide a long lasting effect", Journal of Controlled Release, 1997, vol. 49, pp. 193-205.

Crow et al., "Evaluation of in Vitro Drug Release, pH Change, and Molecular Weight Degradation of Poly(L-lactic acid) and Poly(D,L-lactide-co-glycolide) Fibers", Tissue Engineering, 2005, vol. 11, No. 7/8, pp. 1077-1084.

Crow et al., "Release of Bovine Serum Albumin from a Hydrogel-Cored Biodegradable Polymer Fiber", Biopolymers, 2006, vol. 81, pp. 419-427.

Davis et al., "Levofloxacin—A Review of its Antibacterial Activity, Pharmacokinetics and Therapeutic Efficacy", Drugs, 1994, vol. 47, No. 4, pp. 677-700.

Freiberg et al., "Polymer microspheres for controlled drug release", International Journal of Pharmaceutics, 2004, vol. 282, pp. 1-18.

Fridrikh et al., "Controlling the Fiber Diameter During Electrospinning", Physical Review Letters, Apr. 11, 2003, vol. 90, No. 14, pp. 144502-144502-4.

Fujimoto et al., "Effect of Levofloxacin-Albumin Dacron Graft on Graft Infection", Jpn. J. Pharmacol. 1995, vol. 69, pp. 443-445.

Gao et al., "The implantable 5-fouorouracil-loaded poly(L-lactic acid) fibers prepared by wet-spinning from suspension", Journal of Controlled Release, 2007, vol. 118, pp. 325-332.

Giordano et al., "Sustained Delivery of Retinoic Acid from Microspheres of Biodegradable Polymer in PVR", Investigative Ophthalmology & Visual Science, Aug. 1993, vol. 34, No. 9, pp. 2743-2751.

Gonzalez et al., "New Class of Polymers for the Delivery of Macromolecular Therapeutics", Bioconjugate Chem., 1999, vol. 10, pp. 1068-1074.

Hiratani et al., "Timolol uptake and release by imprinted soft contact lenses made of N,N-diethylacrylamide and methacrylic acid", Journal of Controlled Release, 2002, vol. 83, pp. 223-230.

Holland et al., "Special Considerations in the Evaluation and Management of Uveitis in Children", Am. J. Ophthalmol, 2003, vol. 135, pp. 867-878.

Hwang et al, "Effects of Structure of beta-Cyclodextrin-Containing Polymers on Gene Delivery", Bioconjugate Chem., 2001, vol. 12, pp. 280-290.

Jampel et al., "Patient Preferences for Eye Drop Characteristics", Arch Ophthalmol., Apr. 20203, vol. 121, pp. 540-546.

Jones, "Effects of biomaterial-induced inflammation on fibrosis and rejection", Seminars in Immunology, 2008, vol. 20, pp. 130-136.

Kato et al., "Feasibility of Drug Delivery to the Posterior Pole of the Rabbit Eye with an Episcleral Implant", Investigative Ophthalmology & Visual Science, Jan. 2004, vol. 45, No. 1, pp. 238-244.

Kaur et al., "Penetration Enhancers and Ocular Bioadhesives: Two New Avenues for Ophthalmic Drug Delivery", Drug Development and Industrial Pharmacy, 2002, vol. 28, No. 4, pp. 353-369.

Kenawy et al., "Release of tetracycline hydrochloride from electrospun poly(ethylene-co-vinylacetate), poly(lactic acid), and a blend", Journal of Controlled Release, 2002, vol. 81, pp. 57-64.

Kenley et al., "Poly(lactide-co-glycolide) Decomposition Kinetics in Vivo and in Vitro", Macromolecules, 1987, vol. 20, pp. 2398-2403.

Kim et al., "Incorporation and controlled release of a hydrophilic antibiotic using poly(lactide-co-glycolide)-based electrospun nanofibrous scaffolds", Journal of Controlled Release, 2004, vol. 98, pp. 47-56.

Langer, "Biomaterials and Biomedical Engineering", Chemical Engineering Science, 1995, vol. 50, No. 24, pp. 4109-4121.

LeBourlais et al., "Ophthalmic Drug Delivery Systems—Recent Advances", Progress in Retinal and Eye Research, 1998, vol. 17, No. 1, pp. 33-58.

Nelson et al., "Technique Paper for Wet-Spinning Poly(L-lactic acid) and Poly(DL-lactide-co-glycolide) Monofilament Fibers", Tissue Engineering, 2003, vol. 9, No. 6, pp. 1323-1330.

Pijls et al., "Capacity and tolerance of a new device for ocular drug delivery", International Journal of Pharmaceutics, 2007, vol. 341, pp. 152-161.

Robert et al., "Comparative Review of Topical Ophthalmic Antibacterial Preparations", Drugs, 2001, vol. 61, No. 2, pp. 175-185.

Rosner et al., "Rational Design of Contact Guiding, Neurotrophic Matrices for Peripheral Nerve Regeneration", Annals of Biomedical Engineering, 2003, vol. 31, pp. 1383-1401.

Saishin et al., "Periocular Injection of Microspheres Containing PKC412 Inhibits Choroidal Neovascularization in a Porcine Model", Investigative Ophthalmology & Visual Science, Nov. 2003, vol. 44, No. 11, pp. 4989-4993.

Siepmann et al., "Mathematical modeling of bioerodible, polymeric drug delivery systems", Advanced Drug Delivery Reviews, 2001, vol. 48, pp. 229-247.

Sihvola et al., "Practical Problems in the Use of Ocusert-Pilocarpine Delivery System", ACTA Ophthalmologica, 1980, vol. 58, pp. 933-937.

Subbiah et al., "Electrospinning of Nanofibers", Journal of Applied Polymer Science, 2005, vol. 96, pp. 557-569.

Tan et al., "Randomized Clinical Trial of a New Desamethasone Delivery System (Surodex) for Treatment of Post-Cataract Surgery Inflammation", Ophthalmology, 1999, vol. 106, pp. 223-231.

Tenjarla et al., "Preparation, Characterization, and Evaluation of Miconazole-Cyclodextrin Complexes for Improved Oral and Topical Delivery", Journal of Pharmaceutical Sciences, Apr. 1998, vol. 87, No. 4, pp. 42-429.

Theng et al., "Pharmacokinetic and Toxicity Study of an Intraocular Cyclosporine DDS in the Anterior Segment of Rabbit Eyes", Investigative Ophthalmology & Visual Science, Nov. 2003, vol. 44, No. 11, pp. 4895-4899.

van de Witte et al., "Formation of porous membranes for drug delivery systems", Journal of Controlled Release, 1993, vol. 24, pp. 61-78.

Verreck et al., "Preparation and physicochemical characterization of biodegradable nerve guides containing the nerve growth agent sabeluzole", Biomaterials, 2005, vol. 26, pp. 1307-1315.

Wang et al., "Controlled release of ethacrynic acid from poly(lactide-co-glycolide) films for glaucoma treatment", Biomaterials, 2004, vol. 25, pp. 4279-4285.

Weyenberg et al., "Characterization and in vivo evaluation of ocular bioadhesive minitablets compressed at different forces", Journal of Controlled Release, 2003, vol. 89, pp. 329-340.

Weyenberg et al., "Ocular Bioerodible Minitablets as Strategy for the Management of Microbial Keratitis", Investigative Ophthalmology & Visual Science, Sep. 2004, vol. 45, No. 9, pp. 3229-3233.

Winfield et al., "A study of the causes of non-compliance by patients prescribed eyedrops", British Journal of Ophthalmology, 1990, vol. 74, pp. 477-480.

Yue et al., "A novel polymeric chlorhexidine delivery device for the treatment of periodontal disease", Biomaterials, 2004, vol. 25, pp. 3743-3750.

Zanta et al., "In Vitro Gene Delivery to Hepatocytes with Galactosylated Polyethylenimine", Bioconjugate Chem, 1997, vol. 8, pp. 539-844.

Zeng et al., "Influence of the drug compatibility with polymer solution on the release kinetics of electrospun fiber formulation", Journal of Controlled Release, 2005, vol. 105, pp. 43-51.

Zhou et al., "Development of a multiple-drug delivery implant for intraocular management of proliferative vitreoretinopathy", Journal of Controlled Release, 1998, vol. 55, pp. 281-295.

Zilberman et al., "Mechanical Properties and In Vitro Degradation of Bioresorbable Fibers and Expandable Fiber-Based Stents", Interscience, Jun. 30, 2005, pp. 792-799.

Zughui et al., "Thermodynamics of Propylparaben/beta-Cyclodextrin Inclusion Complexes", Pharmaceutical Development and Technology, 1998, vol. 3, No. 1, pp. 43-53.

\* cited by examiner

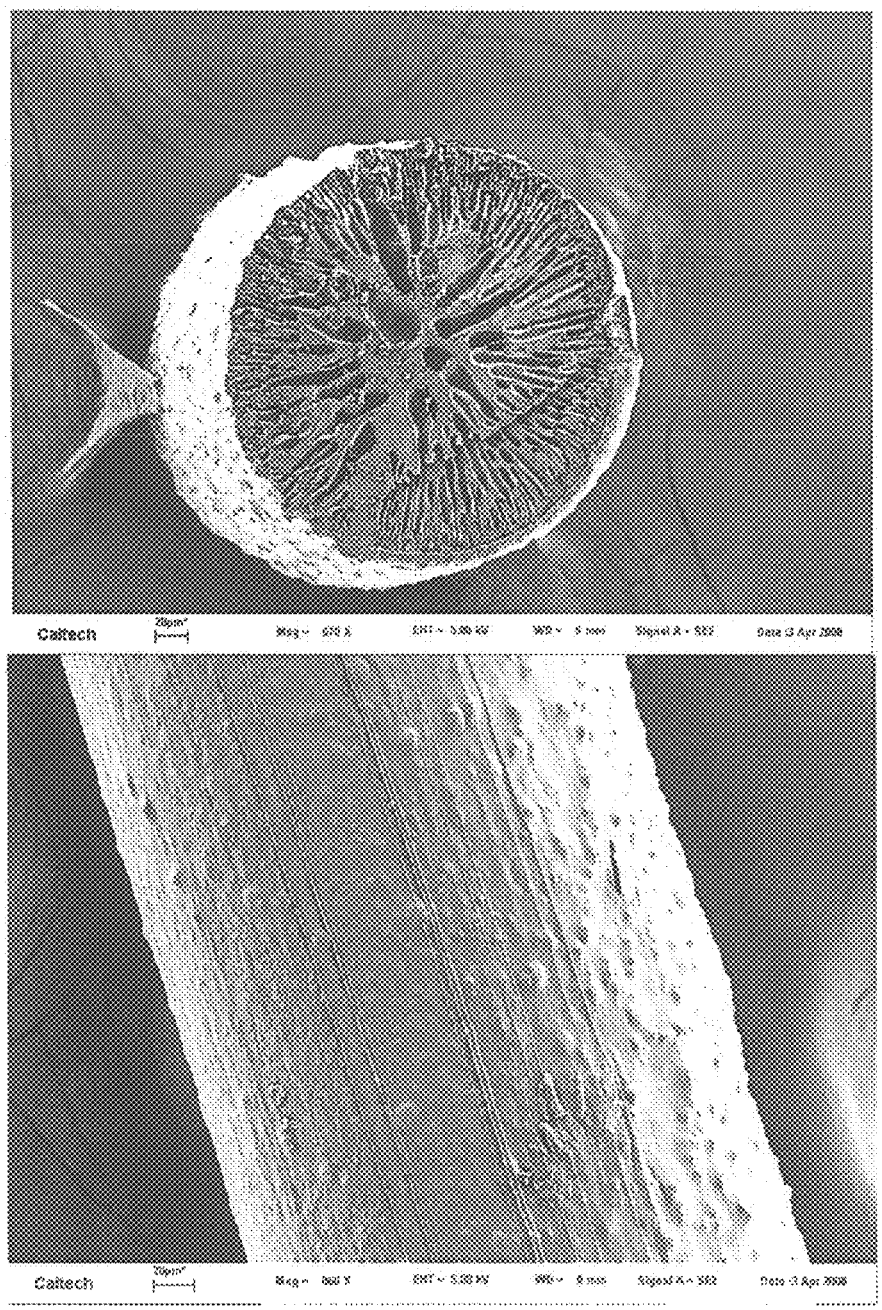

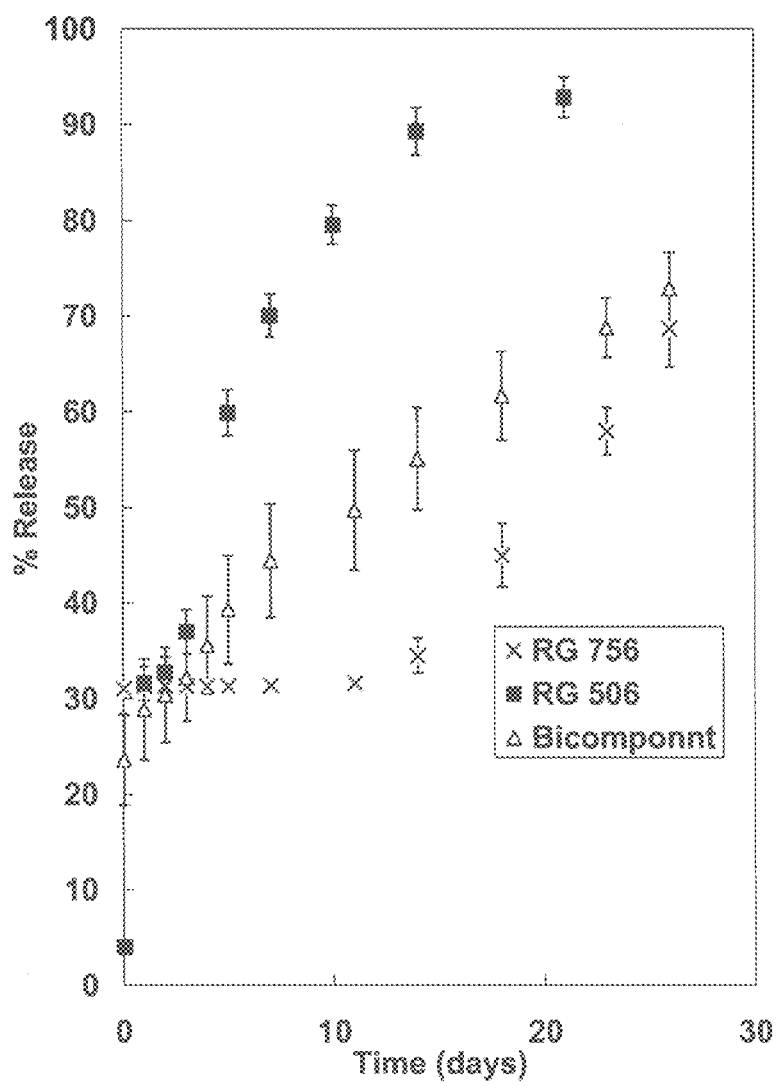

FIG. 24
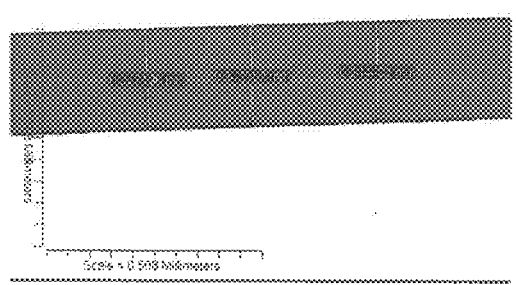
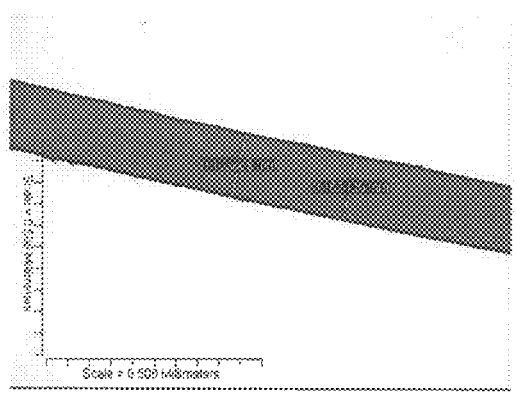
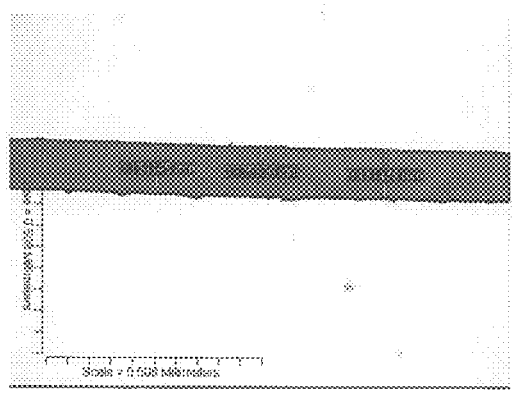

FIG. 28

Table 4. Formulation Summary

| Sample | Polymer | Drug Type | Solution Composition (%wt) | | | Coagulation Time | Temperature (°C) |
|---|---|---|---|---|---|---|---|
| | | | Polymer | DMSO | Drug | | |
| 506-L1 | RG 506 | Levofloxacin | 23.3 | 69.8 | 7.0 | 45 | 25 |
| 506-L2 | RG 506 | Levofloxacin | 22.2 | 66.7 | 11.1 | 45 | 25 |
| 506-L3 | RG 506 | Levofloxacin | 23.3 | 69.8 | 7.0 | 45 | 60 |
| 506-L4 | RG 506 | Levofloxacin | 23.8 | 71.4 | 4.8 | 45 | 25 |
| 506-L5 | RG 506 | Levofloxacin | 23.3 | 69.8 | 7.0 | 55 | 25 |
| 506-L6 | RG 506 | Levofloxacin | 23.3 | 69.8 | 7.0 | 35 | 25 |
| 506-D1 | RG 506 | Dexamethasone | 23.3 | 69.8 | 7.0 | 45 | 25 |
| 506-D2 | RG 506 | Dexamethasone | 20.4 | 61.2 | 18.4 | 45 | 25 |
| 756-L1 | RG 756 | Levofloxacin | 23.3 | 69.8 | 7.0 | 45 | 25 |
| 756-L2 | RG 756 | Levofloxacin | 22.2 | 66.7 | 11.1 | 45 | 25 |
| PDLLA-L1 | PDLLA | Levofloxacin | 23.3 | 69.8 | 7.0 | 45 | 25 |

FIG. 33
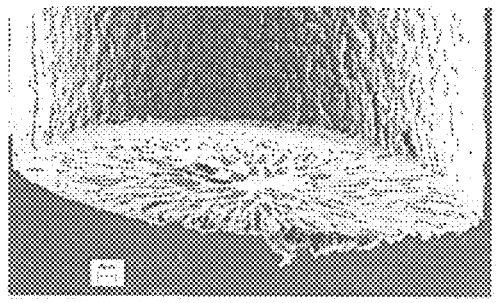
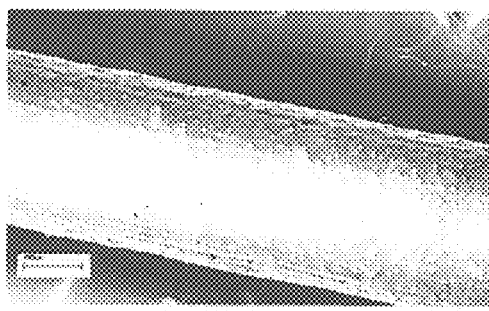
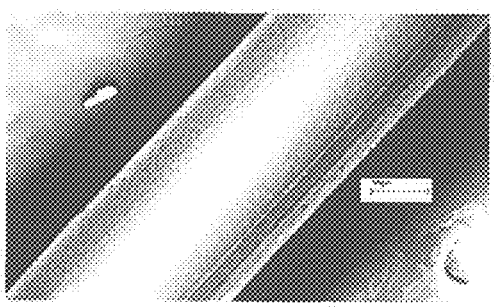

FIG. 37
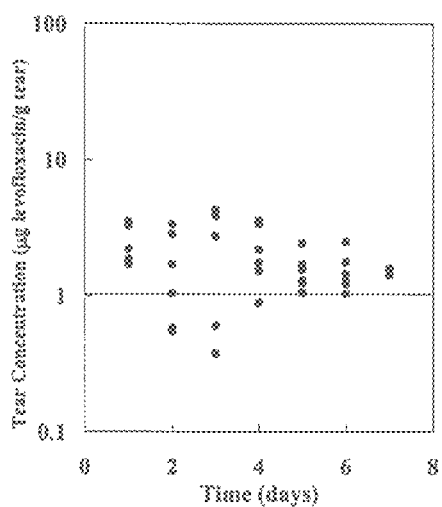
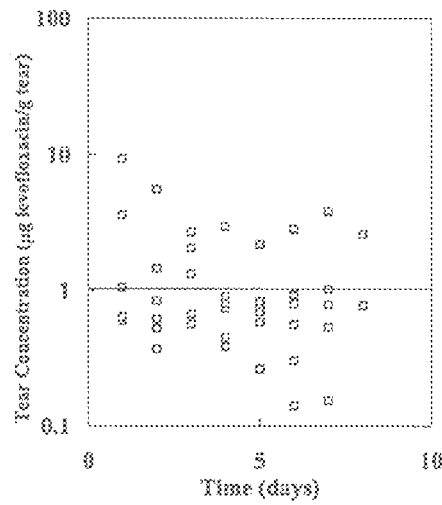
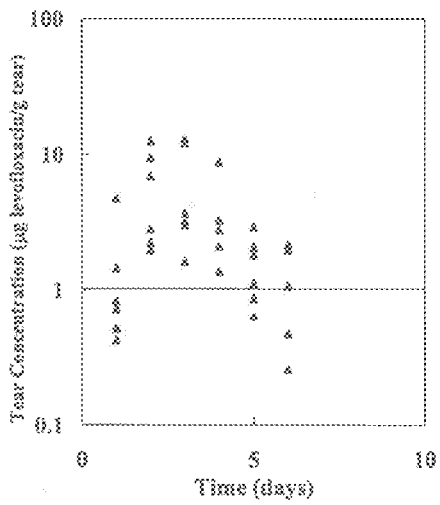

LAYERED DRUG DELIVERY POLYMER MONOFILAMENT FIBERS

CROSS-REFERENCE TO RELATED APPLICATIONS

The current application claims priority to U.S. Provisional Application No. 61/002,874, filed Nov. 12, 2007, and U.S. Provisional Application No. 61/124,173, filed Apr. 15, 2008, the disclosure of which are incorporated herein by reference.

FIELD OF THE INVENTION

The current invention is directed to layered multi-component polymer monofilament fibers; and more particularly to layered multi-component polymer monofilament fibers for use in the administration of therapeutics.

BACKGROUND OF THE INVENTION

Localized controlled release of therapeutics maximizes the effectiveness of a drug by selectively delivering the drug to a particular site. Local drug delivery decreases systemic exposure to a drug and avoids potentially dangerous peak and trough drug levels in patients. To this end, many devices have been developed to deliver drugs in a controlled, localized manner.

Although devices can be made into many different morphologies including microspheres, in-situ forming gels, films, and injectable depots, fibrous morphologies are intriguing because they allow for easy implantation/removal of a device, anchorability in tissue, and mechanical stability. (See, e.g., Langer, R., Chemical Engineering Science 1995, 50, (24), 4109-4121; Batycky, R. P., et al., Journal of Pharmaceutical Sciences 1997, 86, (12), 1464-1477; Freiberg, S., et al., International Journal of Pharmaceutics 2004, 282, (1-2), 1-18; and Wang, Y, et al., Biomaterials 2004, 25, (18), 4279-4285, the disclosures of each of with are incorporated herein by reference.) Fibrous devices can also provide mechanical stability or be woven with other fibrous components that are more mechanically stable.

As a result, encapsulating therapeutics within polymer matrices is a well established method of controlling the release of drug molecules. Biodegradable polymers are often used to control drug release and facilitate full device erosion. (See, e.g., Kohn, J., et al., Biodegradable and Bioerodible Materials. In Biomaterials Science Second Edition, Elsevier Academic Press: San Diego, Calif., 2004, pp 115-127; and Langer, R., 1995, the disclosures of which are incorporated herein by reference.) Copolymers made of lactide and glycolide monomers are common biodegradable polymers that are commercially available over a range of molecular weights and lactide to glycolide ratios. Since both molecular weight and lactide to glycolide ratio affect polymer degradation and therapeutic release, careful selection of a poly(lactide-co-glycolide) (PLGA) can achieve many temporally different release patterns. (See, e.g., Alexis, F., Polymer International 2005, 54, (1), 36-46; and Siepmann, J., et al., Advanced Drug Delivery Reviews 2001; 48(2-3):229-247, the disclosures of which are incorporated herein by reference.)

Common methods for making fibrous devices for drug delivery include electrospinning and wet spinning. (See, e.g., Kim, K., et al., Journal of Controlled Release 2004, 98, (1), 47-56; Kenawy, E. R., et al., Journal of Controlled Release 2002, 81, (1-2), 57-64; Zeng, J., et al., Journal of Controlled Release 2005, 105, (1-2), 43-51; Crow, B. B., et al., TISSUE ENGINEERING 2005, 11, (7/8); Crow, B. B., et al., Biopolymers 2006, 8, (6), 419-427; Gao, H., et al., Journal of Controlled Release 2007, 118, (3), 325-332; and Zilberman, M., et al., J Biomed Mater Res Part B: Appl. Biomater. 2005, 74, 792-799, the disclosure of each of which are incorporated herein by reference.) A particular method is usually chosen based on design criteria for the particular application and nature of the polymer. Electrospinning can be used to make fibers of micron to submicron diameters and is typically used to make non-woven meshes. (See, e.g., Fridrikh, S. V., et al, Physical Review Letters 2003, 90, (14), 144502; Subbiah, T., et al., Journal of Applied Polymer Science 2005, 96, (2), 557-569, the disclosures of which are incorporated herein by reference.)

Wet spinning is perhaps the earliest form of fiber processing and is done by dissolving a polymer in a solvent and extruding the solution into a non-solvent. The extrusion process typically happens by forcing the polymer solution through an orifice into a coagulation bath with an uptake bobbin pulling the fiber and spooling the final product. The solvent diffuses out of the polymer at rates dictated by miscibility of the solvent with the non-solvent, density of the polymer solution, temperature of the process, and other process parameters. The fiber coagulates when the polymer reaches a critical point and phase separates. Solvent is removed by prolonging the contact with the non-solvent, exposing the fiber to various non-solvent baths, or simply drying out the remaining solvent. The result is a solid polymer filament that may be further processed into yarn, textiles, sutures, or other devices. Traditional fiber drawing uses semi-crystalline polymers since the drawing procedure helps to align the crystalline regions of the polymer and enhance the mechanical properties in the direction of fiber drawing. To this end, post extrusion processing such as cold drawing is used to enhance crystallinity and strengthen fibers. Benefits of a wet-processed fiber include a porous microstructure, room temperature processing conditions, and diameters of suture-like scale. Fibers made from two phase solutions, such as emulsion or solid suspensions, have been shown to be effective in controlling therapeutic release and have been used primarily for tissue engineering and cancer therapy.

Poly(lactide) and poly(glycolide) are biodegradable polymers commonly used for medical applications. Their copolymer, PLGA, is commonly used for drug delivery applications. Poly(lactide) comes in two varieties, the single enantiomer poly(l-lactide) (PLLA) and the racemic poly(dl-lactide) (PDLLA). This slight difference in stereochemistry results in significantly different properties, since PLLA is semicrystalline and PDLLA is always amorphous. Poly(glycolide) is semicrystalline but copolymers of glycolide and lactide are almost always amorphous, the exceptions being copolymers with very high or very low glycolide to lactide ratios (l-lactide only). The semicrytalline versions of PLGA are useful for structural applications, such as sutures, since the crystallinity will increase the strength of the material. Amorphous PLGA is more useful for drug delivery, since the lack of crystallinity allows for the uniform distribution of drug throughout the polymer matrix. The release of drugs from PLGA can be tuned by the varying the ratio of lactide to glycolide since this ratio determines the degradation rate of the polymer. The fastest degrading PLGA is the 50:50 copolymer, with other copolymers taking longer to degrade as the ratio skews one way or the other. PLGA is a polyester and degrades by hydrolysis to give lactic acid and glycolic acid.

Drug release has been quantitatively linked to PLGA degradation by several groups, with one rigorous model described by Batycky et al. (See, e.g., Batycky, R. P., et al., Journal of Pharmaceutical Sciences 1997, the disclosure of which is incorporated herein by reference.) This model describes drug release from PLGA and PLA microspheres made by an emulsion process. This technique leaves isolated pockets containing protein throughout a polymer microsphere. As the spheres degrade, a system of interconnected pores forms between the pockets and the surface. The pores start at various sizes, but small pores (micropores) will not allow the protein to diffuse through. When large pores (mesopores) bridge between a certain pocket and the surface, the drug may diffuse out. This model takes into consideration hydration time for the polymer, degradation rates, and diffusivities and is able to accurately describe the drug release from the microspheres. These microspheres show a three phase release profile, with an initial burst, a period with low release, and a final period of sustained release. Hydration of the sphere should be quick (calculated at 8 min based on physical parameters of the spheres) so burst release is taken to be due to adsorbed molecules or drug that already is bridged to the surface by mesopores. Later work by found that at least some of the burst is due to the swelling of the pores associated with hydration. The swelling causes some of the pores to bridge to the surface of the sphere, causing rapid drug release. The second region of drug release is an induction period where little drug is released. This is due to initial porosity being low and most of the pores being small. The protein is unable to diffuse through the small, sparse pores and there is little drug release for a period of several days to weeks. The third phase of sustained release is due to polymer degradation causing the proliferation of mesopores, allowing the protein to escape. This three phase model of release is widely reported and is the main model of release for biodegradable polymer devices.

In a technical report, Nelson et al described a wet spinning procedure for PLGA and PLLA fibers. (See, Nelson, K. D., et al., Tissue Engineering 2003, 9, (6), 1323-1330, the disclosure of which is incorporated herein by reference.) This report focuses on semi-crystalline PLLA fibers but mentions that PLGA fibers made by the same techniques degrade faster than PLLA fibers (2 months for PLGA compared to more than 5 months for PLLA). These fibers are mechanically stable enough for a tissue engineering scaffold with PLLA being particularly useful due to the longer time for degradation. This technique was used to encapsulate drug by an emulsion method. (See, Crow, B. B., et al., TISSUE ENGINEERING 2005, 11, (7/8), the disclosure of which is incorporated herein by reference.) Protein was dissolved in water, which was emulsified in a polymer/methylene chloride solution. The emulsion was extruded into hexanes for coagulation with a draw ratio of 41. The fibers in this case had a maximum drug loading of 2.38 wt % to start, but final drug loadings are not provided. The process for making the fibers is very similar to processes for making w/o/w emulsion based microspheres, and the release profile is also very similar. There is an initial burst of drug ranging from 5-15%, followed by an induction phase lasting to 5 weeks, and a release portion governed by degradation. The burst region is higher for PLLA fibers and for the PLLA fibers, fibers with 10% aqueous loading have a higher burst than 5% aqueous loading. Oddly, the induction phase seems to be equivalent for PLLA and PLGA despite the much faster degradation of PLGA. In the degradation release phase, PLGA releases much faster than PLLA. It is unclear why PLGA releases the vast majority of the drug load from 5-11 weeks when complete polymer degradation happens at 7 weeks.

Building on the emulsion fibers, Gao et al used a simple particle suspension instead of an emulsion to control the release of 5-fluorouracil from PLLA fibers. (See, e.g., Gao, H., et al., Journal of Controlled Release 2007, 118, (3), 325-332, the disclosure of which is incorporated herein by reference.) The spinning technique did not use any uptake, so diameters were varied and depended upon the molecular weight of the polymer and polymer concentration. No diameter attenuation was used. The result was a fiber with high drug loading (75-90% of initial drug) and diameters spanning from 65-152 mm. Drug release was monitored only through the burst phase, with maximum measurements at 25 days (corresponding to less than a 1% drop in fiber mass). In this way, drug release was not dependent on polymer degradation but was instead controlled by thickening the polymer phase and shrinking the particle size of the drug. Most of the fibers described had sudden bursts of 10-90% followed by induction phases, but sometimes the burst could be slowed to give a controlled release over several days. Mechanical properties were not examined, but work by Zilberman et al on wet-spun PLLA fibers for stents suggests that these fibers should retain almost total strength over at least 6 weeks. (See, e.g., Zilberman, et al., J Biomed Mater Res Part B: Appl. Biomater. 2005, the disclosure of which is incorporated herein by reference.)

Although these techniques and experiments have shown that there is promise in these fiber release systems, a drawback to these systems is that drug release due to degradation cannot be decoupled from mechanical properties unless release is diffusion limited. This limits the usefulness of such devices since degradation controlled release is desirable for many circumstances, including long term release and modulated release. In addition, by using only a single polymer, release can only occur over a single given time interval. Moreover, these devices can only encapsulate a single drug and conditions for encapsulation and controlled release may not be general across all drugs. Accordingly, there is a need for improved fibrous drug delivery systems capable of having a more flexible drug release mechanism.

BRIEF SUMMARY OF THE INVENTION

Thus, there is provided in the practice of this invention according to a presently preferred embodiment, a layered multi-component sustained-release drug polymer monofilament fiber system suitable for implantation in a patient. The invention describes a monofilament polymer that comprises any number, but at least two, side-by-side layers, where a portion of each of the layers is exposed to the environment. These layers in turn may be combined with one or more therapeutic agents or drugs such that a single unitary drug-eluting monofilament fiber may be formed.

In another embodiment, the layered fiber of the invention further includes a plurality of distinct segments along its axial length, each segment may comprise different numbers and types of layers.

The invention also contemplates a thread comprising one or more fibers. In certain embodiments, the thread comprises one or more fibers that are non-bioabsorbable.

In certain embodiments, at least one additional fiber of the thread comprises one or more therapeutic agents or adjuvants.

In still another embodiment, a number of the multi-component layered fibers of the current invention may be formed into a thread. In certain embodiments, the thread is a monofilament. In other embodiments, the thread is a polyfilament. In certain embodiments, the thread is braided.

The present system also affords the ability to manipulate various variables in the drug delivery process. In particular, the method of controlling the rate of drug delivery can be tuned by controlling the characteristics of the individual layers of the polymer/thread or fiber system, such as chemical composition, mode of fabrication, and structural design. Methods of controlling drug delivery by chemical composition include: selection of different polymer types with different rates of biodegradability, use of polymers of differing molecular weights, incorporation of various additives to the drug-polymer matrix (including cyclodextrins), and use of different drug and prodrug forms.

In certain embodiments, the fiber gradually releases the therapeutic agent over a period of time after implantation in a patient. In other embodiments, the fiber releases an initial surge of the therapeutic agent after implantation in a patient. In further embodiments, the fiber releases a gradually increasing amount of the therapeutic agent over a period of time after implantation in a patient.

In certain embodiments, the therapeutic agent is present throughout the width of one or more sections of the fiber. For example, the therapeutic agent may be present at a substantially uniform concentration throughout the width of one or more sections of the fiber.

In certain embodiments, the fiber comprises one or more coatings. In certain embodiments, the coating comprises one or more therapeutic agents or adjuvants.

Elements of structural design that can be used to adjust delivery rate, amount, and duration include the incorporation of drug-polymer bulbs as reservoirs for drugs, use of surface coatings and/or multi-walled components, as well as use of a ribbon configuration. The drug polymer bulb can be delivered to desired tissue utilizing the thread and needle system and can deliver increased amounts of drug in local or systemic fashion. The bulb may be sized and shaped to facilitate entry into the tissue, for example, by being tapered in the direction of insertion. The bulb may also be sized and shaped to impede spontaneous extrusion of the bulb, for example by including bumps, ridges, barbs, etc. In some embodiments, one or more fibers are in a ribbon configuration, presenting a flexible, flat and thin profile, which can be used to adjust implant surface area and delivery time. A ribbon configuration can also serve as a drug-eluting barrier that separates tissue structures. In such an embodiment, the thread may have a tube-like structure or configuration, defining a hollow core. For example, the fiber may include a lumen. In certain embodiments, the lumen contains a medium that includes one or more auxiliary therapeutic agents.

Many different types of biodegradable polymers are contemplated by the systems disclosed herein. For example, polymer systems comprising Dexon, Vicryl, Polysorb, as well as poly(lactide-coglycolide) (PLGA), polyglycolic acid (PGA), and polylactic acid (PLA), polycaprolactone (PCL), polydioxanone (PDO), or a combination thereof.

In certain embodiments, the therapeutic agent is a nucleic acid, a protein, a peptide, a small molecule, or a combination thereof. In some embodiments, the therapeutic agent is a small molecule. For example, the therapeutic agent may be a steroid, a retinoid, a NSAID, a vitamin D3 analog, a human carbonic anhydrase inhibitor, or a combination thereof. In certain embodiments, the therapeutic agent is a steroid, such as a corticosteroid, prednisolone, and/or dexamethasone. In certain embodiments, the therapeutic agent is a protein, for example, a neurotrophic factor, such as a nerve growth factor.

In certain embodiments, the therapeutic agent is an anticancer agent, an antibiotic agent, an anti-inflammatory agent, an immunosuppressant, an antiviral agent, an anti-proliferative agent, an antimicrobial agent, a nerve growth inducing agent, or a combination thereof. In certain embodiments, the therapeutic agent is an antibiotic agent or an anti-microbial agent.

In certain embodiments, the therapeutic agent is an antibiotic agent or an anti-microbial agent, for example, chlorhexidine, metronidazole, minocycline, tetracycline, triclosan, ciprofloxacin, levofloxacin or tobramycin.

In certain embodiments, the therapeutic agent treats an ocular disease or disorder, for example, corneal ulcer, uveitis, scleritis, glaucoma, or vernal conjunctivitis. In certain embodiments, the therapeutic agent is ciprofloxacin, 5-fluorouracil, tobramycin, dexamethasone, prednisolone, or combinations thereof.

In certain embodiments, the therapeutic agent treats periodontitis. For example the therapeutic agent may be chlorhexidine, metronidazole, minocycline, triclosan, or tetracycline.

In certain embodiments, the tissue is nerve tissue. In certain embodiments, the therapeutic agent is a neurotrophic factor. In certain embodiments, the therapeutic agent induces nerve growth, for example, sabeluzole or inosine.

In certain embodiments, the therapeutic agent is covalently linked to the polymer. The therapeutic agent may be covalently linked to the polymer by one or more linking moieties. In certain embodiments, one or more linking moieties may be cleaved under physiological conditions.

In certain embodiments of the invention the drug release, mechanical properties, and degradation of the monofilament controlled release device is further controlled by the addition of various hydrophobic molecules.

In certain embodiments, the therapeutic agent forms an inclusion complex with the cyclodextrin.

In certain embodiments, the cyclodextrin and polymer are not covalently linked. In certain embodiments, the fiber comprises one or more non-cyclodextrin containing polymers, for example, in addition to a cyclodextrin containing polymer. In certain embodiments, the non-cyclodextrin containing polymer is poly(lactide-coglycolide) (PLGA).

In some embodiments, the cyclodextrin and polymer are covalently linked. In certain embodiments, the cyclodextrin is incorporated in the backbone of the polymer. In other embodiments, the cyclodextrin is borne in side chains of the polymer.

In certain embodiments, the cyclodextrin is a modified cyclodextrin. For example, the cyclodextrin may be benzylated, acylated, or alkylated. The cyclodextrin may be a methylated cyclodextrin, a hydroxypropylated cyclodextrin, or a sulfobutylether cyclodextrin.

The present invention also considers methods for the fabrication of fibers, threads, and tubes disclosed herein. In some embodiments, wet-spinning methods are employed for the preparation of the present fibers. In certain embodiments, a coagulating fluid comprising one or more solvents, such as water and an organic alcohol, such as isopropanol, may be employed. Surfactants, such as anionic surfactants like sodium dodecylsulfate, may also be employed during the fabrication process. Preparation of the agent-containing fiber may be done at ambient temperature. Formulation of the thread or fiber from the polymer may also be done at ambient temperature. The variables in the fabrication process, such as coagulation fluid, surfactant additives, and temperature, may be tuned to prepare fibers possessing desired pharmacological and physical properties.

The invention also provides a method for the preparation of a layered drug-eluting fiber comprising:
  a) dissolving at least two polymers and at least one therapeutic agent in at least two separate polymer solutions, each solution containing a solvent; and
  b) exposing the multiple polymer solutions to a common coagulation fluid
  c) to form a layered drug-eluting fiber.

In certain embodiments, exposing the polymer solution to a coagulation fluid comprises extruding the polymer solution into a coagulation fluid. In certain embodiments, exposing the polymer solution to a coagulation fluid comprises dip-coating.

In certain embodiments, the polymer solution is homogeneous.

In certain embodiments, the solvent is DMF, DMSO, or combinations thereof. In certain embodiments, the coagulation fluid is water, an alcohol, or a combination thereof. In certain embodiments, the alcohol is isopropanol. In certain embodiments, the coagulation fluid is a water:isopropanol mixture. In certain embodiments, the coagulation fluid includes a surfactant, for example, an anionic surfactant, such as sodium dodecylsulfate.

The invention also provides a method for delivering one or more therapeutic agents to a targeted tissue in a patient, comprising introducing a layered fiber to the targeted tissue, the fiber comprising:
a) an elongated fiber body defining a longitudinal axis, said fiber body being comprised of at least two polymeric layers adjacently disposed along an axis normal to the longitudinal axis of the fiber body, where at least a portion of each of the at least two polymeric layers is exposed to the external environment; and
b) at least one therapeutic agent disposed on at least one of the at least two polymeric layers of the elongated fiber body.

In certain embodiments, the fiber is implanted or affixed in a targeted tissue of a patient. For example, the tissue may be ocular tissue or periodontal tissue or nerve tissue.

In certain embodiments, the introduction of the fiber is reversible.

The invention also contemplates a fiber/suture comprising one or more layered fibers. For example, a suture may comprise two or more threads or fibers. In certain embodiments, two or more threads of the suture comprise different therapeutic agents. In such an embodiment, the suture may be attached to a needle.

In certain embodiments, the present invention provides a stent, shunt, or other tubular device. Such devices may consist of a monolithic polymer tube, a mesh tube formed from fibers as disclosed herein, or by coating a metal, plastic, or other stent with a polymer coating as described herein.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein:

FIGS. 1a to 2c: Provide schematics of exemplary embodiments of the layered fibers of the current invention (a & b); and a schematic of a prior art coated polymer;

FIGS. 2a to 2d: Provide schematics of exemplary embodiments of the layered fibers of the current invention (a to d);

FIGS. 9a to 9c: Provides Scanning Electron Microscope (SEM) images of a single layer fiber made using solution 1 of Example 2 (a) a single layer fiber made using solution 2 of Example 2(b), and a layered fiber with two different concentrations of levofoxacin (c);

FIG. 10: Provides a data graph of the release of levofloxacin from fibers made of RG 506, RG 756, and both exemplary layered polymers;

FIG. 24: Provides light microscope pictures of 0% stretched (top), 200% stretched (middle) and 500% stretched (bottom) at 10× magnification;

FIG. 28: Provides Table 4;

FIG. 33: Provides SEM Images clockwise from top-right fiber A, fiber B, and fiber C;

FIG. 37: Provides data graphs of the in-vivo levofloxacin tear concentrations for each fiber over the course of device release.

DETAILED DESCRIPTION OF THE INVENTION

The present invention is directed generally to a layered polymeric monofilament fiber drug delivery device, where each layer of the polymeric fiber device can contain a different polymer, drug, additive, or any combination or mixture thereof. The invention is also directed to a method of manufacturing such a layered polymeric monofilament fiber drug delivery device, and to devices and methods of treatments using the polymeric fiber device. The layered nature of the current monofilament polymeric device provides the capability to modulate the release of one or more drugs and/or the mechanical properties of the fiber so that drug release and device failure can be separately tuned to provide for the tailored introduction of therapeutically effective drugs or agents to a target tissue. Moreover, the fiber may comprise more than one distinct segments along its length, each segment itself having different combinations and/or numbers of layers thereby providing even greater freedom in the design of the therapeutic delivery device.

The provision of multiple distinct layers along multiple distinct segments in a single monofilament fiber allows for a therapeutic delivery device that provides maximum possible flexibility. The flexibility of the layered multi-segmented fiber therapeutic delivery device of the current invention can best be understood with reference to the unique layered physical structure of the inventive polymeric device. A generic sketch of the structure of the layered monofilament of the current invention is provided in FIG. 1a. As shown, the filament of the current device is not formed of a single coated fiber (10) as in the prior art device (FIG. 1b), but is instead formed from a plurality of unique and distinct layers (12, 12', 12") or strands, each of which are separately exposed to the environment and all of which are integrally joined together to form a single layered monofilament fiber. In other words, these are not separated fibers which are braided together, or a single fiber that has multiple coaxial coatings, this is a single monofilament fiber having multiple distinct layers, each of which is simultaneously exposed to the environment. The importance of this distinction can be understood by considering the mechanism of the delivery of a therapeutic agent to a target tissue. In the conventional coated fiber only one layer of the fiber at a time is exposed to the target tissue, meaning that despite the number of coatings the actual drug delivery is conducted in a serial fashion. In contrast, in the layered fiber of the present invention each and every layer of the polymer is simultaneously exposed to the environment meaning that each layer and each agent may act in a parallel fashion providing dramatically enhanced flexibility and functionality to the device.

Figure 1A:
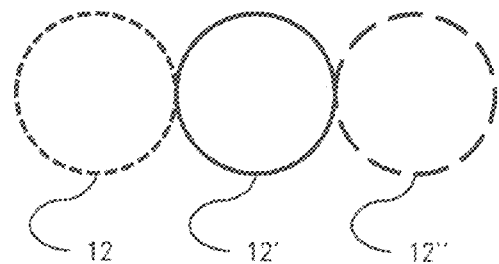
Figure 1B:
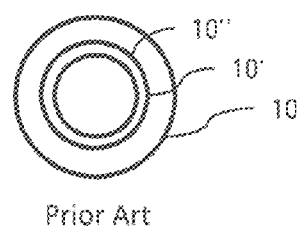
Figure 1C:
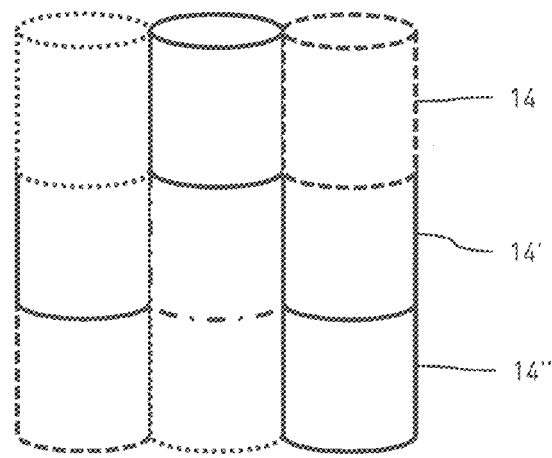

Moreover, as shown in FIG. 1c, the device also allows for the device to have distinct regions or segments (14, 14', 14") along its length, where each segment may be formed of different numbers and types of layers. Accordingly, different regions of the fiber may be designed to have different functions, either in terms of the delivery of therapeutic agents or with regard to the physical properties of the fiber itself.

Although the layered fiber drug delivery device of the current invention may be made of any number of layers, as shown in FIG. 1a, and any number and length of segments, as shown in FIG. 1c, they must at least have two layers, a portion of each of which is exposed to the environment, where at least one includes a therapeutic, and the layers must be able to be formed simultaneously into a single monofilament fiber using a common coagulation agent or non-solvent. Beyond these limitations, the layers and segments of the fiber may take any form relative to one another, including comprising different polymer materials, different therapeutic agents, different additives, etc.

Figure 2A:
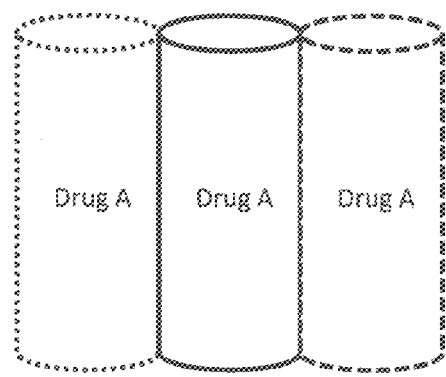

For example, in the embodiment shown schematically in FIG. 2a, a layered fiber of the current invention may comprise multiple layers releasing the same drug. In such an embodiment, each layer could be fashioned with a different biodegradable polymer. Individually, these layers would release their drug load over a relatively small time span, though the onset of release could be different. The resulting combined degradation profile would allow for the steady release of the therapeutic agent over a very long period of time. Alternatively, the polymers might be the same and the therapeutic agent itself provided in multiple forms. In this embodiment, the release would be dependent on the particle size of the therapeutic agent initially, then layers could be fashioned with multiple particle sizes to get a variant combined release profile. Therapeutic agents in different layers could also be provided in different forms, such as in crystal structures or physical states to again provide a variable release profile.

Figure 2B:
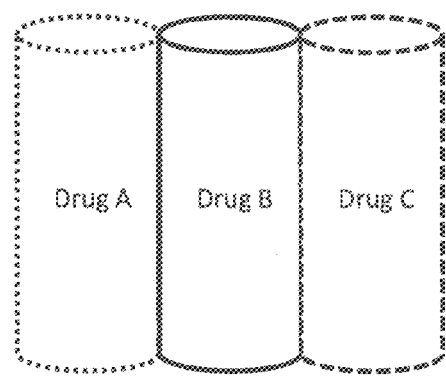

In another embodiment, as shown in FIG. 2b, the layers of the layered fibers of the current invention could contain different drugs, and control the rate of release for each. For example, if the layers of the inventive fiber are made of similar polymers, then the drugs could be released over the same time frame. Alternatively, if the layers are made of different polymers, the drugs could be released over different time frames, independent of the release of the other layers.

Figure 2C:
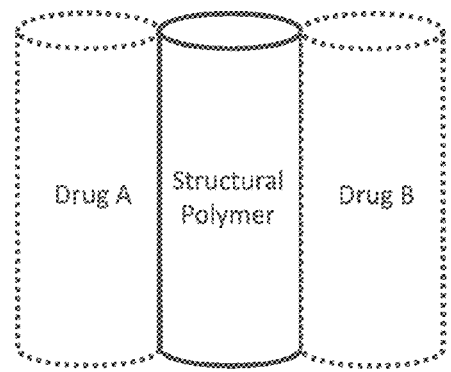

Finally, as shown in FIG. 2c, the different layers could be inserted into the inventive fiber to provide structural stability independent of the drug releasing layers. In one such embodiment for example, one layer of a multi-component fiber could be non-degradable or very slowly degradable. In this case, that layer would act as a stable anchor while the other layers degrade and release drug. This stabilizing layer could also be made of a higher strength or modulus material depending on the mechanical needs for the application. For example, the stabilizing layer could be a highly crystalline polymer while the releasing layers are mostly amorphous. Such a mixed phase fiber would be desirable since most controlled release polymers need to be amorphous, so that the therapeutic agent in question is not sequestered in a crystal structure, while most structurally sound polymer fibers are made from highly crystalline polymers.

As will be discussed further below, the multi-component layered fiber device of the current invention may also incorporate a number of additives that might impact the structural stability and/or drug release properties of the invention as well.

Figure 2D:
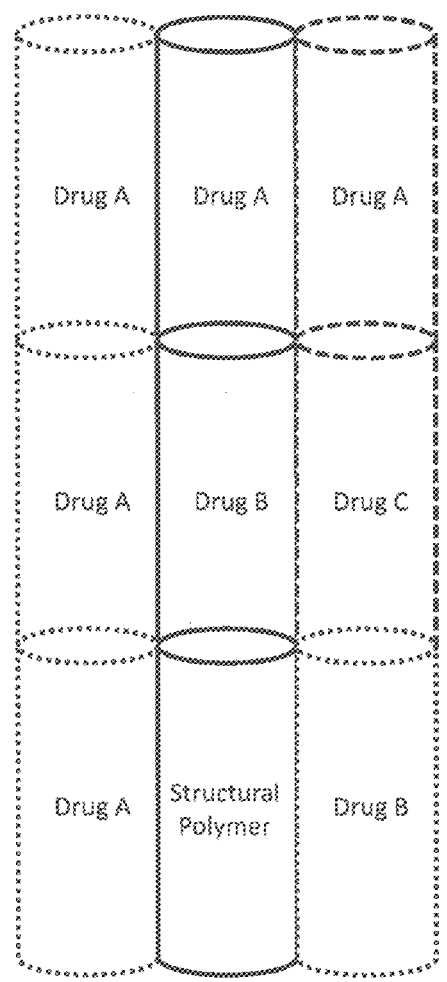

Although the above examples have only shown variance between layers in a single segment of the drug delivery fiber of the current invention, it should be understood that any or all of the above types of multi-component layered drug delivery fibers could be combined as independent segments in a single unitary fiber, as shown in FIG. 2d.

In short, because of the unique layered/segmented nature of the multi-component layered fiber device of the current invention, each individual layer and segment of the device can have specific mechanical and drug release properties, while still allowing the whole device to act as a single unit. In addition, each layer of each segment can itself contain 0, 1, or multiple drugs with one or more polymers blended together allowing for the ability to tailor the device to meet a near unlimited variety of drug delivery requirements.

Although the above discussion has focused on individual layered fibers, a number of the layered fibers of the present system may be combined into a single thread. The layered fibers may be interwoven, spun, tufted, or otherwise braided together to form the thread, or may be combined with other conventional fibers. Any such association of multiple layered fibers is intended to be encompassed by the term "thread" as that term is used herein. Furthermore, threads of the instant invention, in addition to comprising multi-component layered polymeric fibers as disclosed herein, may also be formed from the interweaving of other fibers followed by the fusing of these fibers by a suitable method, for example by treatment with heat and/or pressure. Threads may also be formed by the interweaving of two or more fibers followed by treatment with a cross-linking agent. Similarly, layered fibers and/or threads of the present invention may be further woven into fabrics, for example a cloth-like fabric. Such fabrics can be formed into various shapes, such as a conical shape or a tube-like shape, which may also serve as threads as described herein. In other embodiments, the fibers of the fabrics can be fused together by a suitable method, for example by treatment with heat, pressure, and/or cross-linking agents, to yield a film.

In embodiments of threads in which one or more of the fibers comprising the thread is not a layered monofilament of the invention any conventional fiber material may be used. For example, when a present thread is used as a suture, the suture may also comprise one or more fibers commonly used in sutures and/or capable of being used in sutures. Some non-limiting examples of such fibers include Vicryl®, Dexon®, PDS®, Maxon®, GORE-TEX®, Polysorb, poly(lactide-coglycolide) (PLGA), polyglycolic acid (PGA), polylactic acid (PLA), polycaprolactone (PCL), polydioxanone (PDO), Nylon, Dacron, Prolene, and co-polymers thereof, as well as silk, linen, catgut, and stainless steel. For example, in one embodiment, the biodegradable polymeric layered monofilament of the current invention may be combined or braided with non-absorbable material. In such embodiments, when the resulting thread is used as a suture, it may offer both permanent suture strength and temporary drug delivery. In one embodiment, the thread may include one or more biodegradable sections not including a drug or one or more sections of a non-absorbable material. Such a section may be placed at a tail end of the thread, where it could be readily accessed near the surface of the tissue to facilitate removal of part or the whole of the thread.

Although not discussed in detail fibers, threads and fabrics formed incorporating the multi-component layered fibers of the present invention may be used with any conventional treatment regime. For example, were the threads to be used as sutures they may be attached to a surgical needle. When multiple threads or filaments are implanted, the threads may have different properties. For example, the threads may deliver different drugs for different durations and at different rates. The drug delivery provided by the layered monofilaments of the current invention permits fast, controlled drug delivery to a target tissue providing local therapy without implant migration. The thread or layered fiber can be implanted in or tied to specific tissues to prevent implant migration, and hence to prevent drug delivery to non-targeted tissues. Alternatively, the thread or layered fiber can be implanted in subcutaneous tissue to allow absorption of the drug to the blood stream for systemic delivery. As such, the layered fiber or thread acts as a delivery vehicle for the drug or therapeutic agent and can be adjusted to provide local and/or systemic treatment without surgery. In such circumstances, the present system offers improved recovery of tissues from implantation as well as reduced incidence of complications, such as tissue infection, resulting from invasive surgery.

In addition to the multi-component layered polymeric fiber device itself, the present invention is also directed to a technique for manufacturing such fibers. The layered fibers of the present invention may be fabricated by any suitable method, for example such as by dry-spinning, gel-spinning, melt spinning, wet-spinning, or dry-wet spinning, including phase separation and/or membrane formation processes. Some examples of phase separation processes that are contemplated by the present invention include thermally induced phase separation and immersion precipitation. In some embodiments, dip-coating techniques may be employed for fabrication of the present fibers. For example, layered fibers formed as tube structures may be formed from dip-coating methods. Dip-coating or other analogous methods may be used to coat the subject polymeric materials onto any suitable structure, including traditional medical devices, such as stents or other devices. In addition to any suitable fabrication method, combinations of such methods may be employed.

Figure 3A:
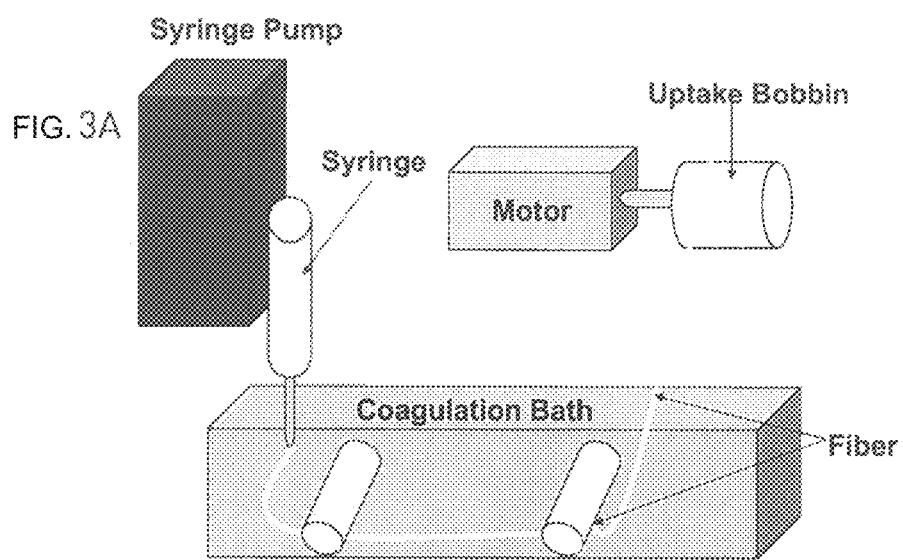
FIGS. 3a and 3b: Provide schematics of the creation of layered two component device through a Y-connector (a); and a wet-spinning apparatus (b)
Figure 3B:
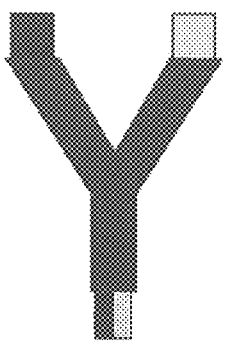

In one embodiment, a layered fiber of the present invention is prepared by a wet spinning method. Wet-spinning is a common method of producing filaments, and could be easily used to make devices as described. Since the viscosity of polymer solutions is lower than melts in general, creating a spinneret with a polymer solution is relatively easy compared to a melt. Using solutions with similar solvents also encourages polymer fusion at the interface between layers, ensuring a monofilament that is bound together. In wet-spinning, polymer solutions are formed into filaments by extrusion into a coagulation bath. For the current layered fiber device, polymer and drug can be dissolved in a common solvent or compatible solvents and extruded into a non-solvent for the polymer, precipitating the polymer and encapsulating the drug. Multiple polymer solutions are then joined prior to coagulation to create a layered multi-component layered fiber, as shown in FIGS. 3a and 3b. Accordingly, a generic statement of one embodiment forming a layered drug-eluting monofilament is prepared by:

a) separately dissolving at least two polymers and at least one therapeutic agent in the same or compatible solvents in at least two separate polymer solutions; and b) extruding the multiple polymer solutions into a common coagulation fluid c) to prepare a layered drug-eluting monofilament.

In some embodiments, dissolving the polymer and the therapeutic agent complex gives a homogenous solution. In certain embodiments, the solvent is a polar organic solvent or a non-polar organic solvent. Examples of non-polar organic solvents contemplated by the invention include benzene, hexanes, pentane, toluene, diethyl ether, chloroform, ethyl acetate, THF, dioxane, and methylene chloride. In some embodiments, the polar organic solvent is protic. In other embodiments, the polar organic solvent is aprotic. Examples of protic polar solvents contemplated by the invention include water, methanol, ethanol, propanol (all isomers), butanol (all isomers), acetic acid, and formic acid. In preferred embodiments, the solvent is a polar, aprotic organic solvent, such as DME (1,2-dimethoxyethane), NMP (N-methylpyrrolidinone), acetonitrile, acetone, DMF (dimethylformamide), DMSO (dimethyl sulfoxide), nitrobenzene, pyridine, or combinations thereof, particularly DMF or DMSO.

In certain embodiments, the layered fiber fabrication method may employ one or more coagulation fluids so long as the coagulation fluids incorporate a non-solvent compatible with all of the layers being formed within any single segment, and the invention contemplates all suitable coagulation fluids. In some embodiments, the coagulation fluid may be water, a non-polar organic solvent, a polar organic solvent, such as an alcohol, or combinations thereof. Examples of alcohols suitable for use as coagulation fluids include methanol, ethanol, propanol, butanol, and pentanol. All isomeric forms of such alcohols are contemplated, for example, isopropanol, tert-butanol, n-pentanol, etc. In some embodiments, combinations of solvents may be used as coagulation fluids, such as water:isopropanol. The exact combination and ratio of solvents may be tuned to give a coagulation fluid which affords fibers of desired properties. For example, a coagulation fluid of 75:25 water:isopropanol may afford higher loading of a therapeutic agent in the fiber than a coagulation fluid of water alone.

In certain embodiments, a coagulation fluid may also contain one or more suitable surfactants and/or detergents. For example, the present invention contemplates the use of anionic, cationic, non-ionic, and ampholytic surfactants. Some non-limiting examples of surfactants that may be used with the present invention include sodium dodecylsulfate (SDS), sodium cholate, sodium deoxycholate (DOC), N-lauroylsarcosine sodium salt, lauryldimethylamine-oxide (LDAO), cetyltrimethylammoniumbromide (CTAB), and bis (2-ethylhexyl) sulfosuccinate sodium salt (DOSS), particularly SDS. The type and amount of surfactant use in the coagulation fluid may be tuned to give a coagulation fluid which affords monofilaments of desired properties, such as increased loading of a therapeutic agent in the Layered fiber. In some embodiments, the surfactant may be employed in a 0 to 10% solution with a coagulation fluid, for example, in an approximately 2% solution.

The temperature at which layered fiber formation is conducted may be tuned to afford fibers of desired properties. The temperature may also be adjusted to account for the stability of one or more therapeutic agents loaded into the layered fiber. For example, temperatures near or slightly above ambient may be employed when using heat-sensitive therapeutic agents, such as biological agents, for example, proteins, peptides, or polynucleotides. Thermal decomposition of such agents may be avoided. Additionally, potentially harmful and/or toxic decomposition products may also be avoided. Such thermally sensitive drugs may not be compatible with systems that rely on formation of the monofilament by heating and thus wet-spinning is generally preferred. As such, formation of the layered fiber from one or more drug or agent containing polymers may be done at temperatures below 60° C., below 50° C., below 40° C., below 30° C., or below 20° C., particularly below 30° C.; such procedures are typically performed at temperatures above 0° C., 10° C., or 20° C. Thus, for example, the process can be conducted at a temperature in the range of 0-60° C., 10-50° C., 15-40° C., or 20-30° C. In some embodiments, formation of the monofilament may occur at ambient temperatures. Formation of the monofilament at ambient temperatures may facilitate the preparation of layered fibers with consistent and reproducible drug loadings.

Examples of fiber fabrication methods that could be modified to form the layered fibers of the current invention include those described in van de Witte, et al. *J. Control. Rel.* 1993, 24, 61-78 and Nelson et al. *Tissue Engineering,* 2003, 9, 1323-1330; the entire contents of which are hereby incorporated by reference.

It should be understood that a drug-eluting layered fiber of the present system may vary in size. In some embodiments, the monofilament may be several centimeters long and/or a few millimeters thick. In other embodiments, the monofilament is only a few millimeters long and/or less than a millimeter thick. The physical dimensions of the layered monofilament of the present system may be tuned to achieve desired properties in drug loading, duration of drug release, and physical properties such as tensile strength and flexibility. For example, the instant layered fiber may be adjusted to deliver a substantially constant amount of therapeutic agent or drug over a predetermined period of time, such as a day, three days, a week, or longer. The instant layered fiber may also be adjusted to deliver a large initial dose of therapeutic agent and/or to taper the dose. The instant layered fiber may also be adjusted to provide a delay in achieving high dosage levels, i.e., a gradual increase in drug release rate up to a target dosage. Alternatively, individual layers of the Layered fiber may have characteristics of each of these types of release profiles.

Figure 4A:
FIGS. 4a and 4b: Provide Illustrative examples of bulbs of the present invention.
Figure 4B:

A drug-eluting layered fiber of the present system may also employ engineered structures such as a bulb, i.e., a thickened segment. FIGS. 4*a* and 4*b* depict illustrative embodiments of a fiber of the present invention incorporating a bulb segment. Use of a bulb is advantageous for the implantation and delivery of large amounts of therapeutic agents or for the long-term and sustained release of an agent or drug. The bulb may serve to act as a reservoir for the agent or drug. The bulb may have a similar composition to the rest of the layered fiber, i.e., similar construction of layers, plies, interweaves, or polymeric composition. Alternatively, the layered fiber may comprise a different segment having a composition distinct from the narrower segments of the monofilament system, possibly to present a different drug delivery profile. The bulb composition may or may not be biodegradable. Furthermore, the bulb segment may be used in tandem with one or more additional bulb segments, which may have similar or different properties from other bulbs and/or the remainder of the thread or fiber system. FIG. 4*b* depicts an illustrative embodiment of a layered fiber of the present invention incorporating multiple bulb segments. Tandem and multiple bulb segments may increase the amount of drug that can be delivered by the layered fiber system. In certain embodiments, a bulb may include a therapeutic agent that is not present in other portions of the layered fiber, and different bulbs may contain different therapeutic agents from each other. Such therapeutic agents may have complimentary properties and/or work synergistically. For example, for a suture application, the thin portions of the monofilament may include a local anesthetic, while bulbs may include an antibiotic. When used in conjunction with a suture system of the invention, the bulb may be introduced into a desired location by being pulled through tissue using the needle system described herein.

An additional physical attribute of the bulb feature is that the bulb(s) prevents migration of the layered fiber from the site of implantation due to the larger diameter of the bulb segment versus the sites of implantation. For example, the bulb may be tapered in the direction of insertion, such as in a conical or arrow shape, to discourage retraction or spontaneous extrusion. Additionally, the bulb may also be sized and shaped to impede retraction or spontaneous extrusion, for example by including bumps, ridges, barbs, etc. In certain embodiments, the layered fiber may include segments that include one or more surface features, which permit passage of the layered fiber in the direction of insertion/implantation, but discourage passage in the opposite direction. For example, the layered fiber may include one or more segments or surface portions which lie flat when the layered fiber is pulled in one direction, such as the direction of implantation, so as to not impede passage of the layered fiber through the surrounding tissue. Such segments or portions of the layered fiber may then flare out and/or catch or burrow into surrounding tissue when layered fiber is pulled in a direction opposite to implantation, thus impeding passage and migration of the monofilament in this direction. Such surface features may also be employed on a bulb section. Structural features of the layered fiber which inhibit migration permit focused implantation of the thread or fiber and hence drug delivery system to specifically targeted tissues and may reduce delivery to non-targeted tissues.

Another aspect of the invention considers one or more ribbon configurations, wherein the layered fiber possesses in a flexible, flat and/or thin profile or shape, which can be used to adjust implant surface area and delivery time of the drug. For example, a ribbon may have a width at least five, ten, or even twenty, thirty, one hundred or more times as great as the thickness of the ribbon. The thickness of the ribbon is typically less than 2 mm, 1 mm, 0.5 mm, or even less than 0.1 mm, preferably less than 0.5 mm. A ribbon configuration can also serve as a drug-eluting barrier that separates tissue structures of similar or different composition.

Turning to the materials used to construct the layered fiber of the current invention. First, it should be recognized that a variety of polymers may be suitable to form the layered fiber of the present invention so long as the polymers in any single layer of the layered fiber may be formed using the same or compatible non-solvents (i.e., coagulation fluids). Preferable at least one biodegradable polymer is incorporated into the layered fiber to provide a release vehicle for the therapeutic agent.

Exemplary biodegradable polymers include, poly(lactide) and poly(glycolide), which are commonly used for medical applications. Their copolymer, PLGA, is commonly used for drug delivery applications. Poly(lactide) comes in two varieties, the single enantiomer poly(l-lactide) (PLLA) and the racemic poly(dl-lactide) (PDLLA). This slight difference in stereochemistry results in significantly different properties, since PLLA is semicrystalline and PDLLA is always amorphous. Poly(glycolide) is semicrystalline but copolymers of glycolide and lactide are almost always amorphous, the exceptions being copolymers with very high or very low glycolide to lactide ratios (l-lactide only). The semicrytalline versions of PLGA are useful for structural applications, such as sutures, since the crystallinity will increase the strength of the material. Amorphous PLGA is more useful for drug delivery, since the lack of crystallinity allows for the uniform distribution of drug throughout the polymer matrix. The release of drugs from PLGA can be tuned by the varying the ratio of lactide to glycolide since this ratio determines the degradation rate of the polymer. The fastest degrading PLGA is the 50:50 copolymer, with other copolymers taking longer to degrade as the ratio skews one way or the other. PLGA is a polyester and degrades by hydrolysis to give lactic acid and glycolic acid.

In addition, the layered fibers may incorporate polymers that are largely insoluble in physiological fluids. Suitable polymers may include naturally occurring or synthetic polymers. Certain exemplary polymers include, but are not limited to, Dexon, Vicryl, Polysorb, poly(lactide-coglycolide) (PLGA), polyglycolic acid (PGA), polylactic acid (PLA), polycaprolactone (PCL), polydioxanone (PDO), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl acetates, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinyl-chloride-diethyl fumerate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitrile copolymer, etc.

The instant invention may employ polymers such as PGA, PLGA, etc., which are FDA approved. Some embodiments employ PLGA in particular. It is known that PGA, PLA and PLGA can be prepared as layered monofilament fibers by wet-spinning (Nelson et al., 2003 and references therein, the disclosures of which are incorporated herein by reference).

The therapeutic agent may range from a nucleic acid (such as a vector, an RNAi construct, or an antisense oligonucleotide) or protein to a small organic molecule. In certain embodiments, the agent is an anti-cancer (such as camptothecin or related derivatives), anti-fungal, anti-bacterial, anti-mycotic, or anti-viral therapeutic. In certain embodiments, the agent is a receptor antagonist. In certain embodiments, the therapeutic agent is a protease inhibitor. In certain embodiments, the therapeutic agent is a nerve growth factor. Furthermore, a polymer of the present invention may contain one kind of therapeutic agent or may contain more than one kind of therapeutic agent. For instance, two or more different cancer drugs, or a cancer drug and an immunosuppressant, or an antibiotic and an anti-inflammatory agent may be included in the composition.

As discussed above, in certain embodiments the layered fiber may be used as a suture to treat wounds (i.e., to promote wound healing). For example, when layered fibers of the invention are combine both drug delivery and structural polymers, the suture may provide both permanent suture strength and local drug delivery. Such compositions may also include as the drug or agent, for example, PDGF-B or an expression vector for producing PDGF-B in a target cell, stimulators of cell proliferation or differentiation, stem cells or progenitor cells, and/or other compounds known to be effective in promoting tissue repair, healing, inhibiting infection, etc., such as growth factors, including protein growth factors. In an illustrative example, a suture comprising a non-absorbable layer and a biodegradable layer containing a growth factor may be employed in the repair of torn tendons or ligaments.

In some embodiments, the present biodegradable implant system containing corticosteroid, anti-inflammatory drug, angiogenesis-inhibiting agent, or anti-metabolite drug may be used to inhibit pathologic fibrosis, scarring, and neovascularization. For example, the system can be used in the prevention of keloid formation after skin wound healing by using a corticosteroid-eluting thread or fiber to reduce fibrosis.

According to an aspect of the invention, a biodegradable layered fiber with a ribbon configuration containing corticosteroid or 5-fluorouracil, for example, may function as a drug-eluting barrier and be used to separate tissue structures and prevent adhesions of tissues. A biodegradable ribbon layered fiber implant system containing corticosteroid or 5-fluorouracil may also be used to improve glaucoma surgery outcomes by reducing postoperative fibrosis and scarring. The use of a biodegradable ribbon implanted at the time of glaucoma surgery to provide sustained release of 5-fluorouracil may provide improved performance and convenience over the multiple postoperative sub-conjunctival injections presently used.

In a further embodiment, a biodegradable layered fiber containing an angiogenesis-inhibiting agent, a corticosteroid, or other drugs, may be used to treat age-related macular degeneration with subretinal neovascularization. The drug eluting layered fiber may be placed in the sclera over the neovascular net or placed sub-retinal in the area of the neovascular net.

In other embodiments, compositions of the invention may be used in the treatment of cancer. The layered fiber may be implanted into the tissue surrounding the tumor or into the tumor tissue and tied in place to deliver local drug therapy. For example, sutures and related compositions containing an anticancer agent may be used to close incisions produced from invasive surgical procedures associated with cancer treatment, such as tumor removal, in particular from removal of tumors on or near the skin of the patient. Such tumors may result from various forms of skin cancer, such as basal cell carcinoma or melanoma. Such compositions may include a chemotherapeutic agent, an angiogenesis-inhibiting agent, a cell proliferation inhibitor, a radiosensitizer, and/or any other agent useful in the treatment of cancer.

For example, compounds that may be formulated in a subject composition for the treatment of cancer include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prednisolone); growth factor signal transduction kinase inhibitors; mitochondrial dysfunction inducers and caspase activators; chromatin disruptors.

The drug or agent delivered by the present system may also include but not be limited to steroids, such as corticosteroids, retinoids, NSAIDs, vitamin D3 and vitamin D3 analogs, antibiotics, and antiviral agents. Other suitable agents include enzymes, peptides and other large molecules.

Suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable antiviral agents include but are not limited to trifluridine, cidofovir, acyclovir, penciclovir, famciclovir, valcyclovir, gancyclovir, and docosanol.

Suitable human carbonic anhydrase inhibitors include but are not limited to methazoliamide, acetazolamide, and dorzolamide.

Suitable antiproliferative agents include but are not limited to 5-FU, taxol, daunorubicin, and mitomycin.

Suitable antibiotic (antimicrobial) agents include but are not limited to bacitracin, chlorhexidine, chlorhexidine digluconate, ciprofloxacin, clindamycin, erythromycin, gentamicin, levofloxacin, lomefloxacin, metronidazole, minocycline, moxifloxacin, mupirocin, neomycin, ofloxacin, polymyxin B, rifampicin, ruflozacin, tetracycline, tobramycin, triclosan, and vancomycin. The antiviral and antibacterial prodrugs of the invention may be used to treat appropriately responsive systemic infections.

The therapeutic agent (and/or an adjuvant) and polymer may associate in or on the layered fiber by means recognized by those of skill in the art such as, for example, electrostatic interaction, hydrogen bonding, hydrophobic interaction, formation of inclusion complexes with the inclusion hosts, or covalent attachment to the polymer, e.g., by a reversible attachment such as an ester or carbonate. In certain embodiments, the therapeutic agent and/or adjuvant may be covalently attached, optionally through a reversible linkage, to a moiety that forms an inclusion complex with the inclusion hosts, e.g., cyclodextrin. The degree of association may be determined by techniques known in the art including, for example, fluorescence studies, DNA mobility studies, light scattering, electron microscopy, and will vary depending upon the therapeutic agent. As a mode of delivery, for example, a therapeutic composition of the invention containing a material of the invention and DNA may be used to aid in transfection, i.e., the uptake of DNA into an animal (e.g., human) cell. (See, e.g., Boussif, O. Proceedings of the National Academy of Sciences, 92:7297-7301 (1995); and Zanta et al. Bioconjugate Chemistry, 8:839-844 (1997), the disclosures of which are incorporated herein by reference.)

For example, the agent may be dissolved, dispersed or suspended in the polymer of the layered fiber, whereupon it may leach out of the layered fiber and into surrounding fluid. In certain embodiments, the agent may rapidly escape from a thread after placement in a physiological system. Such rapid delivery may provide a large burst of drug to a targeted tissue thereby leading to a beneficial spike in drug level within the tissue.

As discussed above, it is preferred that at least one of the polymeric components of the thread be biocompatible such that it may dissolve when in contact with physiological fluid. In such embodiments, the rate at which such components dissolve will necessarily impact the rate of release of the agent. In certain embodiments, as the polymer components) erode or dissolve, the rate of release of the agent may increase. For example, in certain embodiments, less than about 10% of the polymeric component(s) may erode or dissolve over a period of about 6 hours. This may increase the rate of release of the agent by less than about 10% over that time. In certain embodiments, the polymeric components) may erode or dissolve more slowly (e.g. less than about 10% over a period of about 24 hours, or even over a period of multiple days, weeks, or even months). In certain embodiments, such erosion or dissolution may occur more rapidly (e.g. greater than about 10% over a period of about 6 hours, in certain embodiments even greater than 25% over a period of about 6 hours).

In addition, the solubility of the agent in the polymer may impact the rate of release of the agent from the layered fiber. In certain embodiments, the agent is soluble, moderately soluble, or even slightly soluble or very slightly soluble in the polymer. The agent's release rate from the layered fiber where an agent is soluble in the polymer may exceed the rate of release where the agent is only slightly or very slightly soluble in the polymer. In such embodiments, the rate of release of the agent from the thread may be controlled by the solubility of the agent in such surrounding fluid (i.e., the lower the solubility of the agent in the immediately surrounding fluid the lower its rate of release from the thread or fiber).

The release rate of the agent from the layered fiber may also be controlled by the ratio of the agent to the polymeric component of the monofilament (also referred to as the "drug loading"). By changing the drug loading, different release rate profiles can be obtained. Increasing the drug loading may increase the release rate. For a slower release profile, drug loading may be less than 10%, and preferably less than 5%. For a faster release profile, drug loading may be more than 10%, and preferably more than 20%, or even greater than 50%. The drug loading can be tuned and/or optimized for specific applications based on the fabrication method of the layered fiber.

The drug or agent may also be associated with a delivery system, e.g., a nucleic acid may be contained in a virus, or an agent may be carried within liposomes or microspheres, and the delivery system is dispersed through the polymeric components of the thread.

In addition additives, such as plasticizers, polymers, and cyclodextrin molecules, have been shown to modulate release of drugs from controlled release devices. Some or all of the layers in the described layered fiber could contain additives to modulate the release or mechanical properties of the layered fiber. These additives could also be used to increase drug loading or change the profile of release of the drug. Examples include water soluble additives such as sugars, salts, or polyethylene oxide) or polyethylene glycol) and derivatives and copolymers thereof. Plasticizers also change the mechanical properties of polymeric devices, softening the material and making it more flexible. Some biocompatible plasticizers (used in food and pharmaceutical applications) are benzyl benzoate, acetyl tributyl-, triethyl-, and trihexyl-citrate, and dibutyl sebacate.

Accordingly, in another embodiment of the invention the drug release, mechanical properties, and degradation of the layered fiber controlled release device is further controlled by the addition of various hydrophobic molecules. Hydrophobic plasticizers have been used to "soften" polymer devices and increase the rate of drug diffusion from the device. Hydrophobic ion pairing (HIP) has been used to slow drug release from polymeric microspheres. The idea behind HIP is to pair a water soluble charged drug with a hydrophobic molecule with the opposite charge. The pair has much lower solubility than the pure drug and should interact with a hydrophobic polymer to slow drug release from a device. HIP has also been used to enhance penetration of drugs into lipophilic cell layers, such as the skin and cornea.

In such an embodiment, the layered fiber device consists of a polymer, drug, and hydrophobic additive, and is used in applications that require a device to be anchored to a particular area or tissue and release a therapeutic agent over an extended period of time. The hydrophobic additive in accordance with the invention can alter either the mechanical properties, drug release rate, or both. The preferred physical embodiment of this device may be created using the method describe above, i.e., through a wet spinning method. However, in this embodiment the biodegradable polymer, drug, and hydrophobic additive are all dissolved in an organic solvent together and extruded into a coagulation bath filled. The coagulation fluid is miscible with the organic solvent but is a non-solvent for the polymer such that, as before, the polymer precipitates in the bath and traps the drug within its structure.

Accordingly, in one embodiment the additive interacts with the drug forming a hydrophobic ion pair, the resulting HIP can increase drug loading through increased organic solubility and drug retention during formation, a decreased initial burst of drug from the device, a change in the mechanical properties of the device by acting as a plasticizer, a change in the degradation rate of the device and corresponding drug release, and a change in the thermodynamic properties of the polymer device (glass transition temperature, melt temperature, etc.).

There are some notable limitations to the use of such HIP additives. Specifically, hydrophobic ion pairing can only be used on charged drugs, but many hydrophilic drugs are charged so there is a wide range of potential pairings. Since HIPs will be charged, they may be acidic or basic in solution. Since the degradation of polyesters (such as PLGA) is catalyzed by acids and polyesters are digested by bases, the addition of an HIP could be used to speed the rate of degradation. This in turn could be helpful to ensure complete drug release. Promising negatively charged ion pairing agents include, for example, octanoic acid, decanoic acid, hexanoic acid, and other long chain organic acids and their respective salts. Several positively charged candidates include, for example, octylamine, decylamine, and various other long chain amines. Charged adamantane derivatives, such as carboxylic acid and amine functionalized adamantane, may also be used as ion pairs due to the poor water solubility of adamantane.

In another embodiment, the plasticizer does not interact with the drug. In such an embodiment, the plasticizer can affect all of the parameters that the HIP does, but is unlikely to suppress burst or slow release. Moreover, in this embodiment of the invention the plasticizer need not be charged, but could be, depending on the desired rate of degradation of the device. Several exemplary non-interacting plasticizers include, for example, benzyl benzoate, acetyl tributyl-, triethyl-, and trihexyl-citrate, and dibutyl sebacate.

Another benefit of adding a plasticizer is the ability to stretch and narrow the strands of the monofilament to a desired diameter. Because a fiber without plasticizer may be too brittle, this could allow a much smaller device than possible without the plasticizer. If the layered fiber device is held in a stretched state for an extended period of time, eventually the device should retain that length/diameter without recoiling upon relaxation of the stretching stress. These thinner fibers could be useful individually or as part of a weave or braid that could release many drugs independently of each other or at different rates.

In order to optimize the mechanical and drug release profiles of the thread, polymers mixed with inclusion hosts as additives or bearing or including inclusions hosts in their backbone or side chains may also be employed. Cyclodextrins (CDs) are one example of such an inclusion host and may be employed with any of the polymers of the instant invention. Accordingly, in another embodiment of this invention pertains to the use of cyclodextrin to complex the HIP or plasticizer. Cyclodextrins are cyclic oligomers of glucose that have cup morphology with a hydrophilic exterior and hydrophobic interior. This shape allows cyclodextrins to include many kinds of molecules into their internal cavity. See, for example, Szejtli, *Cyclodextrins and Their Inclusion Complexes*; Akademiai Klado, Budapest, 1982; and Bender et al., *Cyclodextrin Chemistry*, Springer-Verlag, Berlin, 1978. Cyclodextrins are able to form inclusion complexes with an array of organic molecules including, for example, drugs, pesticides, herbicides, and agents of war. (See, Tenjarla et al., *J. Pharm. Sci.*, 87: 425-429 (1998); Zughul et al., *Pharm. Dev. Technol.*, 3: 43-53 (1998); and Albers et al., *Crit. Rev. Ther. Drug Carrier Syst.*, 12: 311-337 (1995), the disclosures of which are incorporated herein by reference.) CDs such as CD (Nagaraju et al., 1999; Chao et al., 2002), HPCD (Chao et al., 2004) and SBECD (Babu et al., 2004) have successfully been used to form individual complexes with ciprofloxacin, the disclosures of each of which are incorporated herein by reference. Cyclodextrin inclusion complexes have also been prepared with prednisolone. HPCD (Loftsson et al., 1994) and SBECD (Okimoto et al., 1998) have been used successfully to form inclusion complexes with prednisolone, and the disclosure of which are incorporated herein by reference.

The result of these studies shows that it is possible to tune the release and loading properties of the layered fiber device by using cyclodextrins to change the solubility or interaction properties of the HIP. Some examples of known potential ion pairs that could be complexed with cyclodextrin include hydrocarbon chains with -cyclodextrin and adamantane with -cyclodextrin.

Linear cyclodextrin-based polymers (CDPs) have previously been shown to have low toxicity both in vitro (in many different cell lines) and in vivo. (See Gonzalez et al. *Bioconjugate Chem* 10:1068-1074 (1999) and Hwang et al. Bioconjugate Chem 12(2):280-290 (2001), the disclosures of which are incorporated herein by reference.) The presently disclosed thread or fiber system includes biocompatible materials based on polymers that may bear or include cyclodextrin moieties. One or more linear CDPs of the same or different identities may be used as polymeric components in the thread.

The therapeutically active drug or agent may form an inclusion complex with the cyclodextrin moiety. Alternatively, a functional group or side group on the drug may form an inclusion complex with the cyclodextrin moiety. The specific interaction between the cyclodextrin and the drug may be determined by judicious selection of the cyclodextrin moiety. The interaction between the cyclodextrin and the drug may enhance the solubility properties of the drug. The drug may be more or less soluble in aqueous media on complexation with a cyclodextrin. The interaction between the cyclodextrin and the drug may be used to tune the controlled release of the drug from the thread or fiber. It has recently been shown that CD/drug complexes can be combined with polymers to provide for controlled release of the drug. (For example, see Loftsson, et al. *J. Drug Del. Sci. Tech.* 14: 35-43 (2004) and references therein or Yue, et al. *Biomaterials* 25:3743-3750 (2004), the disclosures of which are incorporated herein by reference.) In a preferred embodiment, the combination of CD/drug complexes when used with biodegradable polymers will provide the necessary mechanical and drug release properties to enable the use of thread for the controlled release of drugs.

In addition to cyclodextrins of various types and sizes, derivatives of these cyclodextrins such as methylated, alkylated, acylated, and benzylated cyclodextrins may be chosen to tune the drug delivery properties of the current system. Furthermore, unsaturated as well as homo-, seco-, and nor-derivatives of cyclodextrins may also be used. The present system also accommodates various substitution on the cyclodextrins or their derivatives. Such substitutions may improve the properties of the system, such as drug release profile, binding properties, solubility, and or bioavailability. While not intended to be limiting, some examples of -cyclodextrins are shown below:

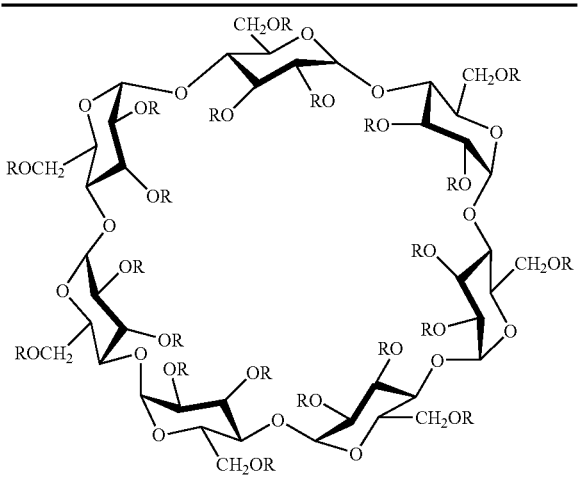

| | |
|---|---|
| Dimethylcyclodextrin (DMCD) | —$CH_3$ or —H |
| Trimethylcyclodextrin (TMCD) | —$CH_3$ |
| Randomly methylatedcyclodextrin (RMCD) | —$CH_3$ or —H |
| Hydroxyethylcyclodextrin (HECD) | —$CH_2CH_2OH$ or —H |
| 2-Hydroxypropylcyclodextrin (HPCD) | —$CH_2CHOHCH_3$ or —H |
| 3-Hydroxypropylcyclodextrin (3HPCD) | —$CH_2CH_2CH_2OH$ or —H |
| 2,3-Dihydroxypropylcyclodextrin (DHPCD) | —$CH_2CHOHCH_2OH$ or —H |
| 2-Hydroxyisobutylcyclodextrin (HIBCD) | —$CH_2C(CH_3)_2OH$ or — |
| Sulfobutylethercyclodextrin (SBECD) | —$(CH_2)_4SO_3Na$ or —H |
| Glucosylcyclodextrin ($G_1CD$) | -glucosyl or —H |
| Maltosylcyclodextrin ($G_2CD$) | -maltosyl or —H |

In certain embodiments of the present invention, a polymer bears both inclusion hosts and inclusion guests, and thus crosslinks with itself by forming inclusion complexes between hosts and guests on the same polymer chain and/or between hosts and guests on adjacent polymer chains. Conditions under which the crosslinking is performed will influence the balance between these two types of inclusion complexes. For example, performing the complexation at high dilution will favor the formation of intramolecular complexes, while performing the complexation at high concentrations will favor the formation of intermolecular complexes, including, in some cases, catenane- and rotaxane-type structures. In certain such embodiments, a high degree of intermolecular interaction increases the rigidity, melting point, and strength of the material.

For purposes of the present application, layered fiber polymers 'incorporate' inclusion hosts, such as cyclodextrin moieties, by having inclusion hosts within the polymer chain, e.g., removing inclusion hosts from the layered fiber polymer would require severing the polymer chain. Examples of such polymers are the linear cyclodextrin-based polymers referred to above. Polymers that 'bear' cyclodextrin moieties have a polymer chain to which inclusion hosts are attached, e.g., inclusion hosts are appended to a distinct polymer chain. Polyethylenimine-CD polymers are examples of this type of polymer. Polymers that 'include' inclusion hosts are those polymers that 'bear' or 'incorporate', or both bear and incorporate, inclusion hosts, or otherwise have covalently bound inclusion hosts as part of the polymer chain. Any polymer that includes inclusion hosts can be employed in the present application. In certain embodiments, a polymer that incorporates inclusion hosts is a linear (i.e., non-branched) polymer. In certain embodiments, inclusion hosts, e.g., incorporated into or borne on the polymer, are regularly spaced throughout or along the polymer.

The physical and drug release properties of the resultant layered fiber or thread can be varied by selecting moieties or drugs that form inclusion complexes of varying strength; the stronger the complex, the more durable and stable the resulting system and the slower the release of therapeutic agent. Additionally, the physical and drug release properties of the instant system may be tuned by covalently attaching the drug or agent to the polymeric components of the layered thread or fiber system. Such attachment may utilize linking moieties. Such linking moieties may be cleaved under biological and/or physiological conditions, thereby releasing the drug or agent. Alternatively, such linking moieties can be used to connect two or more drugs or agents of the same or different identities, while remaining non-covalently associated with the polymer. The linking moieties can also be used to crosslink polymers within the monofilament or polymers within different monofilaments. As such, linking moieties can be used to link two or more layered fibers in a thread. Linking moieties bearing two or more such drug moieties may increase the strength and rigidity of the material by increasing the degree of crosslinking as well as increasing the proportion of linking moieties to polymer mass. The drug release profile of the system may also be varied in this manner as multiple therapeutic agents may be tethered or linked together in one molecule. Following release of such a molecule from the polymeric components of the thread, the tether or linking moiety can be cleaved under physiological conditions releasing multiple therapeutic agents. Additionally, varying the number of binding therapeutic agents will alter the binding capacity, and hence the drug release profile. Physical properties of the monofilaments can also be varied by altering the flexibility of the linking moieties themselves, or by altering the flexibility of linkers within the polymer itself.

Furthermore, the in vivo properties of the layered fiber polymer system may be varied by using bonds in the layered fiber polymer that are labile under physiological conditions. For example, the polymer strands, the crosslinking moieties, or both, may comprise bonds, such as ester and peptide bonds that are labile under physiological conditions. After placement in a physiological environment, these bonds will gradually begin to cleave, resulting in a gradual degradation and loss of structural integrity. A wide spectrum of properties can be achieved by varying the frequency of such bonds in a polymer strand, by combining labile and resistant crosslinking moieties in varying proportions, or by selecting different labile bonds with differing strengths. For example a peptide bond is generally more resistant to cleavage than an ester bond, which is in turn less labile than a thioester bond.

Inclusion hosts, such as the cyclodextrins discussed above, can be used with the layered fiber polymeric components of the thread through covalent bonds. These hosts can be directly on the polymer backbone or on side chains of the layered fiber. Alternatively, the hosts, such as one or more types of cyclodextrins, can be admixed into the layered-fiber polymer blend. A combination of covalently bound hosts and non-covalently bound hosts can also be used, wherein the hosts may be the same or different throughout the thread or fiber system. Furthermore, the layered fiber polymer system may be made up of predominantly or entirely of cyclodextrins, of which there may be one or more types. Therapeutic agents, viruses, adjuvants, and the like, which can be formulated with the layered fiber polymer by forming inclusion complexes, can also be formulated by simple admixture or encapsulation, without forming inclusion complexes, as is well known in the art for ordinary biocompatible polymers.

Compounds increasing the therapeutic utility of the material, such as signaling peptides, other moieties facilitating cell migration, or adjuvants, may be incorporated-into the polymer by conjugating an inclusion complex guest to the entity of interest and including the conjugate in the layered fiber polymer. The conjugate may be included before, during or after the formation of the layered fiber polymer or during or after the formation of the thread from the layered fiber polymer. Therapeutic compounds may also be included in this fashion, preferably where the attachment between the drug and the inclusion guest/host is labile under physiological conditions, such as an ester bond. See, e.g., U.S. Patent Application Publication Nos. 2003/0008818 and 2003/0017972, the disclosures of which are incorporated herein by reference.

Additionally, those of skill in the art will recognize that this concept can naturally be extended to layered fiber polymers bearing or incorporating inclusion hosts other than cyclodextrins, in conjunction with linking moieties that bear inclusion guests that form inclusion complexes with those inclusion hosts, or, alternatively, polymers that bear inclusion guests in conjunction with linking moieties that bear or include inclusion hosts that form inclusion complexes with those inclusion guests. Examples of inclusion hosts other than cyclodextrins and related cycloamyloses include perhydrotriphenylene (which forms inclusion complexes with polyethylene), urea/thiourea (which form inclusion complexes with fatty acids and related molecules as described in U.S. Pat. Nos. 4,776,984, 5,106,542, and 4,170,601), cyclophanes (such as those described in U.S. Pat. No. 4,116,955), and those described in U.S. Pat. Nos. 4,841,081, 4,367,072, and 4,898,654, all of which are hereby incorporated by reference in their entireties.

The foregoing factors are illustrative only. The skilled artisan will readily appreciate that any other property of the inventive system may be the limiting factor in the agent's release rate from the system.

The layered fiber or thread disclosed herein, in addition to being potentially biodegradable, may also incorporate a biodegradable coating. Coatings containing caprolactone for synthetic absorbable sutures are well known, see for example U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,133,739; and 5,352,515, the disclosures of each of which are incorporated herein by reference. Coatings containing esters of fatty acids are also known; see for example U.S. Pat. Nos. 5,032,638; 4,711,241; 4,705,820; and 4,027,676, the disclosures of which are incorporated herein by reference. Advantages of using coated layered fiber or thread include reduction in the incidence of tissue trauma (tissue drag) as compared to use of uncoated braided multifilament thread. Another important feature of a coating is its ability to enhance the thread's handling characteristics, such as surgeon's throw, lubricity, knot run down and/or knot security. The coating of the layered fiber or thread may also incorporate one or more drugs or therapeutic agents to provide an initial burst or surge of therapeutically effective drug to the targeted tissue, followed by sustained release of the drug or agent from the degradation of the remainder of the layered fiber polymer system. Such a drug may be dissolved in the coating in similar methods as described herein for drugs dissolved in the thread. Similarly, the coating may be composed of materials that may be the same or different from that of the thread or fiber system. Numerous biodegradable surface coated sutures have been FDA approved and are currently in use. For example, U.S. Pat. No. 5,716,376, all of which may be adapted to the present invention and the disclosure of which is incorporated herein by reference, describes a copolymer bioabsorbable coating.

Although many applications are possible for the layered fibers of the current invention, one primary application of this technology is where a device needs to be anchored or maintain physical structure at the same time that it releases drug. An example of this is a layered fiber that is implanted in the conjunctiva after eye surgery for sustained release of antibiotics or steroids. Drug delivery to the eye is of particular concern as the eye is a sensitive organ that often requires extended medication. Currently the most common delivery of therapeutic to the eye is in drop form, but since drops rely on patients to self-administer, they are often taken improperly or not at all. Since the eye is sensitive, microspheres and particles are of limited use as they might exacerbate any inflammation. An implant would we ideal, but many of the previously devised implants suffer from setbacks including high rigidity that gives a foreign body sensation in the eye and the inability to stay in the eye without fixation by some sort of suturing method. For this purpose, it would be ideal to have a self-anchored device that is soft enough to conform to the natural contours and motions of the eye. Moreover, since the eye and surrounding tissue moves, and since a device implanted fully under the conjunctiva will not release most of its drug load into the tear film, a device that maintains strength during the entire release of drug is desired.

Another application of this invention is for a wound packing where you can have several of these devices or a device with many different layers together releasing drug and changing mechanical properties, all at different rates. The overall result will be a packing that releases drug for an extended period of time at a relatively constant rate and slowly degrades and loses mass over a long time. This is beneficial, as compared to a device with a single degradation rate, as the different layers can release drugs at different rates even if drug release is degradation controlled. Some of the layers can last a long time for structural integrity of the packing. Acid levels in the cavity will be kept at a minimum since only some of the packing will be heavily degrading at any given point (and releasing acid as polyesters often do).

Another possible application of this technology is in the area of drug releasing sutures. Since a wet processed, amorphous fiber probably would not have the strength that a suture requires, it would be necessary to have at least one layer of the fiber be of a structurally strong polymer material, or that other types of fiber would need to be braided together with the layered fiber of the invention. For example, several melt-spun, highly crystalline, strong fibers of small diameter could be woven with several weaker, more flexible drug releasing layered fibers.

DEFINITIONS

For convenience, before further description of the present invention, certain terms employed in the specification, examples, and appended claims are collected here. These definitions should be read in light of the remainder of the disclosure and understood as by a person of skill in the art.

The term "active" as used herein means biologically, therapeutically or pharmacologically active.

An 'adjuvant', as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The term "agent" as used herein is synonymous with "at least one agent," "compound," or "at least one compound," and means at least one drug or codrug, or a prodrug thereof. In certain embodiments, the agent may be at least one low-solubility codrug, or a prodrug thereof. In certain embodiments the codrug, or prodrug thereof, is designed to have low solubility in either the core, the biological fluid or both. In certain embodiments, the agent may be a protein, peptide, or a pegylated agent. In still other embodiments, the term "agent" refers to a plurality of drugs, proteins, peptides, etc. In certain embodiments the agent may be in granular form. In certain embodiments, the agent may be combined with a pharmaceutically acceptable carrier. In certain embodiments, the agent is in liquid form.

The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction, in the host. It is not necessary that any subject composition have a purity of 100% to be deemed biocompatible. Hence, a subject composition may comprise 99%, 98%, 97%, 96%, 95%, 90%, 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 μL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is synonymous with "bioerodible" and is art-recognized. It includes polymers, compositions and formulations, such as those described herein, that degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, biodegradation may occur by enzymatic mediation, degradation in the presence of water and/or other chemical species in the body, or both.

As used herein, the term "biodegradation" encompasses both general types of biodegradation. The degradation rate of a biodegradable polymer often depends in part on a variety of factors, including the chemical identity of the linkage responsible for any degradation, the molecular weight crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any biodegradable polymer is usually slower.

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of materials) incorporated therein.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent. Sustained release will vary in certain embodiments as described in greater detail below.

An "effective amount" or "therapeutically effective amount" of an agent, with respect to methods of treatment, refers to an amount of the agent in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose. A therapeutically effective amount, as recognized by those of skill in the art, will be determined on a case by case basis. Factors to be considered include, but are not limited to, the disorder to be treated and the physical characteristics of the one suffering from the disorder.

As used herein, the term "$EC_{50}$" means the concentration of a drug that produces 50% of its maximum response or effect.

As used herein, the term "$ED_{50}$" means the dose of a drug that produces 50% of its maximum response or effect.

The terms "encapsulated" is art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction) physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions) encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "fiber" as used herein, refers to a slender, elongated, wire-like object or structure. "Monofilament" and "fiber" are used interchangeably herein. A fiber of the present invention refers to a biodegradable drug-eluting multi-layered polymer with a slender, elongated shape. In certain embodiments, "fiber" as used herein, also includes one or more sections. Fibers or monofilaments may possess a ribbon configuration comprising a flexible, flat and/or thin profile or shape. In some embodiments, "fiber" as used herein, also includes one or tube configurations; that is, elongated structures with a hollow core at their centers, for example, tube-like structures. As such, a fiber of the present invention may also refer to a biodegradable drug-eluting layered polymer tube, i.e., a fiber fashioned to include a hollow portion in its center, such as a longitudinally extending through lumen. In certain embodiments, a fiber comprises s that have different physical characteristics and or configurations, e.g., ribbon portions, hollow portions, bulb portions, or different chemical characteristics, e.g., polymers or polymer blends, additives, or the like.

The term "$IC_{50}$" means the dose of a drug that inhibits a biological activity by 50%.

The term "$LD_{50}$" means the dose of a drug that is lethal in 50% of test subjects.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material suitable for formulating a medical or cosmetic composition. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. (See, for example, *J. Pharm. Sci.* 66: 1-19 (1977), the disclosure of which is incorporated herein by reference.)

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The phrase "protecting group" or "protective group" as used herein means a temporary substituent that protects a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2$^{nd}$ ed.; Wiley: New York, 1991), the disclosure of which is incorporated herein by reference.

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The term "therapeutic index" refers to the therapeutic index of a drug defined as $LD_{50}/ED_{50}$.

The term "thread" as used herein includes one or more fibers or monofilaments, at least one of which may be a biodegradable drug-containing layered fiber of the present invention. When a thread comprises more than one fiber, the fibers may be twisted, interwoven, spun, tufted, or otherwise braided together to form the thread. Thus, threads of the present invention include monofilaments, braided polyfilaments, and other associations of multiple fibers. The systems and methods described herein are amenable to the use of the present threads and/or fibers, unless specifically stated to the contrary. For example, in some embodiments, threads may also possess one or more ribbon configurations and/or tube configurations.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

Exemplary Embodiments

The person skilled in the art will recognize that additional embodiments according to the invention are contemplated as being within the scope of the foregoing generic disclosure, and no disclaimer is in any way intended by the foregoing, non-limiting examples.

One embodiment of the present systems relates to a biodegradable polymeric layered fiber or thread that contains single or multiple therapeutic agents or drugs within the layers of the thread or fiber to provide a drug-eluting suture. Such a system may be employed to treat a number of different disorders, including the treatment of ocular diseases and disorders. A suture made of such a material may provide sustained release of one or more therapeutic agents or drugs over the lifetime of the suture as it degrades. Such a system may provide high and/or stable intraocular levels of therapeutic agent or drug in contrast to methods of treatment employing topical drops. In some embodiments, drug-eluting sutures may decrease and/or eliminate the need to employ eye drop treatments after surgeries. Such instant methods may reduce and/or eliminate patient compliance issues.

Figure 5A:
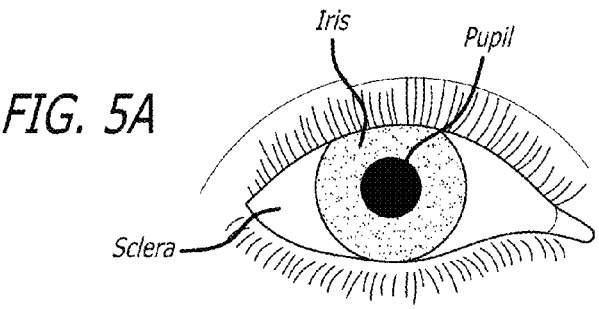
FIGS. 5a and 5b: Provide schematic illustrations of the anatomy of the eye.
Figure 5B:
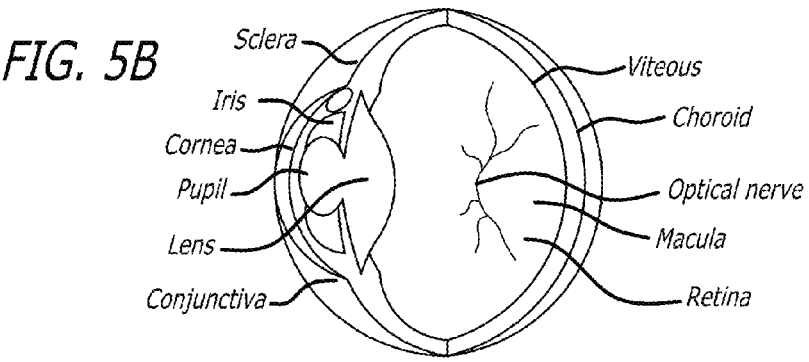
Figure 6:
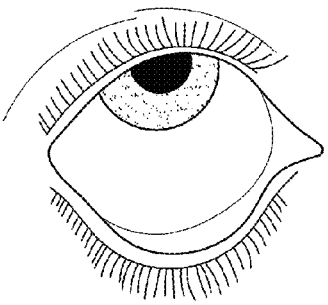
FIG. 6: Provides a photograph illustrating the lower lid conjunctival fornix.

The drug-eluting suture may be attached to a surgical needle. In certain embodiments, the needle can be used to penetrate the conjunctiva and to deliver the attached drug-eluting suture into the sub-conjunctival space. FIGS. 5*a* and 5*b* present schematic illustrations of the anatomy of the eye, highlighting the conjunctiva. Once the biodegradable suture is implanted under the conjunctiva, the suture may be cut close to the surface of the conjunctiva, so only a small suture tail remains. In certain embodiments, the suture is placed in the conjunctival fornix (junction between the posterior eyelid and the eyeball) where it is covered by the eyelid. FIG. 6 presents a photograph illustrating the lower lid conjuctival fornix. As the suture degrades, one or more therapeutic agents or drugs may be released into the sub-conjunctival space and into the fornix to mix with the tear film and subsequently into the eye. By placing the suture under the conjunctiva, foreign body sensation may be reduced or eliminated, and the suture will not migrate or dislodge.

The drug-eluting sutures of the current invention may be useful in many instances for methods of treatment, such as ocular treatment. Sutures and/or one or more variants of the instant invention may have wide applicability and be useful for virtually all ophthalmic surgery. In one embodiment, the sutures may be employed with post-operative antibiotics and corticosteroids. The conjunctiva may be anesthetized for a primary surgery. The use of sutures of the instant invention may employ instruments available in standard surgical facilities and operating rooms. The methods of treatment comprising the instant sutures may lessen or eliminate the need for treatment with eye drops following surgical procedures. In instances where the current method substitutes for treatment with eye drops, the convenience to the patient and therefore patient compliance may increase, particularly in cases where the patient is resistant to applying eye drops following surgery.

For example, an illustrative clinical application of the present suture system is treatment of a postoperative cataract patient. Drops are routinely used after cataract surgery: corticosteroids are used postoperatively for 3 to 4 weeks and antibiotics for one to two weeks. A biodegradable suture of the present invention comprising the present layered multi-component fibers or threads containing corticosteroid and antibiotic may be implanted in the sub-conjunctival space at the time of cataract surgery to provide sustained postoperative drug release. Differences in duration and rate of drug delivery may be modulated by fiber size, shape and polymeric/chemical make-up. Such a sustained drug release has a distinct advantage over the usual postoperative drops, because the implant drug delivery does not depend on patient compliance and systemic doses are avoided.

In another illustrative example, drug-containing sutures of the present system, such as corticosteroid sutures, may be imbedded in lesions such as eyelid chalazion to reduce inflammation, or hemangiomas to reduce vascular mass.

The instant sutures may also provide methods of antibiotic treatment to patients suffering from corneal ulcers. In such embodiments, the instant polymeric suture may provide sustained levels of antibiotic, which may be important as the cornea is avascular. Such instant methods may diminish and/or replace repeated, often hourly, application of eye drops, especially in instances where application of drops is painful to the patient.

The instant sutures may also provide methods of treatment to patients requiring corticosteroid treatment of uveitis and scleritis. In such embodiments, the instant polymeric suture may facilitate long-term treatment and/or treatment when patients are asymptomatic. The instant methods and systems may be used to taper the dose of the therapeutic agent or drug employed.

The instant sutures may also provide methods of antibiotic treatment to patients requiring treatment for glaucoma. In such embodiments, the instant polymeric suture may facilitate long-term treatment and/or treatment when patients are asymptomatic. Often sufferers of glaucoma are elderly and may have difficulty administering treatment by eye drops; the instant methods will facilitate treatment by reducing and/or obviating the need for drops. The instant system can deliver controlled amounts of therapeutic agent or drug to facilitate compliance. The instant methods and systems may be used to taper the dose of the therapeutic agent or drug employed.

The instant sutures may also provide methods of treatment to suffering from vernal conjunctivitis. In such embodiments, the instant polymeric suture may facilitate long-term treatment and/or treatment when patients are asymptomatic.

The drug-eluting polymeric layered fibers of the present invention may contain any of the therapeutic agents or drugs described herein. In certain embodiments, the polymeric sutures for ocular treatment may contain antibiotics, such as ciprofloxacin. In certain embodiments, the polymeric sutures for ocular treatment may contain steroids, such as the corticosteroid prednisolone. In some embodiments the polymeric sutures for ocular treatment may contain more than one therapeutic agents or drugs in combination. Such combinations may employ agents of the same or of different types. For example, the antibiotic ciprofloxacin and the corticosteroid prednisolone may be used in combination.

Another embodiment of the present systems relates to a polymeric layered fiber that contains single or multiple therapeutic agents or drugs for the treatment of diseases or inflammations of the mouth, in particular those of the teeth and gums, such as gingivitis or periodontitis. In one embodiment, the layered fiber contains one or more drugs or agents, such as an antibiotic, and is implanted into the periodontal tissue to provide local drug delivery as the layered fiber degrades. The layered fiber may be placed in the subgingival tissues. In some embodiments, the layered fiber provides sustained local delivery of the agent resulting in sustained elevated agent concentrations in the crevicular fluid; in other embodiments, the layered fiber provides an initial burst of the agent. In certain embodiments, the antibiotic agent is chlorhexidine, metronidazole, minocycline, triclosan, or tetracycline.

Treatment of periodontitis with the present system may be more effective than traditional scaling, root planing, and antibiotic mouthrinse methods. Additionally, the layered fibers or threads of the invention can be used in combination (i.e. in adjunctive therapy) with other suitable periodontal treatment methods, such as scaling, root planing, and antibiotic mouthrinse methods. The present system may also provide advantages and/or improved efficacy over other agent-releasing implants, such as fibers, chips and/or gels. For example, the present layered fibers or threads may provide sustained local delivery of a therapeutic agent to the periodontal tissues, reducing the frequency of treatment when compared with other implantation or treatment methods. The current system may also prove effective for treatment of periodontitis where other treatments, such as scaling, root planing, antibiotic implants, or combinations thereof, have proven ineffective; for example, the layered fibers or threads of the invention may prove effective for treating periodontitis in a patient that has previously not responded to other treatments. Periodontal treatment by the present invention may enhance surface demineralization, delay pellicle and plaque formation, promote anti-collagenase activity, reduce periodontal pocket depth, and reduce bleeding on probing.

In another embodiment, the present invention relates to the use of therapeutic agent-containing layered fibers or threads as biodegradable nerve guide tubes. Layered fibers or threads of the invention may contain a hollow core, e.g., a longitudinally extending lumen, to provide a tube-like structure. Such a tube may be used as a guide to induce nerve growth between ends of a severed nerve and/or to connect transected axons. Thus, nerve guide tubes or nerve guides of the present invention can be used to repair peripheral nerve damage and/or to reduce or eliminate neuropathic pain that may result from such damage. Nerve guides of the present invention may be inert and biocompatible, thin, flexible, of suitable mechanical properties, and beneficial to healing and/or regeneration. In certain embodiments, the nerve guides are biodegradable or bioresorbable. In some embodiments, the nerve guides are able to inhibit pathological processes. In some embodiments, the nerve guides are translucent.

Layered fibers of the present invention possessing a tube-like structure or configuration may be anywhere from a few millimeters long to several centimeters long or longer. The internal diameter of the tubes may be approximately 5 mm, 2 mm, 1 mm, 0.5 mm, 0.1 mm or less, preferably less than about 1 mm. The wall of the tube may be approximately 2 mm, 1 mm, 0.5 mm, 0.1 mm, 0.01 mm or less, preferably less than about 0.1 mm.

In certain embodiments, the wall of the hollow layered fiber, e.g., the nerve guide, is loaded with one or more therapeutic agents, such as neurotrophic factors, e.g., nerve growth factor (NGF), brain-derived neurotrophic factor (BDNF), and other factors present in regenerating peripheral nerves. In some embodiments, one or more optional additives and/or carrier molecules, such as a cyclodextrin, may be loaded into the layered fiber. In some embodiments, the wall of the hollow layered fiber is loaded with one or more nerve growth inducing agents. Such agents may be a small molecules, such as sabeluzole, or inosine, or a larger biological molecule, such as human nerve growth factor. Examples of nerve growth factors suitable in the present invention include proteins and nucleotides. The present system also contemplates low temperature methods of nerve guide tube layered fiber production, such as wet-extrusion and dip-coating, which may be compatible with the incorporation of biological nerve growth factors, such as proteins and nucleotides. The nerve guide tubes may also include biodegradable drug delivery agents, such as microspheres or nano-fibers, which may be included in the walls of the layered fiber or inside the hollow core of the layered fiber. The nerve guide tubes may induce nerve growth by both the physical presence of a tube and by the controlled release of nerve growth factors. Once the nerve has regenerated, the tube itself may biodegrade, eliminating the need to remove the tube. Alternatively, the tube may be easily removed prior to its biodegradation; thus implantation of the guide tube may be reversible.

In some embodiments, the hollow core of the nerve guides may be filled with a drug-containing and/or releasing medium. For example, the tubes may contain a gel or hydrogel, such as collagen containing a therapeutic agent, such as a growth factor. In certain embodiments, the nerve guides are filled with an isotropic collagen gel or a magnetically aligned hydrated gel of type I collagen. The nerve guides may also contain microspheres or beads which contain and release one or more therapeutic agents, such as NGF. In certain embodiments, the nerve guides may contain NGF-secreting cells, such as Schwann cells. Additionally, the medium contained within the nerve guide may also release one or more additives and/or carrier molecules, such as cyclodextrins, which may facilitate the loading of the agent and/or its delivery from the nerve guide.

Layered fibers of the present invention that are used as nerve guides may possess any of the features of other fibers described herein. For example, nerve guides may comprise a variety of biodegradable polymers, such as polyphosphoester, polylactic acid (PLA), polycaprolactone (PCL), polyglycolic acid (PGA), polydioxanone (PDO), or co-polymers thereof, such as PLA-PCL, PGA-PCL, PCL-PDO, etc. Other examples of polymers suitable for use in fibers of the present invention, particularly for nerve guides, include poly(1,3-trimethylene carbonate-caprolactone) and poly(bis(hydroxyethyl)terephthalate-ethyl ortho-phosphorylate/terephthaloyl chloride). The instant nerve guides may also include other materials such as metals, silicone, rubbers, and both biodegradable and non-biodegradable synthetic polymers.

Examples of nerve guide tubes contemplated by the present invention include those described in U.S. Pat. No. 3,833,002; Rosner, et al. *Ann. Biomed. Eng.* 2003, 31, 1383-1401 and Verreck et al. *Biomaterials,* 2005, 26, 1307-1315; the entire contents of which are hereby incorporated by reference.

In another embodiment, layered fibers or threads of the present invention having a tube configuration may be employed as a stent, i.e. a tube like device to create patency, to hold anatomic tubes open. The instant stents may have certain the features from other fibers described herein. For example, the stents may elute one or more drugs or therapeutic agents and/or contain one or more additives or carrier molecules, such as cyclodextrins. The stents may have one or more biodegradable portions. Additionally, the present stents may include one or more non-biodegradable portions, for example, made from traditional stent materials, such as stainless steel or other metals or plastics. The present stents may be installed by any suitable means, for example, by those used for traditional stents. In certain embodiments, the present stents may also be readily removed from the patient, i.e., their implantation is reversible.

As such, a layered fiber with a tube configuration can be implanted in a patient and serve as a drug-eluting stent to hold a vessel or other anatomical tube open. Alternatively, layered fibers of the present invention may be woven or otherwise configured to form a mesh tube. In certain such embodiments, where the rigidity of the stent is responsible for maintaining a passageway or other lumen, the fibers used may be stiffer than those used in circumstances where flexibility is desired, such as with a suture that needs to be threaded through tissue. Rigidity may be increased by changing the polymer content, the manufacturing and/or curing technique, the diameter of the layered fiber, or the shape of the layered fiber (e.g., a more circular cross-section, a tubular configuration, or certain surface modifications may impart increased rigidity in the context of a mesh).

In one embodiment, a stent of the invention is loaded with the therapeutic agent heparin and employed as a coronary artery stent to hold the vessel open and elute heparin to prevent clotting. In this embodiment, a high local concentration of heparin may be delivered without causing significant systemic anticoagulation. In certain embodiments, ducts of glands may be kept open with a stent that contains an anti-scarring drug. The stents, e.g., biodegradable drug-eluting tubes, may be useful in neurological surgery, vascular surgery, urological surgery, gynological surgery, ear nose and throat surgery, or general surgery for example, whether to maintain the patency of a lumen, to permit drainage from a site of fluid build-up, or to act as a shunt through a tissue barrier. In specific embodiments, the present stents may be employed in, but not limited to, general surgery (bile system and bowel), urology (vas deferens, ureter and urethra) or gynecology (fallopian tube).

Stents of the present invention may be used in applications where traditional stents may be used. The instant stents may also contain drugs or therapeutic agents that are used in traditional stents or that may be coated on traditional stents. For example, sirolimus, paclitaxel, and estradiol, may be used with the present stents. Drugs and therapeutic agents used with the present stents may complex with one or more additives or carrier molecules, such as cyclodextrins. For example, paclitaxel may be used and complexed with one or more cyclodextrins.

Layered fiber of the present invention used as stents may contain one or more therapeutic agents throughout the body of the stent. Accordingly, the present stents may possess improved pharmacological properties over traditional drug-coated stents. For example, the present stents may provide increased delivery of drug and delivery over a longer duration than traditional drug-coated stents. The present stents may also provide more controllable delivery profiles. As with other fibers described herein, the pharmacological properties of the stents can be optimized and tuned for specific applications.

In another embodiment, a layered fiber with a tube configuration as disclosed herein may be used as a sheath to surround a traditional stent. For example, a layered fiber with a tube configuration may be threaded onto a traditional stent, providing a biodegradable drug-eluting layer. In some instances, the layered fiber may be formed directly on the stent during preparation of the fiber; thus providing a biodegradable drug-eluting coating on the stent.

The instant layered threads or fibers may also provide methods of treatment to patients suffering from cancer. In such embodiments, the instant polymeric thread or layered fiber may deliver controlled and/or sustained drug release The drug-eluting polymeric threads or layered fibers of the present invention may employ any polymer, or combination of polymers, described herein in addition to those appreciated by those of skill in the art. In certain embodiments, the polymeric threads or layered fibers employ poly(lactide-co-glycolide) (PLGA).

In certain embodiments, the layered fiber, threads, and/or sutures of the present invention may employ cyclodextrins (CDs) to improve the pharmacological properties of the instant systems. CDs may also be used in embodiments for treating ocular diseases or disorders, periodontal and subgingival diseases or disorders, and in nerve guide tubes. The use of CDs may improve the solubility and/or bioavailability of the therapeutic agents or drugs of the instant systems and methods. For example, certain embodiments employ ophthalmic formulations of ciprofloxacin containing hydroxypropyl-cyclodextrin (HPCD, a FDA approved CD). Such complexes form inclusion complexes, and exhibit better stability, biological activity and ocular tolerance compared to ciprofloxacin alone. (See, e.g., Nijhawan and Agarwal, 2003, the disclosure of which is incorporated herein by reference.) Also, these CD-containing solutions may not lead to ocular ciprofloxacin precipitation because of the greatly increased solubility of the inclusion complexes over the drug alone. Corneal ciprofloxacin precipitation may delay epithelial healing. (See, e.g., Wilhelmus and Abshire, 2003, the disclosure of which is incorporated herein by reference.) In some embodiments, CD:drug inclusion complexes can be formed at ambient temperature and collected. In certain embodiments, the therapeutic agent or drug is interacting with the interior of the CD cup, and the exterior of the CD cup may provide the interface to the polymer. In these embodiments, a three-component system (polymer, CD, drug) can be combined in solution for wet-spinning to occur, for formation of the drug-eluting fiber. Since CDs can form inclusion complexes with many different drugs (over 30 different products worldwide; Davis and Brewster, 2004, the disclosure of which is incorporated herein by reference) the instant methods and systems have general application to drug delivery.

While certain embodiments contemplate the use of a thread or layered fiber comprising cyclodextrin complexes and a single drug, such as an antibiotic or a corticosteroid, other embodiments may contemplate a suture that employs multiple drug combinations, for example, a suture that comprises CD complexes, an antibiotic, and a corticosteroid. To illustrate, some embodiments may comprise TobraDex®, an ophthalmic ointment that contains an antibiotic (tobramycin), and a corticosteroid (dexamethasone) to suppress an inflammatory response. The combination of an antibiotic and a corticosteroid may be contained in the drug-eluting suture by first preparing inclusion complexes of the two drugs with CDs and then adding both to the polymer for wet-spinning of the fiber. In some embodiments, the drugs are FDA approved. In yet further embodiments, all components of the drug-eluting suture have FDA approval.

Finally, in certain embodiments, the layered fiber, threads, and/or sutures of the present invention may employ hydrophobic plasticizers to improve the pharmacological properties of the instant systems. The use of hydrophobic ion pairing (HIP) can provide additional control over drug release, mechanical properties, and degradation of the layered fiber controlled release device. For example, HIP has been used to enhance penetration of drugs into lipophilic cell layers, such as the skin and cornea.

EXAMPLES

Example 1

Wet-Spinning of Multi-Component Device

Figure 7:
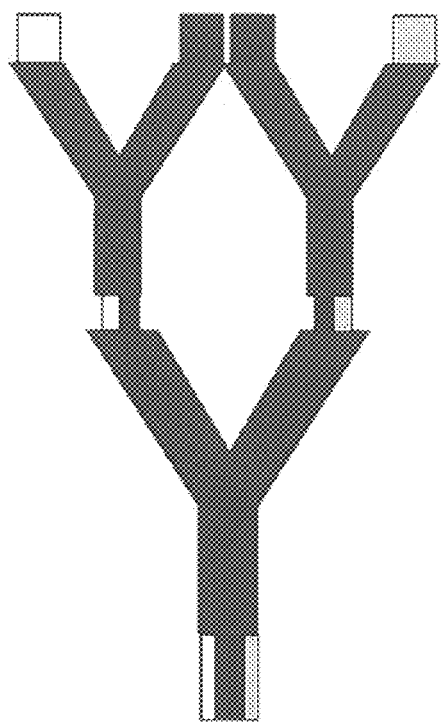
FIG. 7: Provides a schematic of a 4-component device made by adding layers of connectors and input streams.

In a first example, two component layered fiber devices were prepared from two solutions containing polymer and drug dissolved in a common solvent. In several of the following examples, the drug levofloxacin and the polymer PLGA were dissolved in dimethyl sulfoxide (DMSO). Polycaprolactone (PCL) dissolved in acetone was also used. Approximately 1 ml of each polymer solution was loaded into a 5 ml glass syringe. The outlets of the syringes were connected to a 22 gauge Y-connector by Teflon tubing. The polymer was extruded through the tubes into the connector (FIG. 3a) by a syringe pump. The outlet of the connector was placed in a coagulation bath (containing water in this case). The stream of coagulated filament was passed through the bath under guide posts and taken up onto a rotating bobbin. This scheme is outlined in FIG. 3b. Although only a two layer fiber device was made using this scheme, a higher order multi-component device could be created by joining multiple steams through the same connectors as shown in FIG. 7.

Example 2

Two Component Filament with Single Drug in Two Forms

Figure 8:
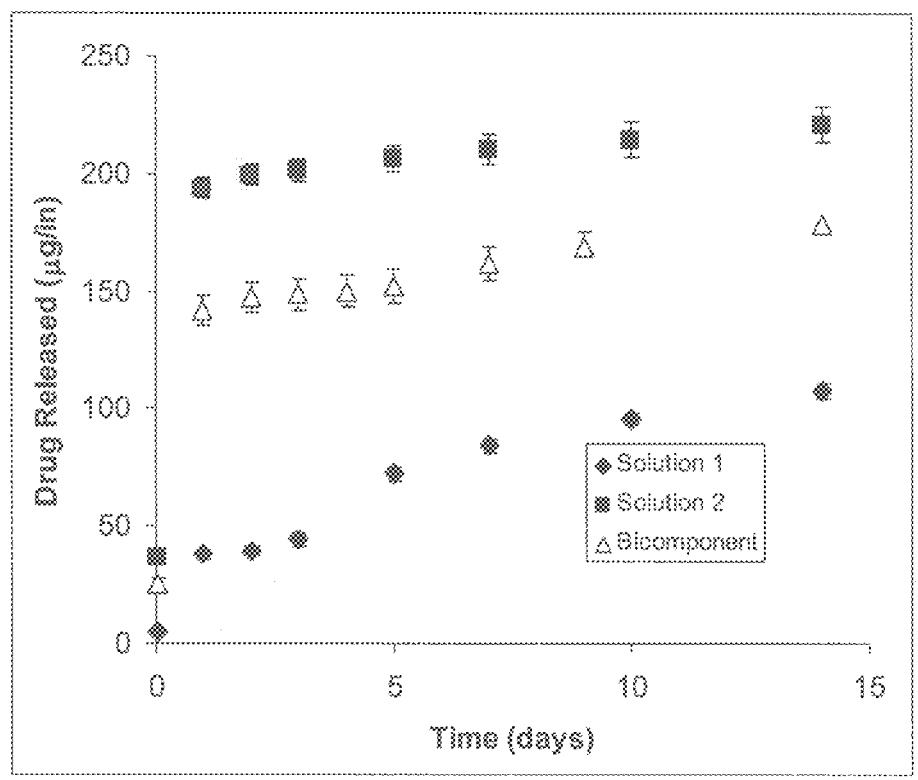
FIG. 8: Provides a comparison data graph of the release of levofloxacin in different fibers.
Figure 9A:
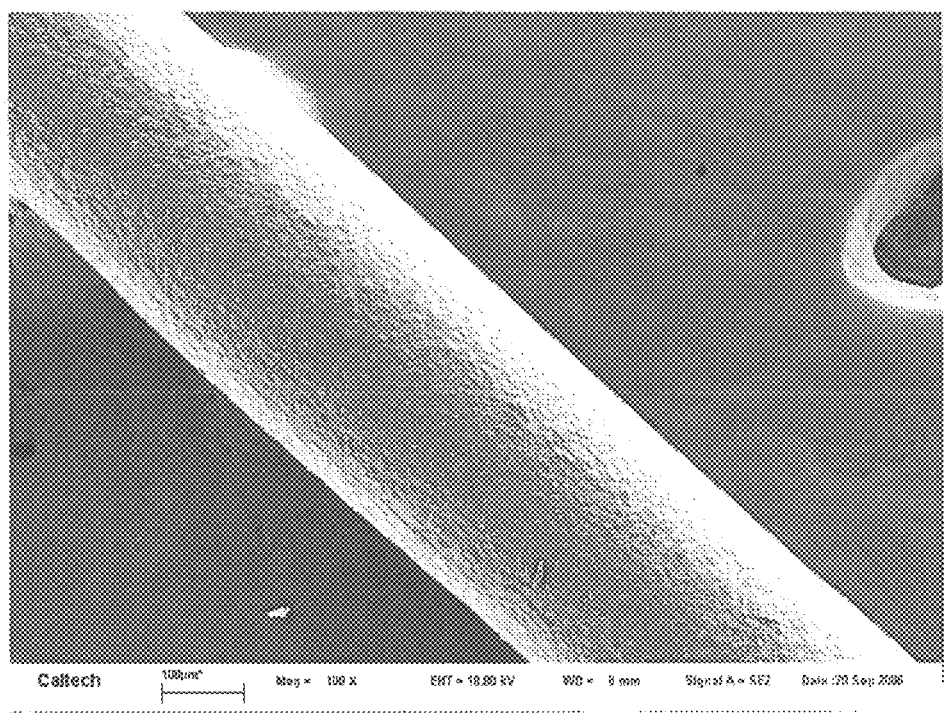
Figure 9B:
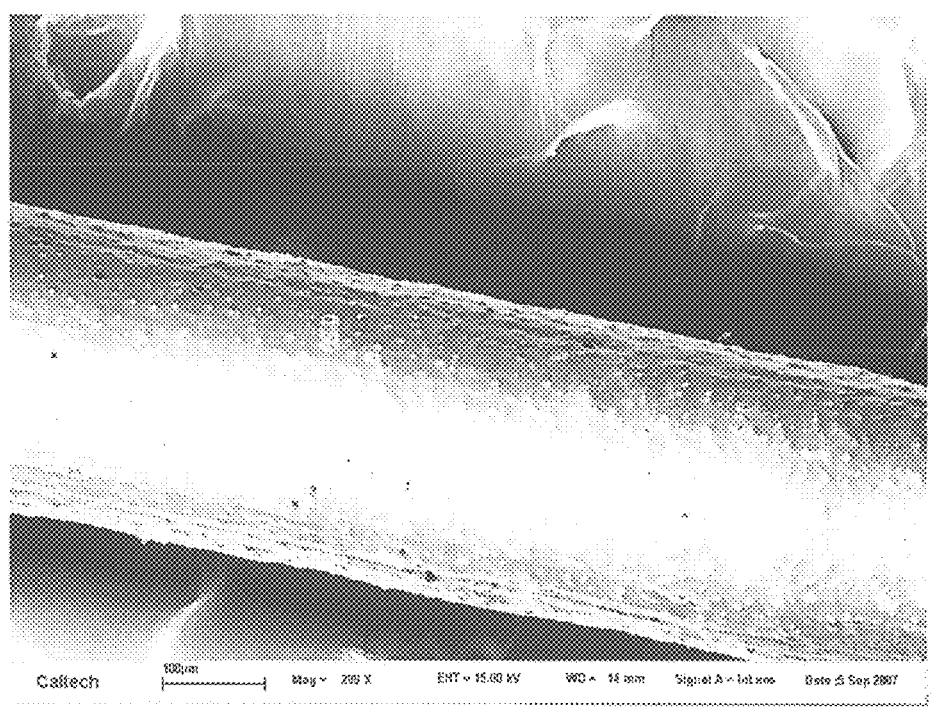

As previously discussed, the release profile of drug from a fiber is dependent on the amount of drug that was used during the formulation. It was found that if particles of drug (not dissolved) were present in the initial solution then release was much faster than if the drug was completely dissolved. A two component layered fiber was fashioned from each kind of solution. Solution 1 had 150 mg levofloxacin and 500 mg PLGA (RG 506 from Boehringer Ingleheim) dissolved in 1.5 gm DMSO. Solution 2 had 250 mg of levofloxacin but was the same otherwise. At room temperature, solution 2 was a suspension of levofloxacin (with particles visibly present) white solution 1 was translucent, indicating full levofloxacin dissolution. The solutions were joined through a 22 gauge Y-connector and extruded as described in Example 1. Fibers were also fashioned from solution 1 only and solution 2 only. The total extrusion time was 45 seconds and there was a draw ratio of 1.2 during extrusion. Finished products were all layered monofilaments with diameters of 250-300 m. Release was tested by incubating measured length of fibers in 1 ml of phosphate buffered saline (PBS) at 37 C. and periodically sampling and changing the buffer. Levofloxacin release into the PBS was determined by HPLC. Release profiles for each individual component and the combined layered fiber are shown in FIG. 8. Individually, fibers from solution 1 have a controlled release profile with small burst followed by sustained release. Fibers from solution 2 have a much higher drug Loading, but almost the entire drug is released within one day of incubation. The bicomponent filament has a combined release profile, with high initial release and then slower release. Scanning electron microscope (SEM) images are provided in FIGS. 9a to 9c that show both fiber formed solely from solution 1 (FIG. 9a) and solution 2 (FIG. 9b), as well as an example of a two component layered fiber fashioned from both solutions (FIG. 9c). In the image of FIG. 9c a clear demarcation is shown between the two phases, with the phase with the ground up drug showing a rougher surface with multiple bumps.

Example 3

Two Polymers Containing a Single Drug

Figure 11:
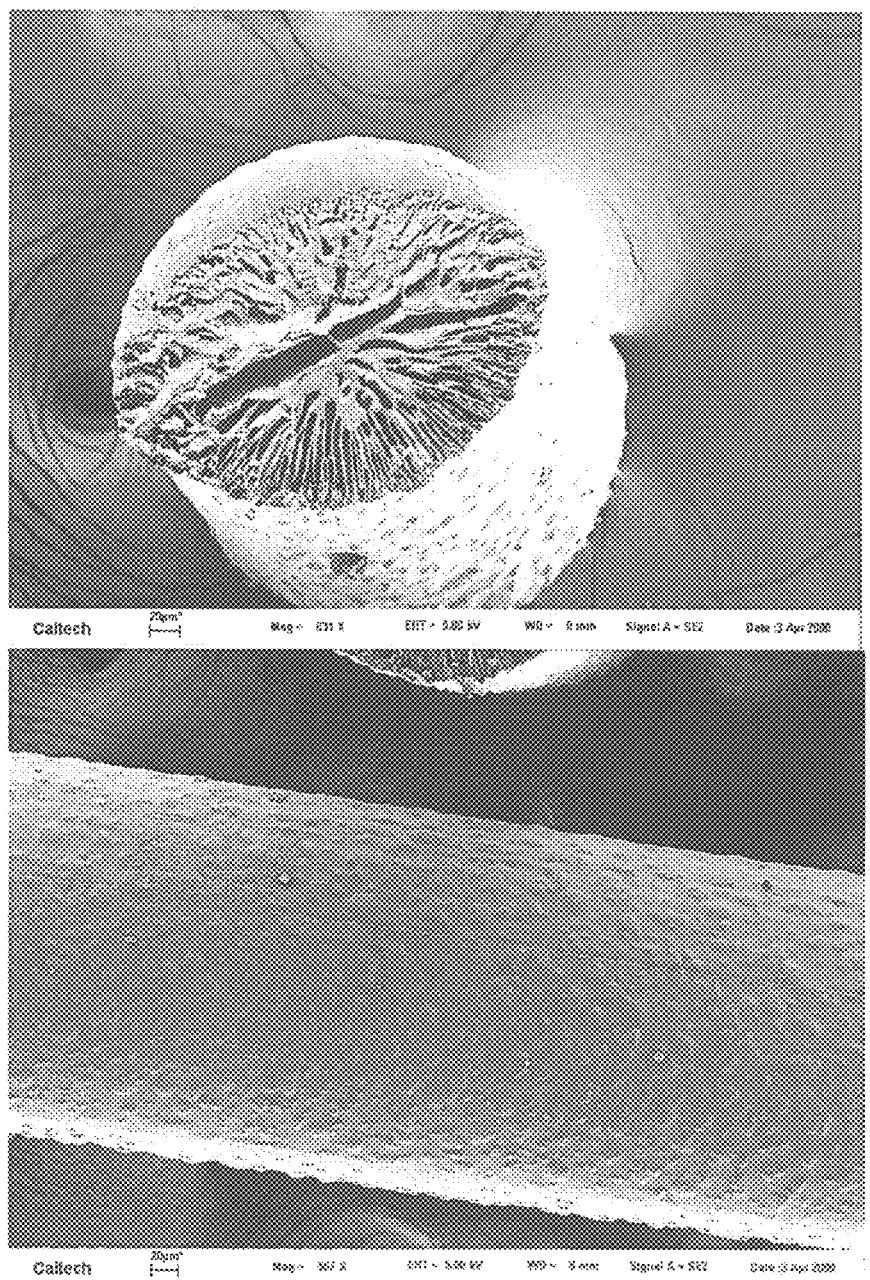
FIG. 11: Provides SEM images of a layered fiber made half of RG 506 and half of RG 756.

Two types of PLGA were formulated with levofloxacin and extruded as above. Solution 1 contained PLGA Resolmer RG 506, which has a 50:50 ratio of lactide:glycolide. Solution 2 contained PLGA Resomer RG 756, which has a 75:25 ratio of lactide:glycolide. The individual and combined releases are shown in FIG. 10. The fiber with RG 506 releases drug over approximately 2 weeks while the fiber made from RG 756 has a 10 day induction period before release begins. A layered, two-component device of the two polymers has a sustained release profile throughout the release areas of both individual polymers. SEM images of this fiber (FIG. 11) show that there are few differences between the two components, which is expected since they have similar compositions and drug contents and were dissolved in the same solvent.

Example 4

One Release Layer, One Structural Layer

Figure 12:
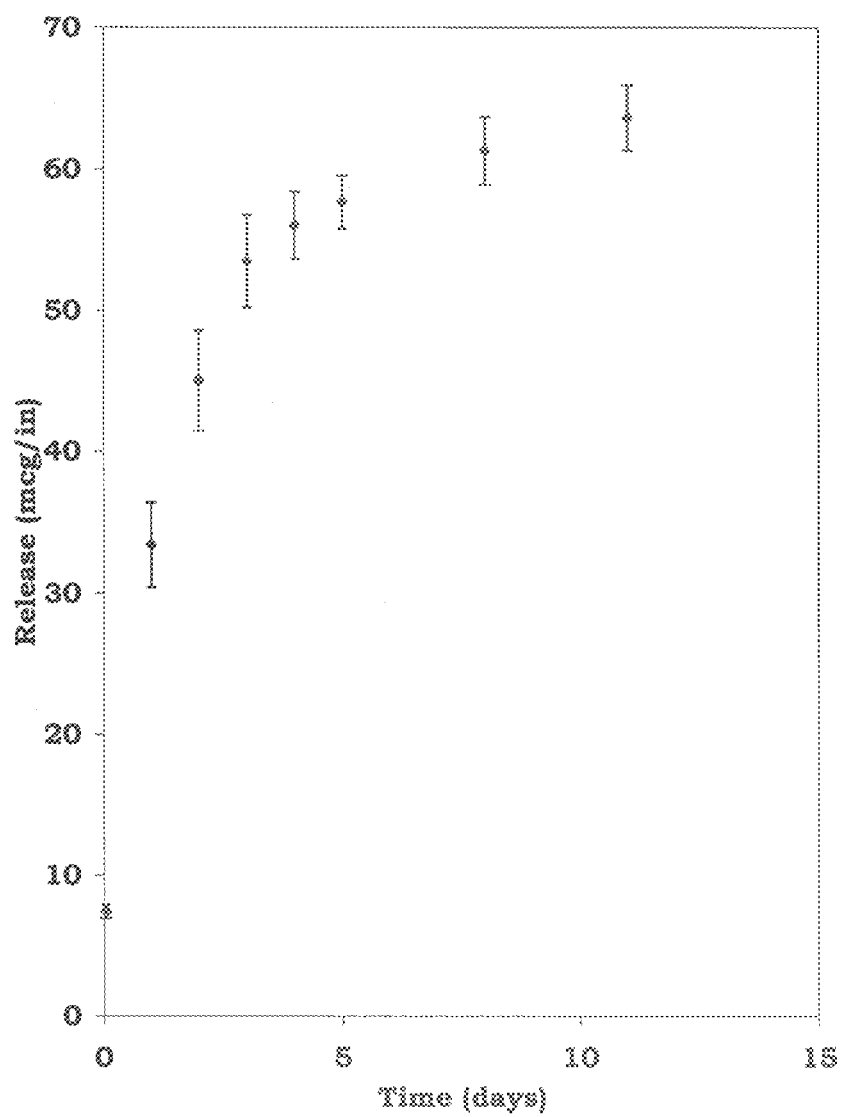
FIG. 12: Provides a data graph of the release of a drug from a biocomponent fiber with structural layer.
Figure 13:
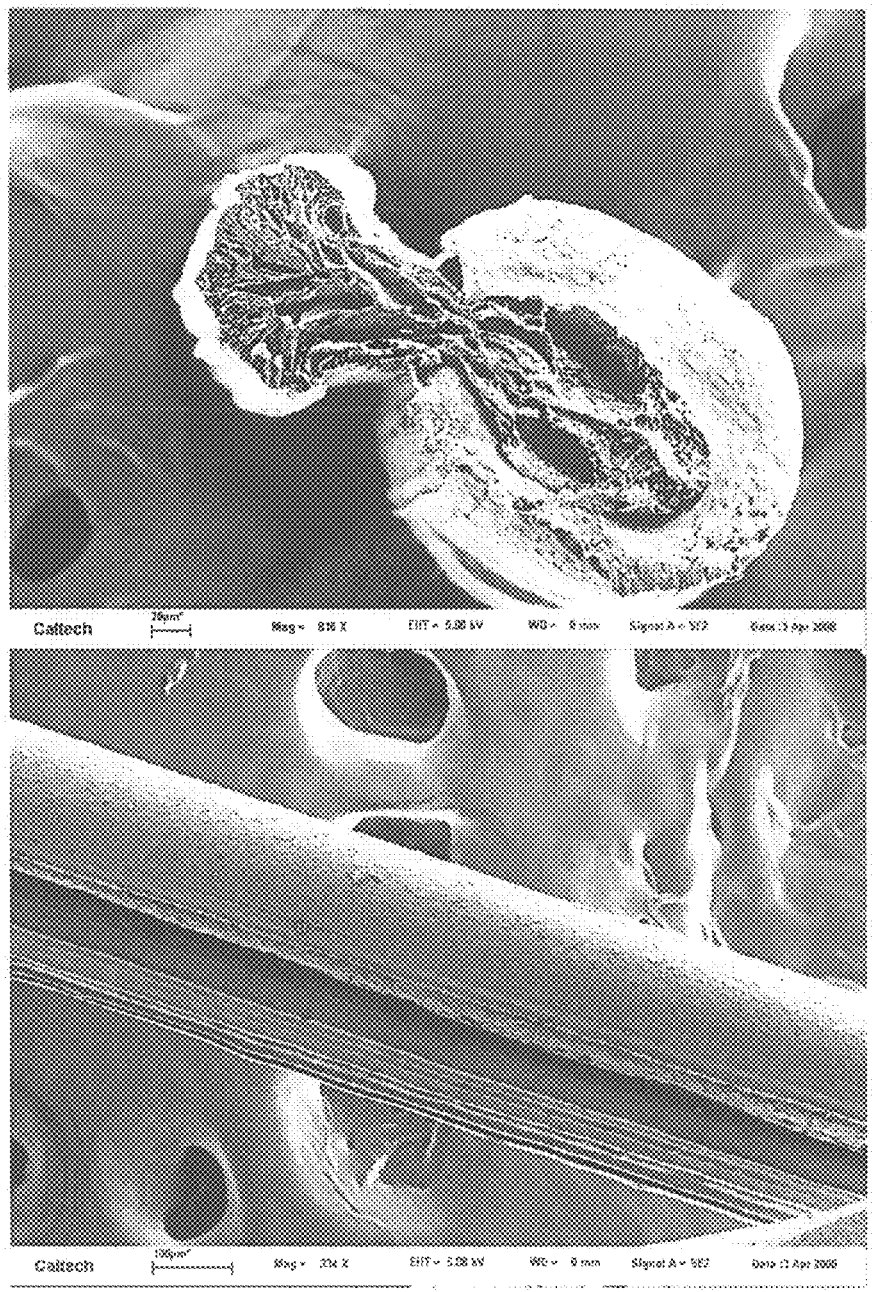
FIG. 13: Provides an SEM of a biocomponent fiber with a structural element and a release element.
Figure 14:
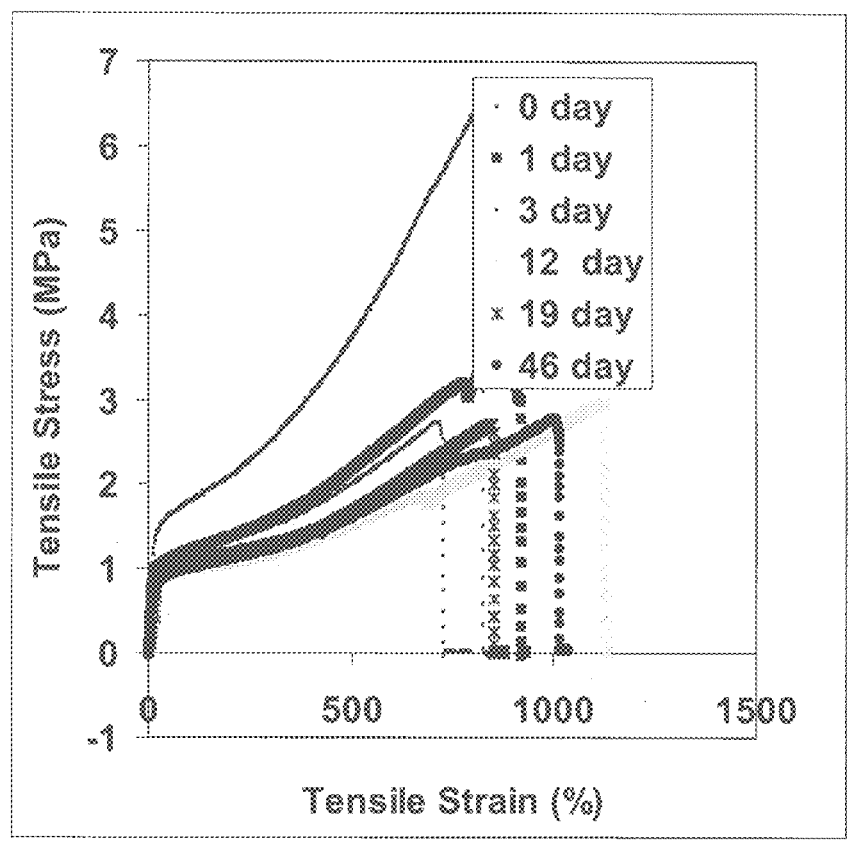
FIG. 14: Provides a data graph of the stress vs. strain of a layered fiber with a structural layer over time.

Solution 1 of this device was fashioned from PLGA and had the same composition as solution 1 from Example 1. Solution 2 consisted of 20% polycaprolactone (PCL) dissolved in acetone. PCL degrades at a much slower rate than PLGA. The release profile for this layered fiber is shown in FIG. 12. SEM images of this fiber are shown in FIG. 13. Since the two polymers are different and were indifferent solvents originally (with different solution properties, viscosity, etc.) one of the components has partially surrounded the other. While fibers made from just PLGA lose mechanical strength after only 6-8 days, this fiber showed stress vs. strain curves that were consistent over several weeks (FIG. 14). Even at day 46, this device still had considerable mechanical integrity.

Example #5

Ion Pair of Levofloxacin and Sodium Octanoate

Ion Pairing

One gram of sodium octanoate and one gram of levofloxacin were dissolved in 100 ml water. The pH was slowly adjusted to 6.0 by the addition of 1 M HCl. As the pH decreased, levofloxacin became protonated formed an insoluble HIP with the negatively charged octanoate. The precipitate was gathered by filtration to remove excess levofloxacin, dissolved sodium octanoate/octanoic acid, and salt. The sample was lyophilized overnight.

Making Wet-Spun Fiber with Paired and Unpaired Levofloxacin

A drug sample, either 150 mg levofloxacin or 250 mg levofloxacin-octanoate, is dissolved in 1.5 gm of dimethyl sulfoxide (DMSO) and 0.5 gm of polymer, in this case Resomer RG 506 and RG 756 from Boehringer Ingleheim, was added. The sample was allowed to dissolve at 37 C. in an incubator until all of the bubbles have surfaced. Blank solutions were made by the same process without any drug. The solution was loaded into a 5 ml glass syringe and extruded into a 16 L bath of water. The bath contains two guide posts to keep the filament below the surface and the strand is taken up by a 1 in diameter bobbin at the other side of the bath. For this experiment, the device was coagulated for 45 sec with a draw ration of 1.2. After drawing, the fibers were Laid flat in strips with ends secured to dry at room conditions for 2 days.

Scanning Electron Microscopy

Figure 15A:
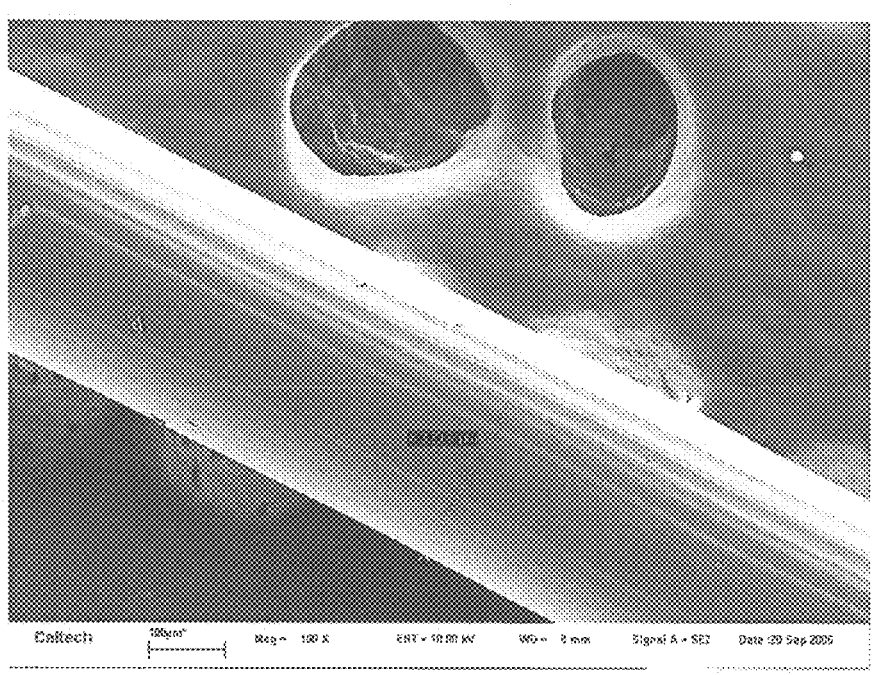
FIGS. 15a to 15c: Provide SEM pictures of a blank fiber (a), a fiber loaded with levofloxacin (b) and a fiber loaded with levofloxacin-octanoate (c)
Figure 15B:
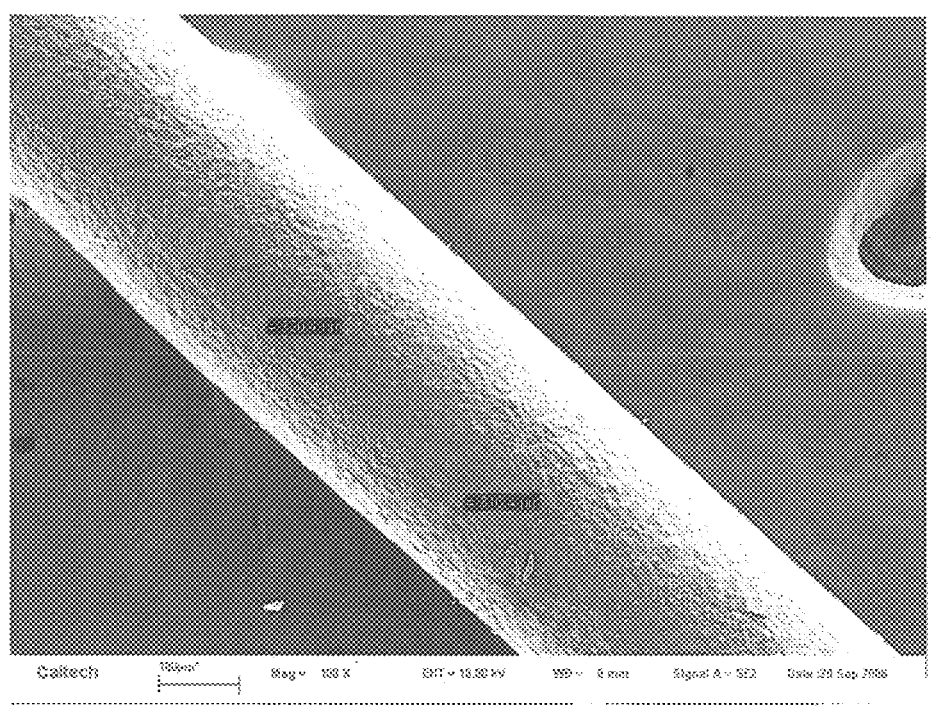
Figure 15C:
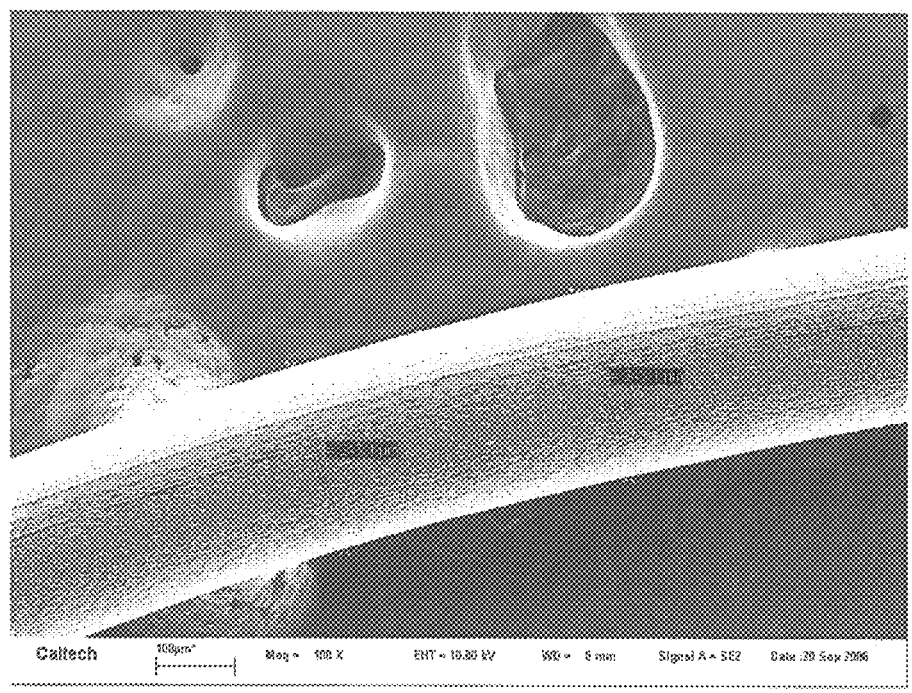
Figure 16A:
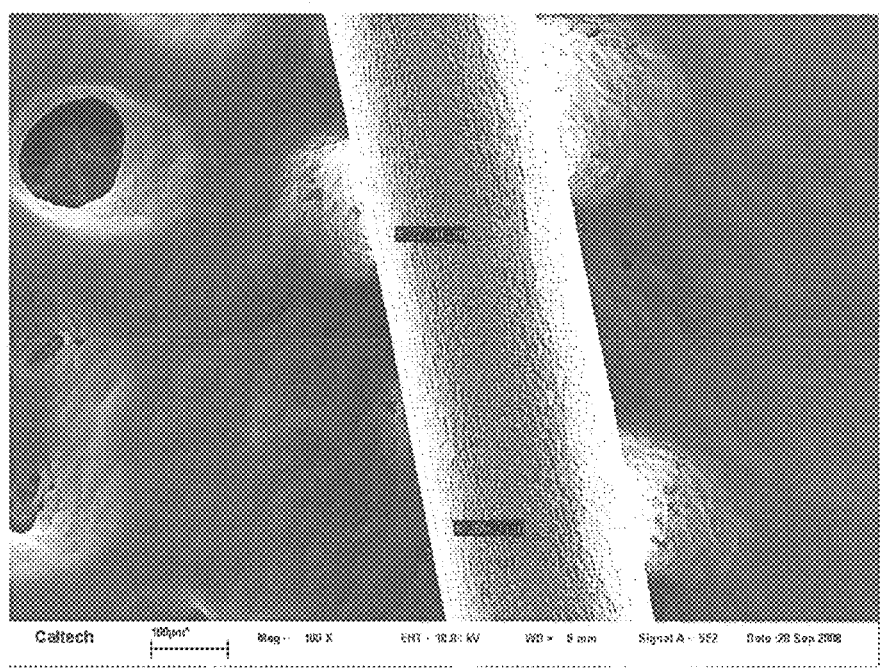
FIGS. 16a and 16b: Provide SEM images of a levofloxacin loaded RG 506 fiber, clearly showing the surface of the fiber (a) and the cut end (b)
Figure 16B:
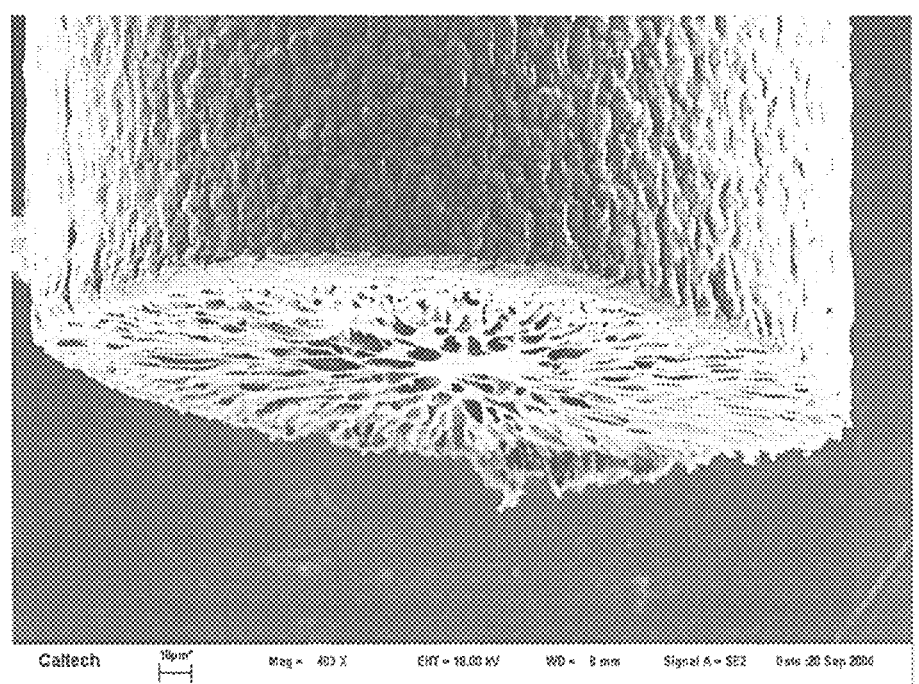

The morphologies of some of the fibers were investigated with scanning electron microscopy (SEM). Short fiber samples were coated with a Pt/Pd layer in a metal evaporator and imaged at 10,000 kV. FIG. 15 shows surface pictures of no drug (a), levofloxacin loaded (b), and levofloxacin-octanoate loaded (c) RG 756 fibers at 100× magnification. FIG. 16 shows a levofloxacin loaded RG 506 fiber, clearly showing the surface of the fiber (a) and the cut end (b). This end picture shows how porous the fibers end up being while the surface pictures show an almost continuous outer coat.

Differential Scanning Calorimetry

Figure 17:
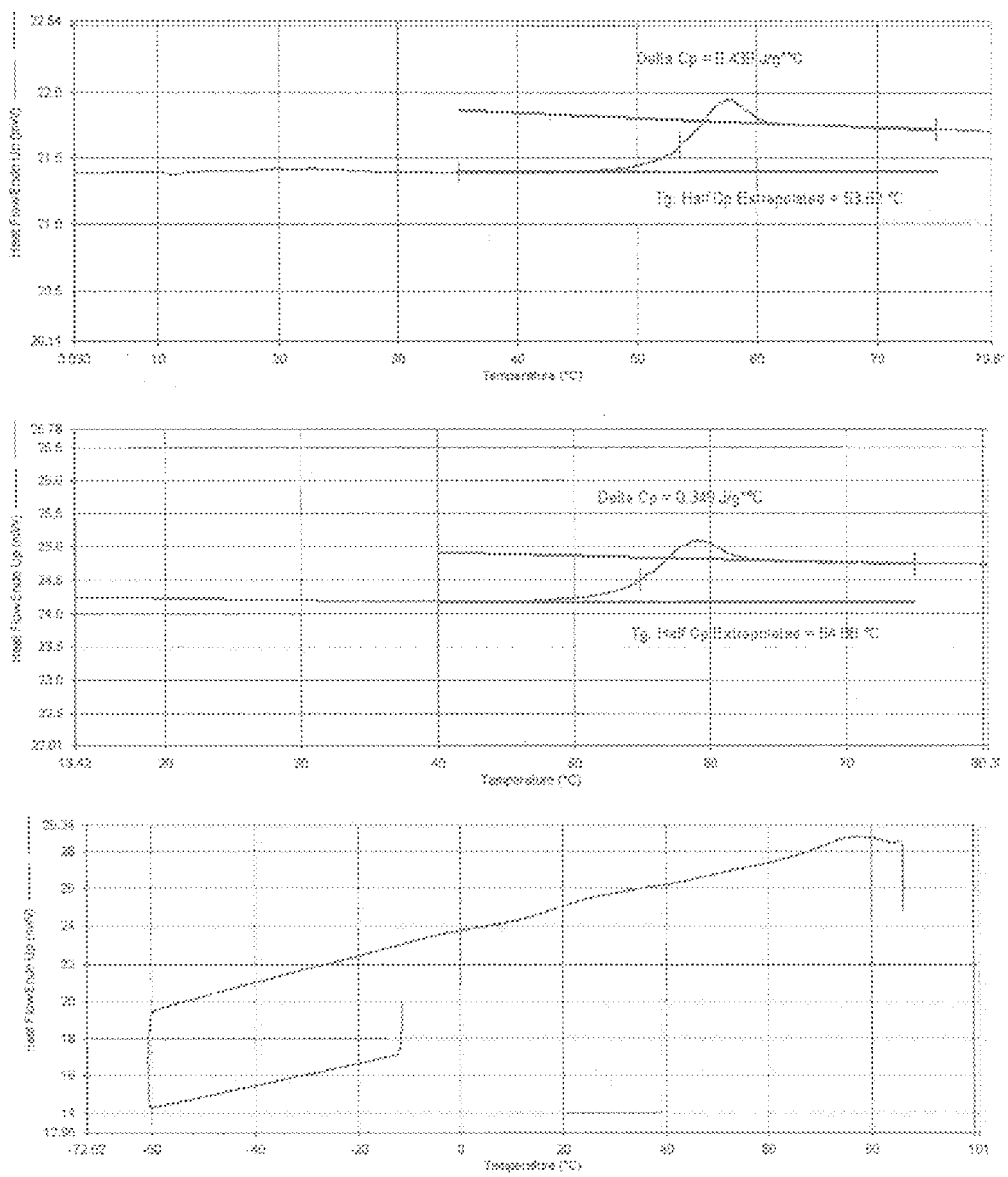
FIG. 17: Provides DSC traces of a blank fiber (top), levofloxacin loaded fiber (middle) and levofloxacin-octanoate loaded fiber (bottom)

Thermodynamic properties were investigated using a differential scanning calorimeter (DSC). RG 756 fibers with no drug, levofloxacin, and ion pair were heated at 10 K/min from −60 to 90 C. FIG. 17 shows the results. The fiber with no drug and the fiber with levofloxacin undergo a glass transition at 53-55 C. The ion paired fiber shows no discernable glass transition in the scanning range.

In-Vitro Drug Release

Figure 18:
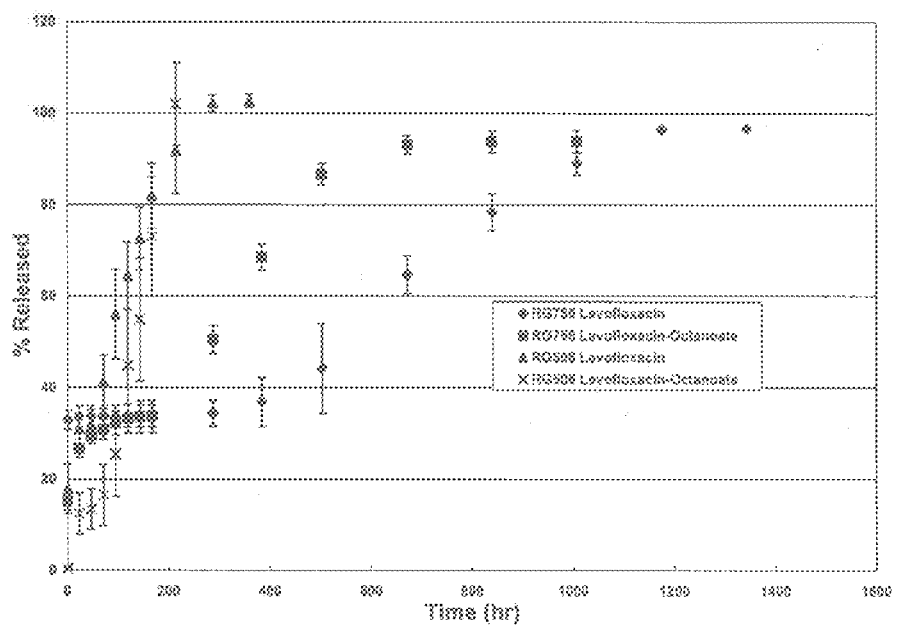
FIG. 18: Provides a data graph of levofloxacin release as a percentage of total levofloxacin for various polymers and ion pairing.

One inch of fiber was placed in 1 ml of Dulbecco's Phosphate Buffered Saline (DPBS) pH 7.4 at 37 C. on an incubating rocker in order to determine drug release from the device. At certain time points we removed the samples, emptied and replaced the DPBS, and diluted the samples appropriately for analysis by HPLC. The HPLC was run with a C18 column and a mobile phase of 50/50 0.1% TFA in acetonitrile/0.1% TFA in water. Levofloxacin was detected by fluorescence with an excitation of 292 nm and an emission of 494 nm. Each fiber was tested in triplicate and the results with standard deviations are shown in FIG. 18. The RG 756 polymer is supposed to degrade more slowly according to available literature, and the release from the fibers shows this. The ion pair appears to suppress the initial burst of drug from the device and accelerate release from degradation.

Drug Loading Measurements

To determine drug loading for each of the fibers, a short length (usually about 0.5 in, accurately measured) of each fiber was dissolved in 1 ml of 1 M NaOH. The solution was neutralized with 1 M HCl and 8 ml of DPBS were added. The concentration of each solution was determined by HPLC and the drug loading in g/in was determined. Three samples were run for each fiber and the results are shown in Table 1, below. The ion paired fibers consistently showed better loading than the unpaired fibers.

TABLE 1

Fiber Loading For Levofloxacin And Levofloxacin-Octanoate Fibers

| Name | Drug Loading [µg/in] | Standard Deviation |
|---|---|---|
| RG 506 Levofloxacin | 86 | 3 |
| RG 506 Levofloxacin-octanoate | 144 | 5 |
| RG 756 Levofloxacin | 108 | 4 |
| RG 756 Levofloxacin-octanoate | 146 | 5 |

Loading Efficiency

The expected levofloxacin/in was determined by first calculating the volume extruded/length of fiber from knowing the pumping rate and draw ratio. Since we also know the concentration in mass/volume of the polymer solution, we can determine the expected levofloxacin/in in the fiber. This number was compared to the experimentally determined loading to find the efficiency (Table 2). As it can be seen, HIP increases the loading efficiency for each polymer type.

TABLE 2

Efficiency Of Loading Of Drug On Fiber

| | RG 756 Unpaired | Paired | RG 506 Unpaired | Paired |
|---|---|---|---|---|
| Experimental mg/ml | 79 | 79 | 79 | 79 |
| Calculated mg/ml | 39 | 52 | 31 | 52 |
| Efficiency | 50 | 66 | 39 | 65 |

Mechanical Testing

The tensile strength and elongation before break for each fiber was determined on an Instron 5542. The diameter of the fibers was measured under a light microscope calibrated for diameter measurements using precision wire as standards. A small length of fiber was clamped at both ends (length outside of clamp accurately recorded) and mounted on the tensile testing apparatus. The fiber was stretched to breaking at a strain rate of 0.5%/sec. Table 3 shows the results of the mechanical testing for paired, unpaired, and blank fibers of both polymers. Note that levofloxacin loaded fibers are very brittle and do not elongate very much before breaking. On the other hand, levofloxacin-octanoate fibers are quite flexible and elongate further than blank fibers before breaking.

TABLE 3

Mechanical properties of RG 756 fibers

| | Diameter (µm) | Tensile Strength (MPA) | St Dev | Elongation (%) | St Dev |
|---|---|---|---|---|---|
| Ion pair | 240 | 7.3 | 0.3 | 348 | 30 |
| Levofloxacin | 330 | 4.8 | 0.1 | 21 | 3 |
| Blank | 340 | 5.3 | 0.1 | 119 | 8 |

Figure 19:
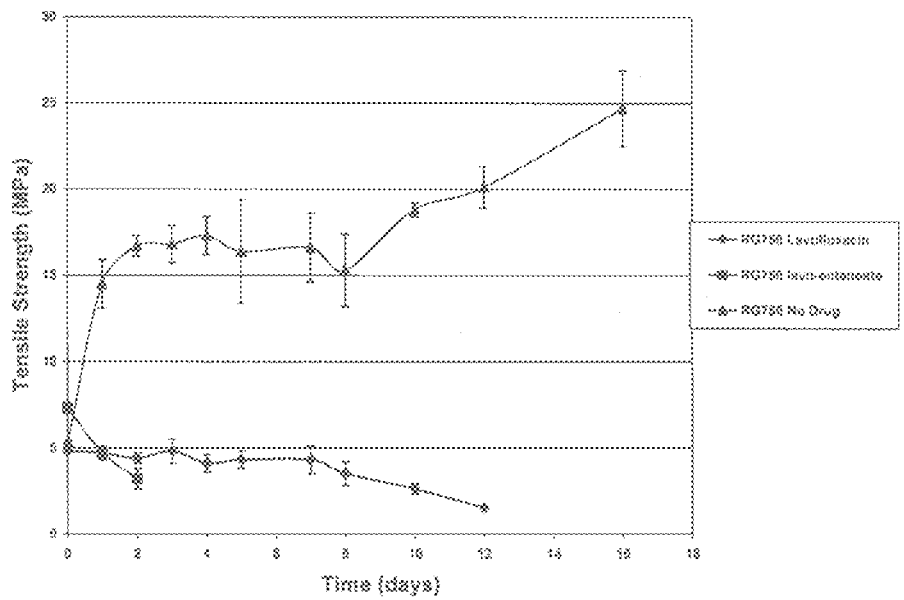
FIG. 19: Provides a data graph of tensile strength as a function of time for various fibers.
Figure 20:
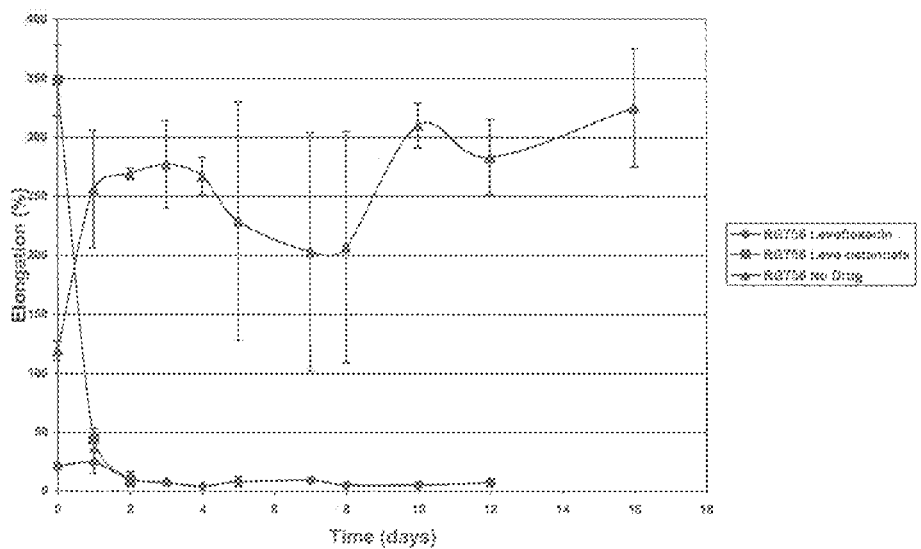
FIG. 20: Provides a data graph of elongation as a function of incubation time.

Mechanical properties were also measured as a function of incubation time. Four feet of fiber was cut into approximately 4 in lengths and submerged in DPBS at 37 C. At each data point, a short part of the fiber was cut and removed from the DPBS. The mechanical properties of the fiber were then determined by the method above. Data for the RG 756 fibers is shown in FIGS. 19 and 20. FIG. 19 shows the tensile strength as a function of time while FIG. 20 shows elongation vs. time. The data points stop when samples were unable to be taken due to severe loss of strength. The ion paired fiber lost strength before the unpaired or blank fibers, with the sample breaking during casual handling, at 3 days. The levofloxacin loaded fiber becomes increasingly brittle, but maintains some strength through 12 days. Meanwhile, the blank fiber actually increases in strength and elongation after incubation and is still strong at 26 days although has become brittle by this time.

In-Vivo Testing: Implantation in the Rabbit Eye

For this animal experiment, fibers of polymer RG 756 were sterilized by dipping in isopropanol, followed by sterile DPBS. Six New Zealand white rabbits were marked numbers 1-6. The rabbits were anesthetized with isofluorane during any procedure and were carefully monitored by trained animal facility staff during the entire experiment. All six rabbits received an experimental fiber with either levofloxacin or ion pair. In the other eye, three received a blank fiber while the other three received no fiber.

Figure 21A:
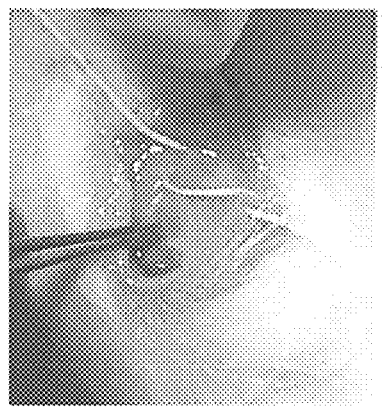
FIGS. 21a and b: Provide photographs of the double pass implantation before (a) and after (b) trimming the ends of the fiber.
Figure 21B:
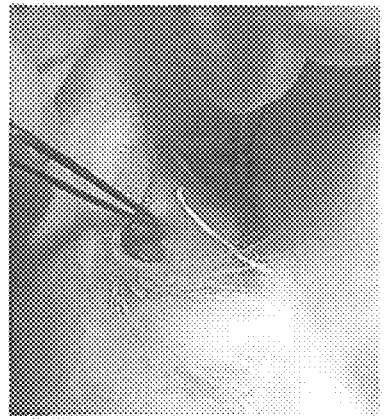

A fiber was threaded through a needle and passed under the conjunctiva in the inferior fornix. After the first pass, the needle was brought back to a position near the initial point of insertion and passed again through the conjunctiva in a similar fashion. The ends of the fibers were cut to leave sizable tags. The final implant consisted of end tags, lengths of fiber buried in the conjunctiva, and a strip of fiber outside the conjunctiva between the exit hole of the first pass and insertion point of the second pass. Pictures of this implantation method are shown in FIGS. 21a and 21b.

Figure 22:
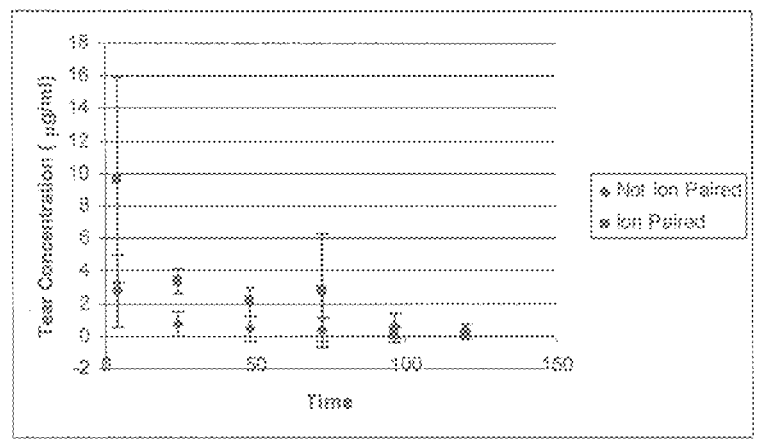
FIG. 22: Provides a data graph of tear concentrations as a function of time for ion paired and unpaired fibers.

Drug release into the tear film was monitored as a function of time. At given time points, a Schrimer's Test paper was inserted to soak up tears for 15 sec. The mass before and after tear contact was recorded to monitor tear volume collected (usually 5-20 l). The papers were dried, then the contents were resuspended in 200 l of DPBS and concentration of levofloxacin was determined by HPLC. No levofloxacin was detected in either the eyes with no fiber or the eyes with a blank fiber. The tear concentrations of levofloxacin are shown in FIG. 22. Levofloxacin is effective against a broad spectrum of bacteria at concentrations over 1 g/ml. The ion paired fibers seem to keep drug levels high for a longer period than the unpaired.

At each tear collection, the fiber was examined by grasping the upper and lower lids of the eye and pulling them apart, revealing the inferior fornix. Looped fibers were clearly visible and the presence of fiber could be determined through direct observation. Drug levels are detectable until the days where fibers are not seen, an observation that confirms the necessity of having fiber present outside of the conjunctiva. The ion paired fibers seemed to give higher tear concentrations of levofloxacin than the unpaired fibers, but they started deteriorating more quickly and one was gone by three days while the other two were not observed on the fourth day. For the unpaired fibers, two of them were gone by day three, but one of them was present until day five. The control fibers seemed to either leave the eye immediately or stay for a long time, with one fiber lasting all the way until the end of the experiment on day 10. This showed that it is possible for a filament to stay in the eye for 10 days. Subsequent implantations with no drug fibers where special care was taken to secure the ends of the fiber (so that it could not extrude from the implantation site) showed that the fiber can consistently last for 10 days.

Example #6

Fibers Plasticized with Acetyl Tributyl Citrate

Figure 23:
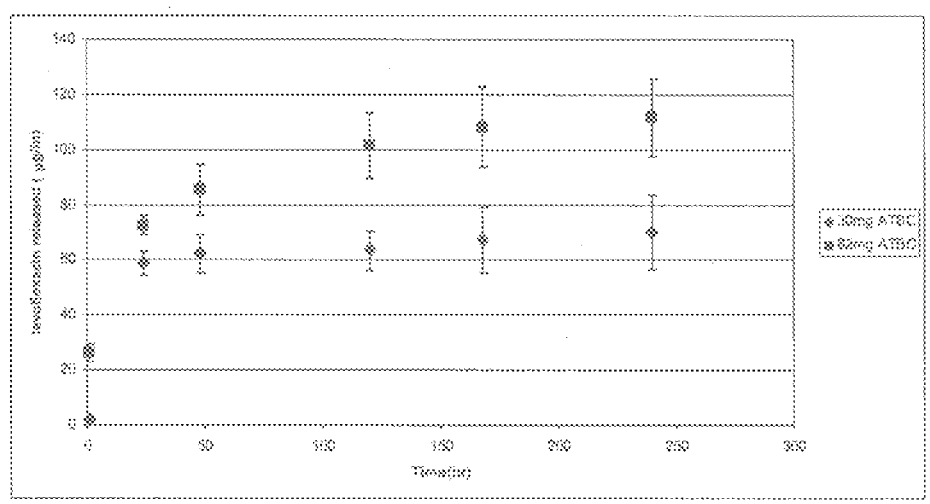
FIG. 23: Provides a data graph of levofloxacin release for fibers with ATBC.

Polymer solutions were made with 150 mg levofloxacin, 1.5 gm DMSO, and 500 mg RG 756. To one of the solutions, 30 mg acetyl tributyl citrate (ATBC) was added while 62 mg of ATBC was added to a second solution. Fibers were extruded as described in Example 5. The in-vitro release from the fibers was also tested as above except that levofloxacin concentration was determined by fluorescence on a plate reader with excitation of 280 nm and emission of 465 nm. The release results are shown in FIG. 23. The increased amount of ATBC leads to a faster release and does not plateau as quickly as the unplasticized RG 756 fibers shown in Example 5. This shows that a hydrophobic plasticizer can be used to increase the rate of release of drug from a wet-spun device.

Example #7

Stretching a Plasticized Fiber

Figure 25:
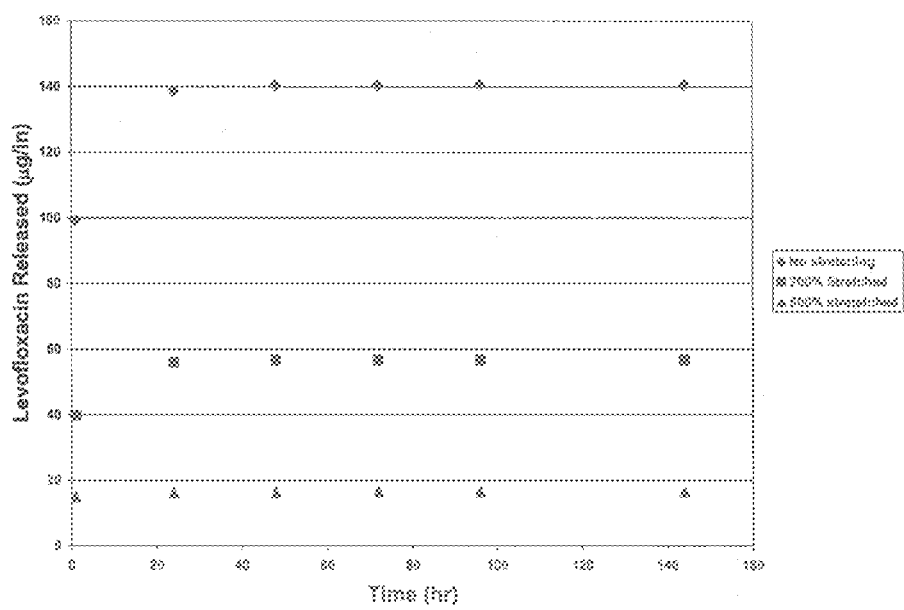
FIG. 25: Provides a data graph of levofloxacin release for stretched fibers.

A fiber was made with 150 mg levofloxacin, 1.5 gm DMSO, 500 mg RG 756, and 100 mg of the plasticizer acetyl triethyl citrate (ATEC). One length of the fiber was allowed to dry without stretching. Two other lengths were stretched post-extrusion to 200% and 500% of their initial length. Light microscope pictures of the fibers are shown in FIG. 24 while levofloxacin release profiles are shown in FIG. 25. From the microscope pictures, it can be seen that the diameter decreases with the square root of the stretching. This allows the production of thinner and thinner fibers. The release profiles are the same in shape, a fast initial burst followed by a plateau, with total release close to proportional to the stretching.

Example #8

Changing Mechanical Properties with Plasticizer

Figure 26:
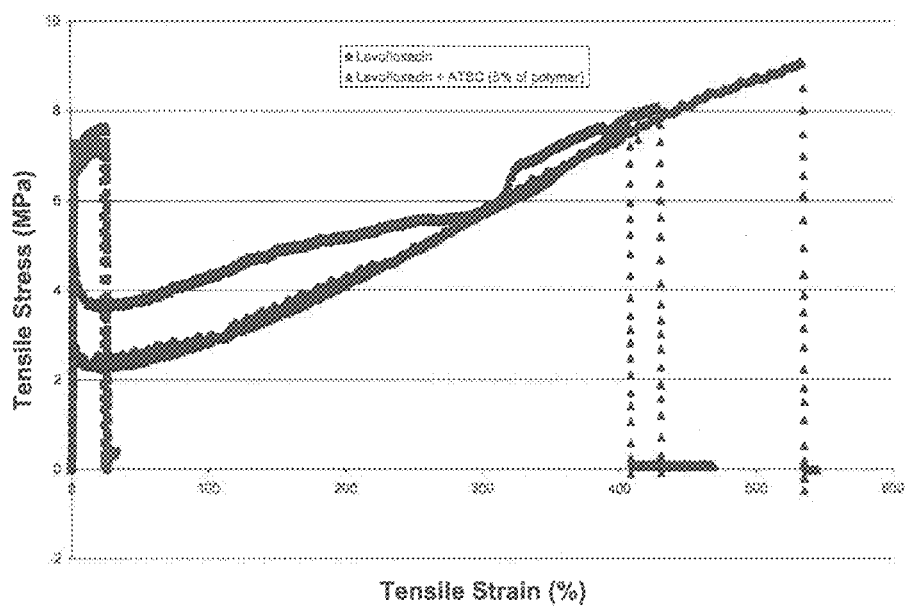
FIG. 26: Provides a data graph of the difference in mechanical properties between fibers with and without plasticizer.

Fibers were made with 150 mg levofloxacin, 0.500 mg RG 756, and 1.5 gm DMSO. One of the fibers also had 25 mg ATEC while the other had no plasticizer. The stress/strain curves for the fibers (in triplicate) are shown in FIG. 26. The plasticized fiber extends far more than the unplasticized one.

Example #9

Complexing Octanoic Acid with Cyclodextrin

Figure 27:
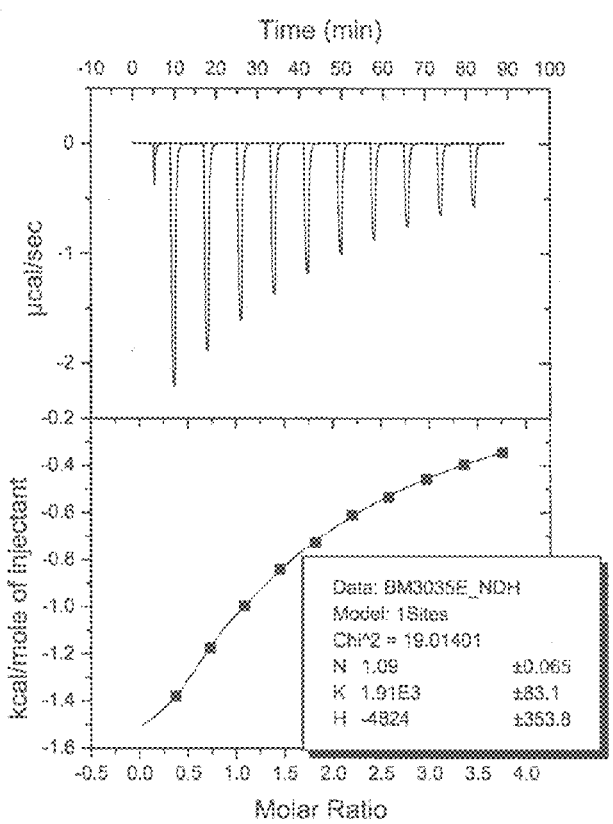
FIG. 27 provides a data graph showing results of an isothermal titration calorimetry study of the binding energy between octanoic acid and cyclodextrin.

The binding energy between octanoic acid and -cyclodextrin (-CD) was determined by isothermal titration calorimetry. Briefly, solutions used of 2 M-CD and 0.2 M octanoic acid were made in DPBS. Ten injections of 25 ml each of the octanoic acid solution were made into 1.37 ml of the cyclodextrin in a Microcal ITC unit. The results are shown in FIG. 27. A 1:1 complex is formed with an equilibrium constant of 1900.

Example #10

Multi-Component Drug Delivery Filament

A biodegradable multi-component layered filament was formed for controlled delivery of multiple drugs. Specifically, the filament in this example was designed to provide for the release of dexamethasone and levofloxacin.

Summary

This study focuses on layered fibrous devices made from three types of amorphous PLGA, one with a 50:50 lactide to glycolide ratio, one with a 75:25 ratio, and one made entirely of d,l-lactide. Using dimethyl sulfoxide (DMSO) as a solvent and water as an antisolvent, levofloxacin and dexamethasone containing filaments were prepared.

Filaments were prepared by a wet-spinning procedure, where a solution of poly(lactide-co-glycolide) (PLGA) and drug, dissolved in dimethyl sulfoxide (DMSO), was coagulated in water. Filaments were made with PLGA of three different lactide to glycolide ratios and under several different extrusion conditions. Compositional analysis of the resulting filament was performed by independently determining the amounts of drug, DMSO, water, and polymer by various methods. Devices had drug loadings up to 40% of device mass and drug retention was greater than 40% for all of the filaments. Most of the filaments are made from a solution where the drug and polymer are both dissolved, but some of the devices are formulated from solutions with suspended drug particles.

Each device was further characterized to determine release, thermal, and mechanical properties. It was found that residual DMSO was present in the filaments, but diminished with increased coagulation time and was mostly undetectable after one day of incubation in phosphate buffered saline. Filaments made from homogenous solutions displayed characteristic patterns for degradation controlled release, while filaments made from solutions containing suspended drug particles displayed rapid release.

This study demonstrates the flexibility of wet-processing for the production of drug loaded layered filaments and explores the interplay of composition with drug release, thermal properties, and mechanical properties.

Materials

Levofloxacin, dexamethasone, and poly(d,l-lactide) (PDLLA, MW 75,000-120,000) were purchased from Sigma-Aldrich. Poly(d,l-lactide-co-glycolide)'s were obtained from Boehringer Ingleheim. The PLGA's used for this study were Resomer RG 506 (50:50 lactide:glycolide, intrinsic viscosity of 0.82) and Resomer RG 756 (75:25 lactide:glycolide, intrinsic viscosity of 0.80). DMSO, 0.100 N HCl, and 0.100N NaOH were obtained from VWR.

Method of Filament Formation

Filaments containing levofloxacin and dexamethasone were processed by a wet-spinning procedure. An accurately measured amount of drug was placed in a glass vial to which dimethyl sulfoxide (DMSO) was added. This solution was sonicated for 1 minute to facilitate dissolution of the drug. After sonication, PLGA was added to each vial and the vial vortexed to mix all components. The solution was then allowed to equilibrate for 6 hours, vortexing occasionally to mix, at a given temperature to eliminate all trapped bubbles. Table 4, provided in FIG. 28 shows the processing conditions for all of the filaments used for these experiments (naming of the devices follows the pattern of Polymer-Drug#). The solutions were homogenous, with drug and polymer both dissolved to make a translucent solution, with the exceptions for 506-L2 and 756-L2, which were suspensions of solid drug particles formulated above the solubility of levofloxacin in DMSO. These conditions were chosen to allow comparisons between polymer type (506-L1, 756-L1, and PDLLA-L1), drug type (506-L1 and 506-D1), coagulation time (506-L1, -L5, and -L6), amount of drug (506-L1, -L2, -L4, -D1 and -D2 and 756-L1 and -L2), and formulation temperature (506-L1 and L3). Solutions were loaded into a 5 ml syringe equipped with a 22 gauge flat-tipped needle (Small Parts Inc.) and mounted on a syringe pump. The solutions were extruded into a 16 L water bath (22±2° C.) and taken up onto a 1 inch bobbin rotated by a DC gear motor. The pump speed and uptake rate was chosen to set a particular coagulation time (Table 4) with a draw ratio of 1.2. Fibers were secured tautly without stretching and allowed to dry under ambient conditions for two days.

Method of Determination of Levofloxacin Content

Total drug loading of the filaments was determined by dissolving accurately measured sections of the device with 1 M NaOH. The drug content of the resulting solution was measure by using high performance liquid chromatography (HPLC) with a C18 column (Agilent 1200 series HPLC). The mobile phase was 49.95% water, 49.95% acetonitrile with 0.1% trifluoroacetic acid. Levofloxacin was determined by fluorescence with an excitation at 292 nm and emission at 494 nm while dexamethasone was measured by absorbance at 254 nm. Some samples were measured, placed in 1.5 mL Eppendorf tubes, and incubated in phosphate buffered saline (PBS, pH 7.4) at 37° C. on an incubating rocker for one day. Other samples were tested for drug content without incubation.

Method of Determination of Water Content

Water content of the filaments was determined by thermogravimetric analysis. Samples were cut into small pieces, placed in an $Al_2O_3$ crucible and heated to 125° C. for 45 min. Mass was monitored and the difference in mass before and after heating was recorded. Water content of incubated filaments was done after blotting the filaments with a Kimwipe to remove water on the external surface of the filament.

Method of Determination of DMSO Content

To determine DMSO content of the filaments, approximately 30 cm (accurately measured) was dissolved in deuterated chloroform with an internal standard of 1% TMS. The sample was then analyzed by proton nuclear magnetic resonance (NMR). By comparing the integration of the TMS peak to the DMSO peak, the amount of DMSO in the sample can be determined. Some samples containing dexamethasone and incubated samples needed to be filtered through a 0.2 m syringe filter to remove particles before NMR analysis.

Method of Determination of Polymer Content

Polymer content was directly determined by digesting an accurately measured length of filament (approximately 30 cm) with 10 mL 0.100 M NaOH. The solution was back titrated to neutral with 0.100 M HCl, with the amount of HCl accurately recorded. For every ester bond that is hydrolyzed, one hydroxide ion will be consumed, so the amount of ester bonds can be determined and translated into the mass of polymer in solution. Incubated filaments were first rinsed with water three times before digestion.

Method of Determination of Drug Release

One inch sections of filament were placed in 1.5 mL tubes. One mL of phosphate buffered saline (pH 7.4) at 37° C. was added to each vial. The tubes were incubated at 37° C. under gentle rocking and at various times, the buffer was replaced with fresh PBS. The removed PBS was analyzed for drug content by HPLC as described above.

Method of Mechanical Testing

Load vs. strain curves for the fibers were collected on an Instron 1150 mechanical properties testing apparatus. Experiments were run under ambient conditions, where temperature was 22±2° C. with relative humidity at 50±10%, and under incubated conditions, with the filament submerged in PBS at 37° C. The samples were drawn at a strain rate of 1%/sec and the resulting tension was recorded. The load that the filaments were bearing at the time of breakage was recorded, as was the maximum elongation of the device.

Extrusion and Composition Result

Figure 29A:
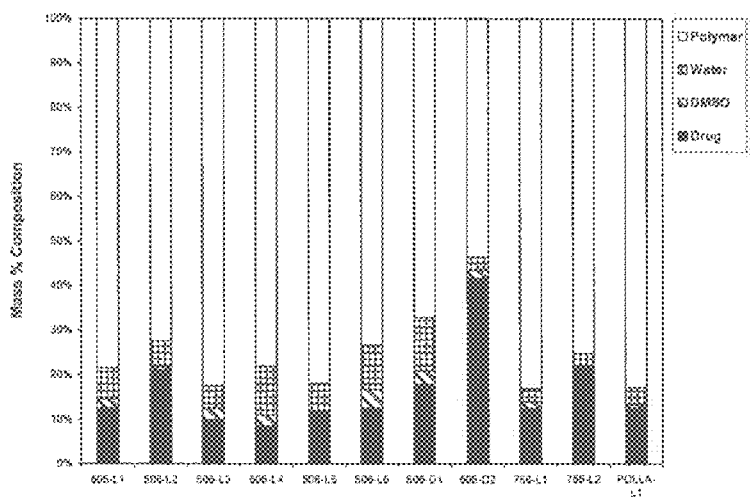
FIGS. 29a and 29b: Provide data graphs showing the composition of filaments after a) extrusion (top) and b) 1 day of incubation (bottom) showing DMSO, drug, polymer, and water contents.
Figure 29B:
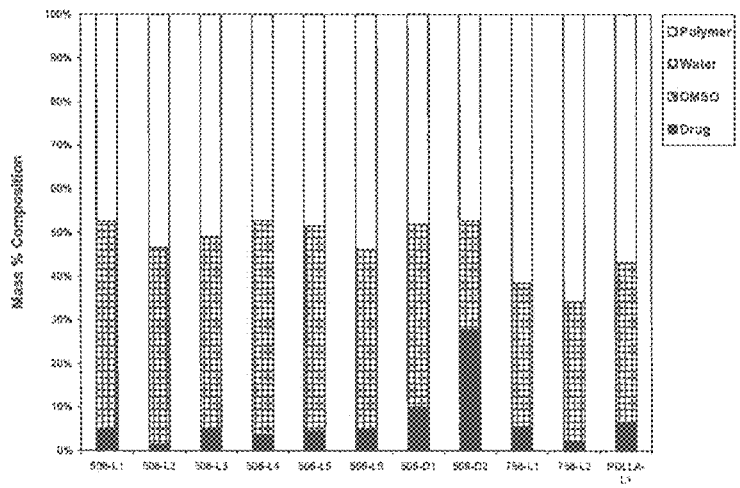
Figure 30:
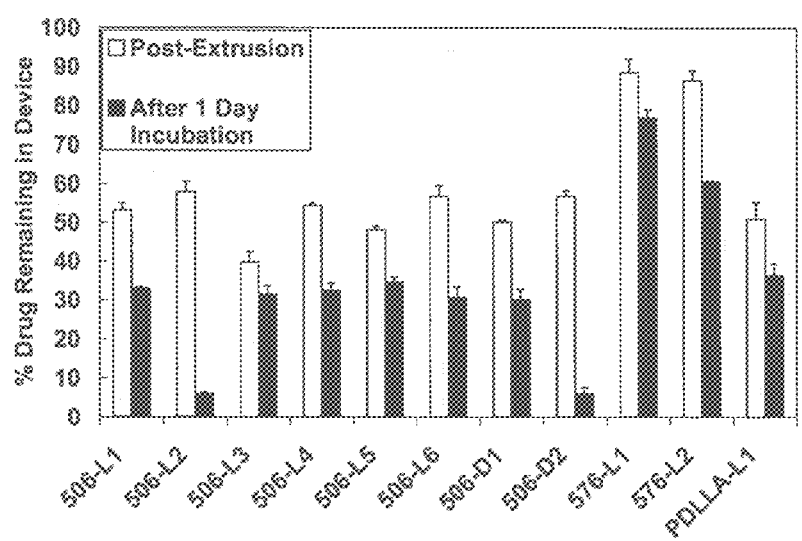
FIG. 30: Provides a data graph of drug remaining in the devices after extrusion and 1 day of incubation as a percentage of drug originally present in formulation.
Figure 31A:
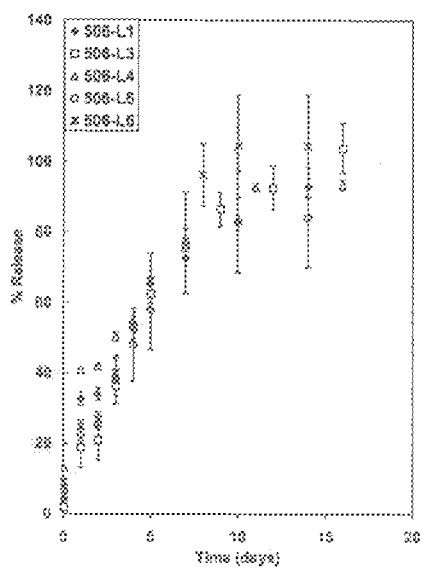
FIGS. 31a to 31d: Provide from upper-left, clockwise, the release profiles of a) filaments containing levofloxacin formulated from single phase solutions, b) filaments formulated with dissolved and suspended levofloxacin, c) filaments made from different polymers, and d) filaments formulated with dexamethasone (506-L1 for comparison)
Figure 31B:
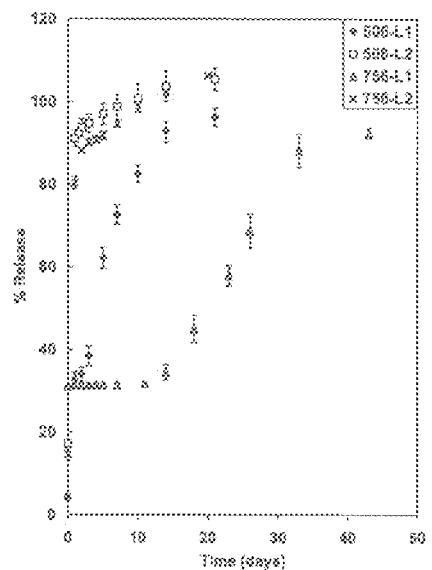
Figure 31C:
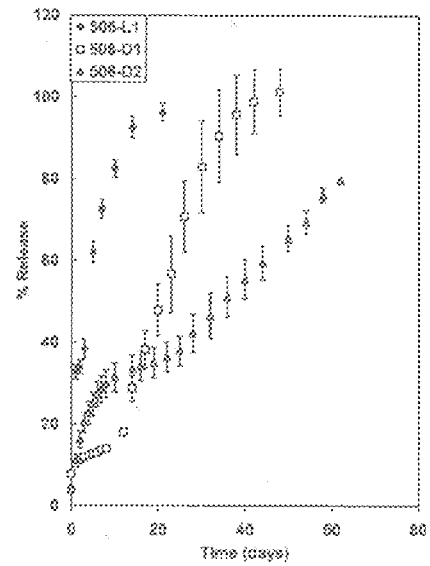
Figure 31D:
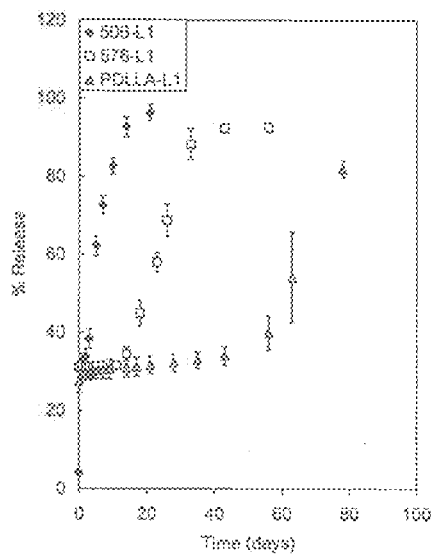

Filament compositions are shown in FIG. 29 and are broken down by mass fraction of the total device. Compositions by linear concentration can be found in Supplementary Information. The polymer used for fabrication is the primary component of every device. The digestion and titration method used for compositional analysis provided values in line with mass balances performed over the extrusion bath, indicating full retention of PLGA during extrusion. A small amount of DMSO present after extrusion, though this amount is only a small fraction of the DMSO used for formulation and varies with formulation conditions and compositions. After one day, the amount of DMSO in several of the fiber fell below the sensitivity of detection for our assay, with only small amounts present (less than 0.25%) even when detected. While residual water is present after extrusion, the filaments all swell significantly after a day of incubation in PBS at 37° C. The degree of swelling ranges from 25% to 49% depending on composition. Influx of water is often accompanied by an increase in filament diameter (See supplementary figures), particularly for filaments made with Resomer RG 506. Drug is retained in each case, with loading varying with original drug composition. FIG. 30 shows the amount of drug retained in the device relative to the initial formulation. Drug retention after extrusion ranged from 48% to 89% of initial drug depending on formulation conditions. After one day of incubation, all of the fibers display some degree of burst release with post-burst drug retention ranging from 6% to 78% of drug used in formulation.

Drug Release Result

FIG. 31 shows release profiles for each of the filaments separated into groups, with 506-L1 present in each for comparison. FIG. 31a shows the release of 506-L1, -L3, -L4, -L5, and -L6, all devices made from Resomer RG506 with fully dissolved levofloxacin and all with similar release profiles. FIG. 31b shows the release profiles of filaments made from fully dissolved solutions of levofloxacin (506-L1 and 756-L1) and from suspensions of levofloxacin (506-L2 and 756-L2). FIGS. 31c and 506-D2 compared to levofloxacin loaded 506-L1. The differences in release due to polymer type are shown in FIG. 31d, with 506-L1, 756-L1, and PDLLA-L1 all made with identical ratios of polymer:DMSO:levofloxacin and identical processing conditions.

Glass Transition Temperature Result

The glass transitions temperatures for each device under wet and dry conditions are shown in Table 5. After extrusion, glass transition temperatures are depressed below pure polymer values. This depression is more pronounced for devices made of RG 506 and is barely noticeable for PDLLA-L1. In each case, water significantly decreases the glass transition temperature of the devices and the pure polymers. All the glass transition temperatures are essentially the same when the devices are saturated with water, while they vary greatly in the as-made devices when dry. The variation in Tg is almost entirely eliminated after the devices are incubated for one day.

TABLE 5

| | Glass Transition Temperatures | | | |
|---|---|---|---|---|
| | $T_g$ Dry [° C.] | | $T_g$ Wet [° C.] | |
| Sample | As-Made | 1-Day | As-Made | 1-Day |
| RG 506 | 54 | — | 39 | — |
| 506-L1 | 32 | 51 | 37 | 39 |
| 506-L2 | 37 | 54 | 39 | 39 |
| 506-L3 | 30 | 52 | 38 | 39 |

TABLE 5-continued

Glass Transition Temperatures

| Sample | $T_g$ Dry [° C.] | | $T_g$ Wet [° C.] | |
|---|---|---|---|---|
| | As-Made | 1-Day | As-Made | 1-Day |
| 506-L4 | 42 | 54 | 39 | 39 |
| 506-L5 | 23 | 51 | 39 | 38 |
| 506-D1 | 32 | 52 | 39 | 39 |
| 506-D2 | 34 | 54 | 40 | 38 |
| RG756 | 58 | — | 44 | — |
| 756-L1 | 56 | 58 | 44 | 44 |
| 756-L2 | 54 | 57 | 44 | 44 |
| PDLLA | 57 | — | 48 | — |
| PDLLA-L1 | 56 | 57 | 48 | 48 |

Mechanical Properties Results

Figure 32A:
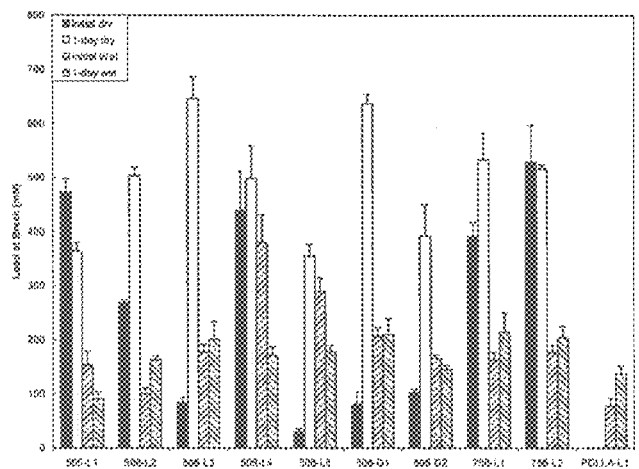
FIGS. 32a and 32b: Provide data graph of mechanical properties of filaments: a) load at break (top) and b) maximum elongation (bottom).
Figure 32B:
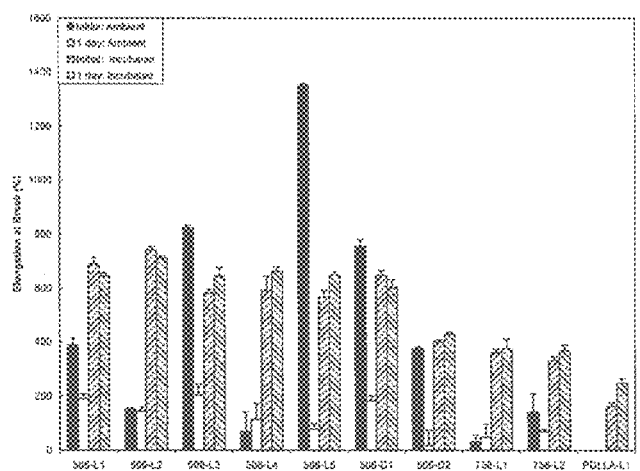

FIG. 32 shows an overview of the mechanical properties of the filaments. FIG. 32a shows the load at break in both ambient (air at 22° C.) and incubated (DPBS at 37° C.) conditions after processing and after 1 day of incubation. Incubated filaments tended to elongate and break consistently, independent of whether they were previously incubated. The variation between initial properties and properties after 1 day of incubation is noticeable under dry conditions, where loads tend to increase and maximum elongation decreases notably.

Analysis

Wet-spinning is a well established process for making polymer filaments and has proven to be a versatile method for therapeutic encapsulation and controlled release, in both previous studies and this current study. The filaments described above are formulated of copolymers with glycolide and d,l-lactide monomers. PLGA copolymers are a good release platform due to the ability to manipulate polymer degradation by changing the ratio of lactide to glycolide. Both drug and polymer were dissolved (or suspended) in DMSO. DMSO was chosen due to its low toxicity, miscibility with water, and ability to dissolve the drugs and polymers used in this study. Other polymers and drugs could easily be processed into similar filaments as long as care was taken with solvent and anti-solvent choice.

In this example, the presence of residual solvent was carefully monitored. Residual DMSO was present in all filaments post-extrusion, but levels were often below detection after a single day of filament incubation in PBS. In the filaments, residual solvent affected both thermal and mechanical properties of filaments at ambient or dry conditions. The difference in glass transition temperatures of dry filaments can be linked to the presence of residual DMSO. Initially, the filaments have residual DMSO, which leads to a depression of Tg and makes the filaments easier to extend. After a day of incubation in PBS, the Tg of the filaments is returned to a value very close to the raw polymer value, while the filaments lose ductility as evidenced by a reduction in elongation at break. The clearest instance of this is the three filaments made with the same formulations but with different coagulation times, 506-L1, L5, and L6. Filament 506-L6 had the shortest coagulation time, followed by 506-L1 and 506-L5. Residual DMSO in 506-L6 was 16.6±3.6 g/cm filament (4.2% by mass), while 506-L1 had 7.6±1.7 g/cm (2.1%) and 506-L5 had 0.5±0.1 g/cm (0.1%). The glass transition temperatures of dry filaments (without incubation) ran 506-L6<506-L1<506-L5 while the elongation at break for the devices in ambient conditions was 506-L6>506-L1>506-L5. However, after a single day of incubation, these properties converged and almost no DMSO was found in any of the devices.

The encapsulation of levofloxacin in copolymers of lactide and glycolide having monomer ratios of 50:50 (RG 506), 75:25 (RG 756), and 100:0 (PDLLA) lactide:glycolide allowed the manipulation of release times for the drugs. Higher lactide content should lead to slower the polymer degradation and drug release. To compare the kinds of PLGA, devices 506-L1, 576-L1 and PDLLA-L1 were made with formulations that were the same except for polymer type. Filaments made from each polymer displayed a typical release curve for such devices, with an initial burst followed by a plateau of slow release that accelerates as the polymer structure degrades. As expected from previous studies, 506-L1 releases over the shortest time period of 15 days, while 756-L1 releases over 40 days, and PDLLA-L1 over 80 days. Device 506-L1 also retains more DMSO than the other two filaments, leading again to differences in thermal and mechanical properties. Even without residual DMSO, glass transition temperatures are different for each polymer, with RG 506 more susceptible to Tg depression by water. Mechanical properties are also different between polymers, with 506-L1 elongating more than 756-L1 or PDLLA-L1. Even after 1 day of incubation, 506-L1 is less brittle than 756-L1 or PDLLA-L1 under ambient or incubated conditions.

The type of drug used in a device and the physical state of drug in the formulation influenced various aspects of the final device. (See, e.g., Zeng, J., et al., Journal of Controlled Release 2005, 105, (1-2), 43-51, the disclosure of which is incorporated herein by reference.) Filaments 506-L2 and 576-L2 were formulated from solutions containing levels of levofloxacin above the solubility point and contained suspended particles of drug, similar to some previously reported fibers. In contrast, filaments 506-L1 and 576-L1 were formulated with less drug (under the same conditions otherwise) with the levofloxacin fully dissolved with the polymer in DMSO. These devices exhibited fast release, with most of the levofloxacin releasing over the course of one day. This burst was so extreme, that only 6% of drug in the formulation was retained after a day of incubation. Even though 506-L2 and 576-L2 had more drug before and immediately after extrusion than 506-L1 and 576-L1, they lost so much levofloxacin during burst release that they were no longer the more highly loaded filaments. These "overloaded" filaments also retained less DMSO than other devices, which had a commensurate influence on mechanical and thermal properties. Filament 506-L4 had even less drug and retained slightly more DMSO, but was otherwise not distinguished from 506-L1. The release profiles from filaments formulated from homogenous levofloxacin solutions were remarkably similar (FIG. 31) leading to the conclusion that formation from dissolved solutions is important for controlling release by polymer degradation.

The type of drug also influences the properties of the filament. Dexamethasone is more soluble in DMSO, and even device 506-D1 was processed from a homogenous solution even though dexamethasone comprised 18.4% of the initial formulation. Dexamethasone is retained in the filament better than levofloxacin. Device 506-D1 retained 89% of formulated drug after extrusion and 78% after a day of incubation in PBS, compared to 53% and 33% respectively for 506-L1. There seems to be a longer lag before release for dexamethasone, perhaps due to its hydrophobicity. Filament 506-D2 was an outlier in several of the above studies, it was more brittle than other 506 devices, released over a longer period, swelled less (only 25% compared to 40%+ for other RG 506 filaments), and was the only filament to have a wet Tg above the native polymer. This is probably due to the extremely high loading of 506-D2, with dexamethasone comprising 42% of the initial filament mass. This surprisingly high filament loading, while retaining mechanical integrity and control of release, was probably due to the extreme solubility of dexamethasone in DMSO and the thermodynamics of coagulation in this system. This shows that highly loaded filaments that are mechanically stable are possible by wet processing as long as the solvent and anti-solvent are chosen carefully.

Conclusion

This example provides evidence of a biodegradable fiber in accordance with the current invention, prepared by a wet-spinning technique, which can be used as a versatile controlled release platform for dexamethasone and levofloxacin. Drug loadings of up to 40% by mass were found achieved, under proper conditions, without sacrificing control of release. The layered nature of the device means that the release rates and mechanical properties of the device can be controlled by polymer selection. This example shows that using the layered multi-component polymer device of the current invention it is possible to create a broad range of devices by wet-spinning, with high drug loading efficiency and mechanical stability, as long as a proper solvent, anti-solvent, and polymer is chosen for a particular drug and desired release profile.

Example #11

Sustained, Ophthalmic Delivery of Levofloxacin

Summary

Eye drops are a standard way of delivering drugs to the eye. However, efficacy suffers from numerous factors that include poor patient compliance, physical difficulties in administering drops, variable drop size, and low residence time in the eye. (See, e.g., Holland, G. N., et al., Am J Opthalmol. 2003; 135(6):867-878; Jampel, H. D., et al., Arch Opthalmol. 2003; 121:540-546; Winfield, A. J., et al., J Opthalmol. 1990; 74(8): 477-480, the disclosures of which are incorporated herein by reference.) Dosing problems are often exacerbated with children due to the necessity of adults administering drops to uncooperative adolescents. (See, e.g., See, e.g., Holland, G. N., et al., Am J Opthalmol. 2003, the disclosure of which is incorporated herein by reference.) Eye drops are rapidly cleared by blinking and reflex Lacrimation, so that only a very small portion of the dose remains available for efficacy. (See, e.g., Kaur, I. P., et al., Drug Development and Industrial Pharmacy 2002; 28(4):353-369; Le Bourlais, C., et al., Progress in Retinal and Eye Research 1998; 17(1):33-58; Robert, P. Y., et al., Drugs 2001; 61(2):175-185, the disclosures of which are incorporated herein by reference.) Additionally, drug concentrations fall rapidly and as such effective levels are not maintained for extended periods of time.

Previous attempts to control the release of drugs to the eye include the fabrication of both biodegradable and non-degradable devices. (See, Kato, A., et al., Invest Opthalmol V is Sci 2004; 45(1):238-244, the disclosure of which is incorporated herein by reference.) The morphologies of these systems include microspheres, tablets, rods, and contact lenses. (See, e.g., Chiang, C. H., et al., J Ocul Pharmacol Ther 2001; 17(6):545-553; Saishin, Y., et al., Invest Opthalmol V is Sci 2003; 44(11):4989-4993; Ceulemans, J., et al., Journal of Controlled Release 2001; 77(3):333-344; Tan, D. T., et al., Opthalmology 1999; 106(2):223-231; Weyenberg, W., et al., Invest Opthalmol V is Sci 2004; 45(9):3229-3233; Weyenberg, W., et al., Journal of Controlled Release 2003; 89(2): 329-340; Theng, J. T. S., et al., Invest Opthalmol V is Sci 2003; 44(11):4895; Pijls, R. T., et al., European Journal of Pharmaceutics and Biopharmaceutics 2005; 59(2):283-288; Zhou, T., et al., Journal of Controlled Release 1998; 55(2-3): 281-295; Alvarez-Lorenzo, C., et al., J Pharm Sci 2002; 91(101:2182-2192; Hiratani, H., et al., Journal of Controled Release 2002; 83(2):223-230, the disclosures of each of which are incorporated herein by reference.) Problems with these systems include irritation, short effective lives, the necessity for device removal (for non-degrading systems and for systems that would cause an adverse reaction in a patient), and premature elimination from the eye.

The goal of this study is to investigate the utility of an implantable, biodegradable layered fiber to control the release of pharmaceuticals to the eye that for certain indications could replace or compliment eye drops. The suture-like morphology of the device allows for easy implantation with a surgical needle. Here, we illustrate the concept by focusing on a device that could provide an alternative to post-operative antibiotic eye drops, and facilitate the treatment of severe external bacterial infections such as bacterial corneal ulcers. The target performance of the device is that it should be easily implanted after surgery, and maintain an effective concentration of the antibiotic in the tear film for 5-10 days. The fiber is anchored in the eye by passing it through the conjunctival tissue and removal surgery is unnecessary by the controlled biodegradibility. Levofloxacin is used as the antibiotic due to its effectiveness against a broad spectrum of bacteria, and the biodegradable polymer is poly(lactide-co-glycolide) (PLGA) with a 50:50 lactide:glycolide ratio. PLGA has been used extensively in implantable devices, including devices implanted in the eye. Levofloxacin not only inhibits bacteria, but is also bacteriocidal, in many cases at concentrations just above the MIC90. Since MIC90 values fall below or are close to 1 g/mL for most bacteria, this value was utilized as the minimum levofloxacin tear concentration that would be acceptable for sustained release. (See, e.g., Davis, R., et al., Drugs 1994; 47(4):677-700, the disclosure of which is incorporated herein by reference.)

Methods

Fiber Preparation

Fibers are synthesized by a wet-spinning procedure. An accurately measured amount of levofloxacin (Sigma Aldrich, St. Louis, Mo.) was placed in a glass vial to which 1.5 g dimethyl sulfoxide (DMSO) were added. This solution was sonicated for 1 minute to facilitate dissolution of levofloxacin. After sonication, 0.5 g PLGA (Resomer RG 506, Boehringer Ingetheim, Ingetheim, Germany) was added to each vial and the vial vortexed to mix all components. The solution was then allowed to equilibrate for 6 hours (vortexing occasionally to mix) to eliminate all trapped bubbles. Three fibers were made for the studies presented in this work. Solutions for fibers A and B were equilibrated at 25° C. and were formulated with 150 and 250 mg of levofloxacin respectively. The solution for fiber C was equilibrated at 60° C. and contained 150 mg of levofloxacin. It should be noted that while formulations A and C were translucently yellow solutions, fiber B had significant amounts of levofloxacin particles remaining.

Solutions A, B or C were loaded into a 5 ml syringe equipped with a 22 gauge flat-tipped needle (Small Parts Inc., Miramar, Fla.) and mounted on a syringe pump. The solutions were extruded into a 16 L water bath (22±2° C.) and taken up onto a 1 inch bobbin rotated by a DC gear motor. The solutions were extruded at 70 L/min and the fiber was taken up at a rotation rate of 8.0 RPM (measured by a tachometer), at a draw ratio of 1.2. The fibers were allowed to coagulate for 45 seconds. Fibers were secured tautly without stretching and allowed to dry under ambient conditions for two days.

Fiber Characterization

Bulk fiber morphology was observed by light microscopy and scanning electron microscopy (SEM). Light microscopy was performed using a Micromaster I light microscope (Fisher Scientific, Pittsburgh, Pa.) at 10× magnification. The size measurements were calibrated using known diameter wires (Small Parts Inc.). For SEM, samples were coated with Pt/Pd and magnifications up to 400× were possible without destroying the samples.

Total drug loading of the fibers was determined by dissolving the fiber with 1 M NaOH. The levofloxacin content of the resulting solution was measure by using high performance liquid chromatography (HPLC) with a C18 column (Agilent 1200 series HPLC). The mobile phase was 49.95% water, 49.95% acetonitrile with 0.1% trifluorbacetic acid. Levofloxacin content was determined by fluorescence with an excitation at 292 nm and emission at 494 nm.

In-Vitro Release

One inch sections of fiber were placed in 1.5 mL tubes. One mL of phosphate buffered saline (pH 7.4) at 37° C. was added to each vial. The tubes were incubated at 37° C. under gentle rocking and at various times, the buffer was replaced with fresh PBS. The removed PBS was analyzed for levofloxacin content by HPLC as described above.

In-Vitro Mechanical Testing

Stress vs. strain curves for the fibers were collected on an Instron 1150 mechanical properties testing apparatus (Instron, Norwood, Mass. Samples were submerged in PBS at 37° C. on an incubator and removed at various times. The diameter of a sample was measured by light microscopy and mounted on the Instron. The sample was submerged in PBS at 37° C. and was drawn at a strain rate of 1%/sec. The tensile stress for each polymer was recorded.

In-Vivo Implantation

All use of animals in these experiments adheres to the ARVO Statement for the Use of Animals in Ophthalmic and Vision Research and were approved by the California Institute of Technology Institutional Animal Care and Use Committee.

Fibers were prepared and dried for two days as described above. The day of implantation, they were sterilized by dipping in isopropanol followed by dipping in sterile saline. New Zealand white rabbits were anesthetized with isoflurane (5% originally, falling to 2.5% typically) and their eyes were treated with 0.5% proparicaine drops. A speculum was used to hold open the eyelids while implantation was accomplished. Fiber was threaded through a standard surgical needle creating a double-stranded device. The free end of the fiber was knotted and the needle was passed under the conjunctiva in the inferior fornix until the knot rested against the tissue. The needle was returned close to the initial position and passed a second time under the tissue, leaving an exposed stand of about 1.5 cm above the tissue and in contact with the tear film. The fiber was knotted again at the exit point of the tissue so as to secure the device at both ends with knots. The length of the fiber before implantation and the remainder after implantation were accurately measured to give the length of fiber implanted. Six implantations of each type of fiber were performed.

Tear samples were collected by Schrimer's test strip. The mass of a strip before and after 15 s contact with the tear film was recorded. The strip was allowed to dry and then the drug on the strip was dissolved in 200 L PBS. The sample was filtered and levofloxacin concentration was determined by HPLC. The tear concentration measurements were normalized to the average length of fiber implanted. For each tear sample, the presence of fiber was verified by visual observation. The failure point of the fiber was recorded at the first day where no fiber was visible on the surface of the tissue.

To further correlate in-vitro models with in-vivo performance, samples of fiber C that had been incubated for two days in-vitro were implanted in three rabbits. Fiber C was made as above and three lengths of approximately 30 cm (accurately measured) were cut and each was placed in 10 mL of PBS at 37° C. For two days, these fibers were incubated at 37° C. like for the in-vitro experiments described above. After two days, the fibers were removed from the PBS, sterilized with isopropanol, and implanted in rabbits.

After 9 days, the rabbits were anesthetized and the area around the implantation was examined for fiber remnants. In most cases, no remnants could be found, since fiber failure and elimination usually involved the entire fiber coming out of the tissue. In some cases, when a fiber remnant could be positively identified, a biopsy of the site was taken for analysis. These samples were sent for blinded, professional histological analysis and a report detailing inflammation, foreign body reaction, and other histology features was generated.

Results

Fibers were prepared by wet-spinning and have diameters that are listed in Table 6. Representative SEMs of the fiber are shown in FIG. 33 The fiber cross section for fiber A is provided and shows the internal porosity of the polymeric fibers. The other fibers reveal essentially the same cross sectional morphology. On the other hand the exterior surfaces of the fiber are different and each is illustrated in FIG. 33. Fibers A and C have a rough surface on the sub-micron length scale. Larger surface roughness is apparent for fiber B. The presence of the larger protuberances in fiber B could be related to the large drug loading in this fiber (see below).

Table 6 lists the concentrations of levofloxacin for each of the three fibers. Fiber B that was formulated with 1.67 times as much levofloxacin as A and C, has a significantly higher drug loading (ca. 2×) than the other two fibers. Each fiber has a very similar diameter (Table 6), which is expected due to their processing under identical extrusion conditions

TABLE 6

Fiber Properties

| | Diameter [mm] | Loading [μg/cm] | (μg levofloxacin/ gm tear at 3 hr) | Avg. Failure Time In-vivo [days] |
|---|---|---|---|---|
| Fiber A | 0.27 | 46 ± 2 | 48 ± 33 | 7.3 ± 0.5 |
| Fiber B | 0.28 | 85 ± 4 | 171 ± 140 | 8.3 ± 0.8 |
| Fiber C | 0.26 | 36 ± 2 | 30 ± 17 | 6.8 ± 0.7 |

Figure 34:
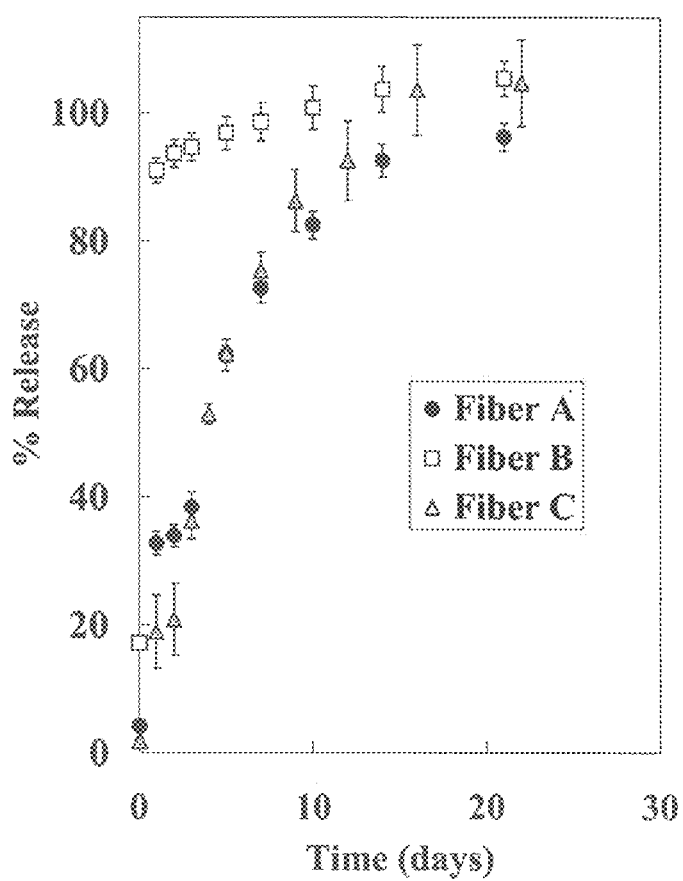
FIG. 34: Provides a data graph of levofloxacin release as a function of incubation time for each fiber.

FIG. 34 shows the in-vitro levofloxacin release for each of the fibers. Fiber B reveals a quick release, while fibers A and C show a burst release for the first day, followed by a plateau from days 1-3, and then ends with a faster release until completion.

Figure 35:
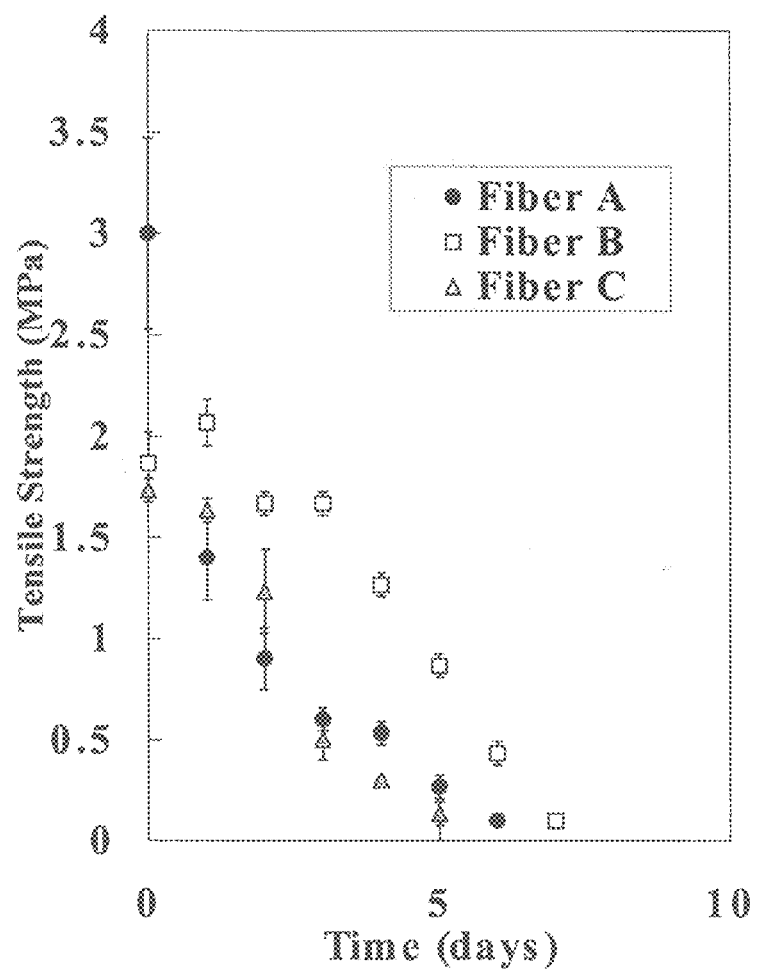
FIG. 35: Provides a data graph of in-vitro ultimate strength of each fiber under physiological conditions over incubation time.

The in-vitro tensile strength of the fibers decreases with incubation time when tested in PBS at 37° C. (FIG. 35). Fiber B maintains strength the longest, followed by fiber A and fiber C. All of the fibers last at least 5 days before they are no longer strong enough to handle without breaking.

Figure 36:
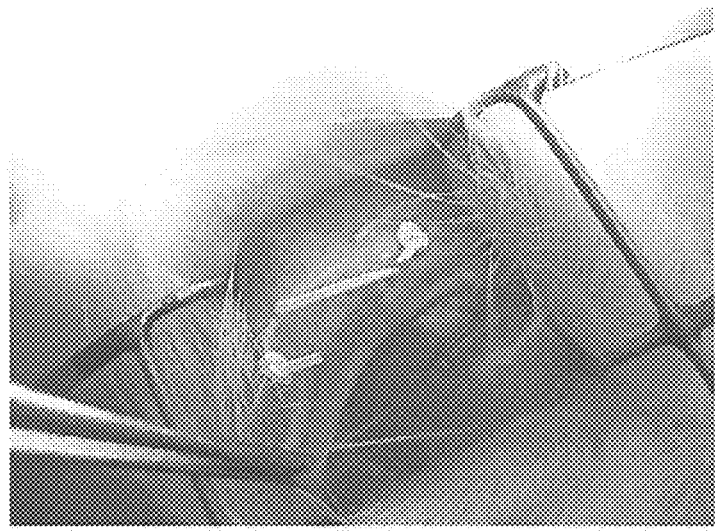
FIG. 36: Provides a photograph of an implanted fiber shown immediately after implantation.

The fibers were implanted into the eyes of New Zealand white rabbits as illustrated in FIG. 36 with a tear-exposed strip and knots at the ends. The average length of implantation was 9.9±1.8 cm. Levels of levofloxacin in the tears were tested 3 hours after implantation, and then every day until the end of the trial. The fibers were allowed to fall out on their own and every day, when tears were sampled, the eyes were examined to determine exposed fiber presence. Device failure occurs when the polymer degrades to a point where the device breaks and falls out of the eye and can no longer be seen by simple observation. Table 6 listed the average time to device failure for each of the fibers. Fiber B lasts longer than fiber A, with fiber C failing the earliest. Some fibers would extrude out of the tissue and fall out in entirely, while others left small pieces of fiber embedded in the tissue.

After 3 hours, there were high levels of levofloxacin in the tears of each animal for all the fibers implanted, with the highest levels for fiber B (Table 6). The time dependent levofloxacin tear concentrations are shown in FIG. 37 where the concentrations are normalized to the average implantation length to eliminate bias from variations in the amounts implanted. The plots are shown on the semi-log scale to accentuate trends in the tear concentrations. Data points after device failure are omitted, though tear concentrations typically fell below detection levels when no fiber was visibly present. Fiber A exhibits stable release, with most values falling between 1 and 10 mg levofloxacin/g tear. Fiber B shows significantly lower concentrations for the majority of samples. Fiber C has a release profile that varies with time, showing a dip at 1 day, rising concentrations through day 3, then a gradual decline until device failure.

There were visible signs of irritation to the eyes immediately after implantation, but these signs dissipated as the rabbits fully recovered from the surgery. By day 2, there were no visible signs of irritation or pain (no scratching, rubbing, or keeping the eye shut). After nine days, examination revealed the discernable remnants of only 5 of the fibers that were implanted. Histology of biopsies from these sites revealed chronic inflammation in all samples with foreign body reaction and fibrosis each present in three out of the five samples. Inflammatory cells made up of lymphocytes, plasma cells and eosinophils were present in the subepithelial stroma for all of the samples and foreign body giant cells were seen in three of the samples. This type of tissue response is in agreement with previous studies on implanted PLGA and other degradable devices. (See, e.g., Aderriotis, D., et al., J Can Dent Assoc 1999; 65(6):345-347; Kohn, J.; Abramson, S., et al., Biodegradable and Bioerodible Materials. In Biomaterials Science Second Edition, Elsevier Academic Press: San Diego, Calif., 2004:115-127; Cleland, J. L., et al., Journal of Controlled Release 1997; 49(2-3):193-205; Giordano, G. G., et al., Invest Opthalmol V is Sci 1993; 34(9):2743-51; Jones, K. S., Semin Immunol 2008; 20(2):130-136, the disclosures of which are incorporated herein by reference.)

Figure 38:
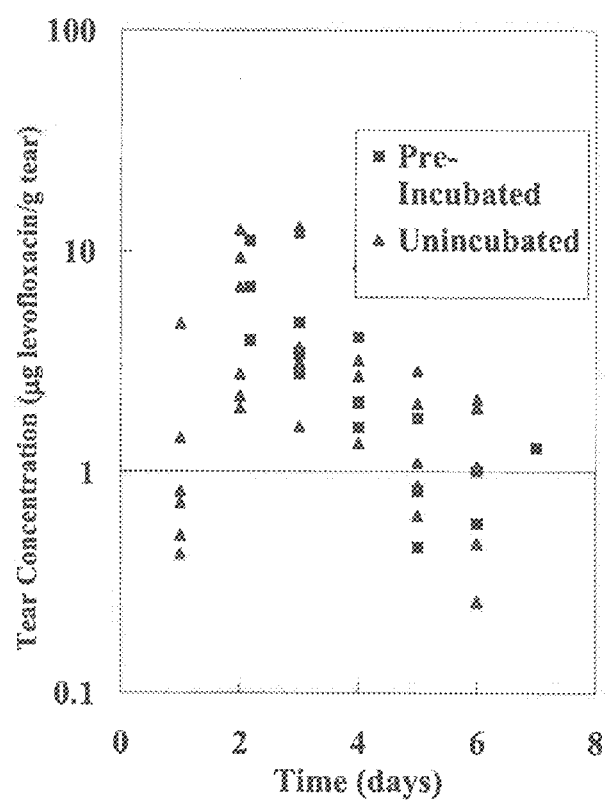
FIG. 38: Provides a data graph showing a comparison of in-vivo levofloxacin tear concentrations between fiber C that was implanted as-made and fiber C that was incubated in PBS at 37° C. for two days before implantation.

The transient release profile of fiber C allowed further investigation into the relationships between the in-vitro and in viva results by incubating samples of fiber C for two days in PBS at 37° C. before implantation. FIG. 38 shows the results of this study, with the samples for the pre-incubated fiber shifted to match the timeframe of the fiber implanted without incubation, so time 0 on the graph corresponds to when unincubated fiber C was implanted in the rabbits and when pre-incubated fiber C was placed in PBS. Pre-incubated fiber C was then implanted on day 2. The pre-incubated fibers show levofloxacin concentrations that match well to the original fibers, and the release profiles correlate with the same gradual decline until failure. The pre-degraded fibers also failed after an average of 4 days, matching the average lifespan of original fibers minus the two day incubation period.

Discussion

Biodegradable layered fibers for the controlled release of levofloxacin to the eye have been prepared and characterized both in vitro and in vivo in the eyes of New Zealand white rabbits. Levofloxacin is a highly potent antibiotic against a broad spectrum of microbes (under 1 g/mL in the vast majority of cases) and is FDA approved for topical, ophthalmic use. (See, e.g., Baltch, A. L., et al., Antimicrob Agents Chemother 1995; 39(8):1661-1666, the disclosure of which is incorporated herein by reference.) Levofloxacin is a good model drug for this delivery system since it is easily detectable in low concentrations due to its natural fluorescence. The system under investigation here is not specific to levofloxacin, and we have prepared fibers with other antibiotics and drug types such as steroids. PLGA is a commonly used polymer in drug delivery devices and biodegradable sutures. (See, e.g., Wang, Y., et al., Biomaterials 2004; 25(18):4279-4285; Alexis, F., Polymer International 2005; 54(1):36-46; and Kenley, R. A., et al., Macromolecules 1987; 20(10):2398-2403, the disclosures of which are incorporated herein by reference.) The PLGA-levofloxacin fibers are prepared by wet-spinning, which creates a soft, flexible product that aids in the minimization of irritation upon implantation. (See e.g., Nelson, K. D., et al., Tissue Engineering 2003; 9(6) 1323-1330, the disclosure of which is incorporated herein by reference.) The diameters of these fibers are similar to suture diameters, with these three fibers having diameters typical for a size 2-0 or 3-0 suture. While this is larger than sutures typically used for ophthalmic applications, it is similar to the dimensions of previously described ophthalmic controlled release devices, including some that have been used clinically. (See, e.g. Sihvola, P., et al., Acta Opthalmol Scand Suppl 1980; 58(6):933-7, the disclosure of which is incorporated herein by reference.)

Wet-spinning fibers from a solution of levofloxacin and PLGA results in a product that is porous with a rough surface (on the sub-micron length scale). The internal morphology of the fiber is consistent with fiber prepared in previous work via wet-spinning. (See, e.g., Gao, H., et al., Journal of Controlled Release 2007; 118(3):325-332, the disclosure of which is incorporated herein by reference.) The protuberances on the surface of the fiber are likely the result of the drug forming aggregates on the surface, and/or by the drug distorting the polymer matrix at the surface. Fiber B has larger more discrete protuberances relative to fibers A and C. This may be due to fiber B having suspended particles of drug present in the polymer solution before wet spinning. Fiber A was formulated just below the saturation concentration of levofloxacin in DMSO and no suspended drug aggregates were observed in the extruded solution. Fiber C was manufactured at an elevated temperature to absolutely assure total drug dissolution in the polymer/DMSO solution. Drug stability under these conditions could be a concern, but levofloxacin retention times on the HPLC did not change after formulation at higher temperatures, no other peaks were observed in the HPLC chromatogram, and it has been previously reported that levofloxacin is stable under autoclaving conditions. (See e.g., Fujimoto, K., et al., Jpn J Pharmacol 1995; 69(4):443-445, the disclosure of which is incorporated herein by reference.)

The differences in formulation are reflected in drug loading. Fiber B has significantly greater drug loading due to the larger amount of drug present in the initial formulation. Fiber A has slightly higher drug loading than fiber C, that may be caused by the differences in formulation temperature affecting drug diffusion during the wet-spinning procedure. These drug loadings are high when compared to the overall masses of the fibers. Fiber A is 12% levofloxacin by mass, compared to 23% and 11% for fibers B and C respectively. For a typical implantation, the total amount of levofloxacin in the implanted length of fiber ranged from 300-750 g, depending on the type of fiber.

The time dependent release properties from in-vitro studies correlated well with in vivo results. For fibers A and C, the release profile involved an initial burst followed by a small plateau and a second phase of release. These results are similar to many previous studies of devices fashioned from PLGA or related polymers. (See, e.g., Siepmann, J., et al., Advanced Drug Delivery Reviews 2001; 48(2-3):229-247, the disclosure of which is incorporated herein by reference.)

The initial burst of antibiotic release is clinically desirable as high antibiotic concentration is most important during the time immediately after an operation. The first phase of release is normally diffusion controlled and fast, while the second phase is typically degradation controlled and is determined by the kinetics of polymer chain cleavage. If this is the case for the fibers investigated here, fiber B displays almost complete diffusion controlled release, probably due to the precipitated levofloxacin in the formulation. This result is consistent with the work of Gao et al., who found that suspending drug particles in a fiber leads to high burst release that is independent of fiber degradation. (See, e.g., Gao, H., et al., Journal of Controlled Release 2007, 118, (3), 325-332, the disclosure of which is incorporated herein by reference.) The differences in the release behavior in the in-vitro release kinetics are also observed in the in-vivo tear concentrations. Fibers A and C provide relatively high levels of drug over the entire time course of the study while fiber B shows mostly low levels of drug after one day. Tears were sampled by contacting the eye with Schirmer's test strips (mass determinations are more accurate than volume and thus were used here). This method may be affected by reflex lacrimation diluting the tear samples as they are collected, resulting in levofloxacin concentration readings that are lower than actual levels in the tear film. The Schirmer's strips were used since alternatives, such as capillary tubes and sterile sponges also suffered from similar problems and were more difficult to use for collection. Topical anesthesia, that would prevent reflex lacrimation, cannot be used for tear collection, since any infusion of drops into the eye would wash out the levofloxacin.

One of the primary goals of a local drug delivery system is to minimize the amount of drug used in the dose while maximizing the effectiveness of the dose. For fibers of the type used here, these criteria translate into maintaining an effective level of levofloxacin while minimizing the total exposure. Any side effects or tissue toxicity due to levofloxacin exposure should be minimized while effectiveness is retained. For fiber A, the ability to maintain effective levels of levofloxacin has been demonstrated, while the total amount of levofloxacin present in a particular eye averages only 455 g. Eye drops, which maintain effective levels of drug in the eye for only a short time, require a far larger total amount of drug. For example, a typical drop of 0.5% levofloxacin contains approximately 250 g of drug (assuming a standard drop of 0.05 ml). Thus, the total amount of drug in a standard implantation of fiber A is equivalent to the total drug content of only two drops of levofloxacin ophthalmic solution.

Overall, the fibers were easy to implant with the procedure taking only a couple of minutes for each eye. The rabbits showed some irritation in the time immediately after implantation, but they recovered from the implantation and eyes with fibers implanted were not immediately discernable from eyes without fibers. With few exceptions, the eyes with fibers did not display excessive tearing and none of the rabbits were observed trying to scratch or rub the implantation site. The 50:50 PLGA that was used for these studies in not often fashioned into filaments, but other reported devices made by wet-spinning have been described. The polymer is amorphous, and devices made from amorphous polymers can be very brittle and rigid. These fibers, made by wet spinning, easily yield under wet conditions as shown by the low maximum stress obtained during mechanical properties testing (data not shown). Moreover, these maximum stresses are often achieved as strains of over 500% that indicate the fibers tend to deform in response to stress rather than recoil. The low irritation could be the result of the easy yielding of the fibers to stress, thus preventing any pinching or tightening that could result from a device retracting against any forces acting on the devices in the eye. The irritation may also be lessened by the porosity of the fibers, which makes the devices able to deform in the radial direction. While the rabbit results are promising in that the fibers are well tolerated, humans may respond differently to such a device. Implantation technique and size may need to be further tuned. For example, the practice of knotting the ends of the fibers may need to be re-evaluated based on patient concerns and another method of securing the ends of the filaments may need to be devised.

After the fiber has been eliminated, histology reveals that the part of the fiber embedded in the conjunctiva does cause an inflammation and foreign body response. This inflammation is of a moderate intensity and is similar to the types of inflammation seen in response to degrading sutures and other degradable implants. (See, e.g., Aderriotis, D., et al., J Can Dent Assoc 1999; 65(6):345-347; Kohn, J., et al., Biodegradable and Bioerodible Materials. In Biomaterials Science Second Edition, Elsevier Academic Press: San Diego, Calif., 2004:115-127; Cleland, J. L., et al., J of Controlled Release 1997; 49(2-31:193-205; Daugherty, A., et al., Journal of Controlled Release 1997; 49(2-31:193-205; and Giordano, G. G., et al., Invest Opthalmol V is Sci 1993; 34(91:2743-51, the disclosures of which are incorporated herein by reference.) PLGA devices have been approved for human implantation by the FDA despite the inflammation caused by degradation products of the fiber. (See, Kohn, J., et al., Biodegradable and Bioerodible Materials. In Biomaterials Science Second Edition, Elsevier Academic Press: San Diego, Calif., 2004:115-127, the disclosure of which is incorporated herein by reference.) Since this inflammation is moderate, localized only to the tissue in contact with the embedded part of the fiber, and is only for devices that are not fully eliminated after fiber failure, it may be that most of the reaction can be eliminated by changing the implantation technique. If future implants only have a small length embedded in the tissue, with most of the fiber on the tissue surface, then there is less area for inflammation and not much embedded fiber to prevent complete device elimination.

Previous attempts at sustained drug delivery to the tear film have mostly focused on shorter release times and devices that extend drug residence times when the drug is administered as a drop. Diffusion based drug delivery systems, such as contact lenses, unanchored devices, and self-forming gels, are often used to stall the release of drug for several hours, but rarely work for multiple days. (See, e.g., Weyenberg, W., et al., Journal of Controlled Release 2003; 89(2):329-340; Theng, J. T. S., et al., Pharmacokinetic and Toxicity Study of an Intraocular Cyclosporine DDS in the Anterior Segment of Rabbit Eyes. Invest Opthalmol V is Sci 2003; 44(11):4895; Piils, R. T., et al., Journal of Pharmaceutics and Biopharmaceutics 2005; 59(2):283-288; Alvarez-Lorenzo, C., et al., J Pharm Sci 2002; 91(10):2182-2192; Hiratani, H., et al, Journal of Controlled Release 2002; 83(2):223-230; and Robert, P. Y. et al., Drugs 2001; 61(2):175-185, the disclosures of which are incorporated herein by reference.) There have been reports of molecularly imprinted contact lenses that release drug for several days, but they must reside on the cornea, and this may limit their use for immediately after surgery on the cornea. Other systems that are not anchored may be placed in the conjunctival sac, but can come out due to mechanical disturbances. These devices may show promise in-vitro for multiple-day release, but will ultimately have to be anchored in-vivo.

Devices developed for drug delivery to the tear film that are unanchored will be cleared from the eye due to blinking or other types of mechanical disturbance. (See, Piils, R. T., et al., Journal of Pharmaceutics and Biopharmaceutics 2005; 59(2): 283-288, the disclosure of which is incorporated herein by reference.) The fibers are self-anchoring, so they must maintain mechanical strength over the course of drug release. Eyes that had no visible fiber also had no detectable levels of levofloxacin, so the ability of the fiber devices shown here to reside exposed to the tear film was of critical importance. At the same time, a device that resides in the eye long past the end of drug release is undesirable. The fibers described here have mechanical properties that are time dependent due to the biodegradation of the PLGA. In-vitro studies of mechanical properties closely predict the in-vivo lifespan of the fibers. The order of survival (B>A>C) is especially important, but the days to failure are even closer in agreement for the in-vitro and in-vivo studies. In-vivo failure tends to happen about a day later than predicted in-vitro, but this is probably due to the method of recording failure in-vivo (only looking at tear sampling times) and to fibers remaining trapped in the eye past their mechanical failure point. A critical consideration in the design of the fibers is that the mechanisms for drug release and mechanical failure are not independent. This leads to a fiber releasing over 70% of its total drug load before failure in-vitro.

Another significant benefit of the fibrous morphology of this system is the ease of removal after implantation. Since fibers maintain mechanical strength for several days, they could be easily cut and removed should the patient experience adverse affects due to interactions with either the fiber material or delivered drug. This ease of removal is a property of the bulk morphology of the device and the type of implantation. Since the ends of the fiber, and a loop in the center, are exposed on the tissue surface, a physician would be able to simply cut the central loop and pull the entire device out by the ends. This procedure takes less than a minute to complete based on informal testing performed during these experiments. The ease of removal is in contrast to other systems, since fully implanted devices would require a second surgery to remove. Microparticulate devices are not easily removed due to the difficulty in finding and eliminating all particles when the devices are small and able to migrate.

The implantation of a fiber that was pre-incubated in-vitro further shows the validity of the in-vitro models used for this system. The transient in-vivo tear concentrations for fiber C had the largest variation and thus made this fiber the most appropriate one to investigate variation in the time dependent release properties. The pre-incubated fiber has the same release profile as fiber C implanted without any incubation when adjusted two days to account for the overall incubation time. Moreover, the pre-incubated fiber fails two days earlier than the un-incubated one.

Conclusions

Biodegradeable fibers (PLGA) for controlled delivery of levofloxacin to the eye have been demonstrated with this example. Specifically, these devices have been shown to release effective levels of levofloxacin over 5-10 days have been achieved, with tear concentrations above 1 g levofloxacin/g tear from the eyes of New Zealand white rabbits obtained for up to 7 days. The fiber material is fully absorbable, and the total residence time of the device in the eye varies from 5-9 days, depending on formulation. In-vitro, fibers A and C release levofloxacin in a sustained manner over 10-15 days, while fiber B quickly released levofloxacin (over 90% released in the first day) The tensile strength of all the fibers decreases over time and maintains measurable strength for 5-7 days in PBS at 37° C. The in-vivo tear concentrations of levofloxacin in rabbit eyes are in general agreement with the results from the in-vitro release profiles, with one of the fibers (fiber A) showing levels of levofloxacin in the tears for 6 days that are expected to have antimicrobial effects. The fibers are generally well tolerated with no overt signs of irritation or discomfort after recovery from the initial surgery. Histology from tissue taken directly adjacent to degrading fiber reveals localized inflammation and immune response consistent with previously described PLGA devices. Fiber failure occurs at 6-8 days within the rabbit eyes.

This example demonstrates that drug delivery can be applied to other drugs with different target release spans and that biodegradable fibers are an effective way of delivering therapeutics to the eye.

REFERENCES

All patents, publications, and references cited in the foregoing disclosure are expressly incorporated herein by reference. The following references are expressly incorporated herein: Batycky, R. P., Hanes, J., Langer, R., and Edwards, D. A., A theoretical model of erosion and macromolecular drug release from biodegrading microspheres. Journal of Pharmaceutical Sciences 1997, 86, (12), 1464-1477; Nelson, K. D., Romero, A., Waggoner, P., Crow, B., Borneman, A., and Smith, G. M., Technique paper for wet-spinning Poly(L-lactic acid) and poly(DL-lactide-co-glycolide) monofilament fibers. Tissue Engineering 2003, 9, (6), 1323-1330; Bb Crow, P. D., Borneman, A. F., Hawkins, D. L., Smith, G. M., and Nelson, K. D., Evaluation of in Vitro Drug Release, pH Change, and Molecular Weight Degradation of Poly(L-lactic acid) and Poly(D, L-lactide-co-glycolide) Fibers. TISSUE ENGINEERING 2005, 11, (7/8); Gao, H., Gu, Y., and Ping, Q., The implantable 5-fluorouracil-loaded poly(L-lactic acid) fibers prepared by wet-spinning from suspension. Journal of Controlled Release 2007, 118, (3), 325-332; Zilberman, M., Nelson, K. D., and Eberhart, R. C., Mechanical Properties and In Vitro Degradation of Bioresorbable Fibers and Expandable Fiber-Based Stents. J Biomed Mater Res Part B: Appl Biomater 2005, 74, 792-799; Kohn, J., Abramson, S, and Langer, R., Biodegradable and Bioerodible Materials. In Biomaterials Science Second Edition, Ratner, B., Hoffman, A., Schoen, F., and Lemons, J., Eds. Elsevier Academic Press: San Diego, Calif., 2004; pp 115-127; Langer, R., Biomaterials and biomedical engineering. Chemical Engineering Science 1995, 50, (24), 4109-4121; Alexis, F., Factors affecting the degradation and drug-release mechanism of polyllactic acid) and poly(Lactic acid)-co-(glycolic acid). Polymer International 2005, 54, (1), 36-46; J.; Gopferich, A., Mathematical modeling of bioerodible, polymeric drug delivery systems. Advanced Drug Delivery Reviews 2001, 48, (2-3), 229-247; Batycky, R. P., Hanes, J., Langer, R., and Edwards, D. A., A theoretical model of erosion and macromolecular drug release from biodegrading microspheres. Journal of Pharmaceutical Sciences 1997, 86, (12), 1464-1477; Freiberg, S, and Zhu, X. X., Polymer microspheres for controlled drug release. International Journal of Pharmaceutics 2004, 282, (1-2), 1-18; Wang, Y., Challa, P. and Epstein, D. L., Controlled release of ethacrynic acid from poly(lactide-co-glycolide) films for glaucoma treatment. Biomaterials 2004, 25, (18), 4279-4285; Kim, K., Luu, Y. K., Chang, C., Fang, D., Hsiao, B. S., Chu, B. and Hadjiargyrou, M., Incorporation and controlled release of a hydrophilic antibiotic using poly(lactide-co-glycolide)-based electrospun nanofibrous scaffolds. Journal of Controlled Release 2004, 98, (1), 47-56; Kenawy, E. R., Bowlin, G. L., Mansfield, K., Layman, J., Simpson, D. G., Sanders, E. H. and Wnek, G. E., Release of tetracycline hydrochloride from electrospun poly(ethylene-co-vinylacetate), poly(lactic acid) and a blend. Journal of Controlled Release 2002, 81, (1-2), 57-64; Zeng, J., Yang, L., Liang, Q., Zhang, X., Guan, H., Xu, X., Chen, X. and Jing, X., Influence of the drug compatibility with polymer solution on the release kinetics of electrospun fiber formulation. Journal of Controlled Release 2005, 105, (1-2), 43-51; Crow, B. B., Borneman, A. F., Hawkins, D. L., Smith, G. M. and Nelson, K. D., Evaluation of in Vitro Drug Release, pH Change, and Molecular Weight Degradation of Poly(L-lactic acid) and Poly(D, L-lactide-co-glycolide) Fibers. TISSUE ENGINEERING 2005, 11, (7/8); Crow, B. B. and Nelson, K. D., Release of bovine serum albumin from a hydrogel-cored biodegradable polymer fiber. Biopolymers 2006, 81, (6), 419-427; Gao, H., Gu, Y. and Ping, Q., The implantable 5-fluorouracil-loaded poly(l-lactic acid) fibers prepared by wet-spinning from suspension. Journal of Controlled Release 2007, 118, (3), 325-332; Zilberman, M., Nelson, K. D. and Eberhart, R. C., Mechanical Properties and In Vitro Degradation of Bioresorbable Fibers and Expandable Fiber-Based Stents. J Biomed Mater Res Part B: Appl Biomater 2005, 74, 792-799; Fridrikh, S. V., Yu, J. H. and Brenner, M. P.; Rutledge, G. C., Controlling the Fiber Diameter during Electrospinning. Physical Review Letters 2003, 90, (14), 144502; Subbiah, T., Bhat, G. S., Tock, R. W., Parameswaran, S, and Ramkumar, S. S., Electrospinning of nanofibers. Journal of Applied Polymer Science 2005, 96, (2), 557-569; Holland, G. N. and Stiehm, E. R., Special considerations in the evaluation and management of uveitis in children. Am J Opthalmol. 2003; 135(6):867-878; Jampel, H. D., Schwartz, G. F. and Robin, A. L., et al., Patient Preferences for Eye prop Characteristics A Willingness-to-Pay Analysis. Arch Opthalmol. 2003; 121:540-546; Winfield, A. J., Jessiman, D., Williams, A. and Esakowitz, L., A study of the causes of non-compliance by patients prescribed eyedrops. Br J Opthalmol. 1990; 74(8):477-480; Kaur, I. P. and Smitha, R., Penetration enhancers and ocular bioadhesives: Two new avenues for ophthalmic drug delivery. Drug Development and Industrial Pharmacy 2002; 28(4):353-369; Le Bourlais, C., Acar, L., Zia, H., et al., Ophthalmic drug delivery systems—Recent advances. Progress in Retinal and Eye Research 1998; 17(1): 33-58; Robert, P. Y. and Adenis, J. P., Comparative review of topical ophthalmic antibacterial preparations. Drugs 2001; 61(2):175-185; Kato, A., Kimura, H., Okabe, K., et al., Feasibility of drug delivery to the posterior pole of the rabbit eye with an episderal implant. Invest Opthalmol V is Sci 2004; 45(1):238-244; Chiang, C. H., Tung, S. M., Lu, D. W. and Yeh, M. K., In vitro and in vivo evaluation of an ocular delivery system of 5-fluorouracil microspheres. J Ocul Pharmacol Ther 2001; 17(6):545-553; Saishin, Y., Silva, R. L., Callahan, K., et al., Periocular injection of microspheres containing PKC412 inhibits choroidal neovascularization in a porcine model. Invest Opthalmol V is Sci 2003; 44(11):4989-4993; Ceulemans, J., Vermeire, A., Adriaens, E., Remon, J. P. and Ludwig, A., Evaluation of a mucoadhesive tablet for ocular use. Journal of Controlled Release 2001; 77(3):333-344; Tan, D. T., Chee, S. P., Lim, L. and Lim, A. S., Randomized clinical trial of a new dexamethasone delivery system (Surodex) for treatment of post-cataract surgery inflammation. Opthalmology 1999; 106(2):223-231; Weyenberg, W., Vermeire, A., Dhondt, M. M. M., et al., Ocular bioerodible minitablets as strategy for the management of microbial keratitis. Invest Ophthalmol V is Sci 2004; 45(9):3229-3233; Weyenberg, W., Vermeire, A., Remon, J. P. and Ludwig, A., Characterization and in vivo evaluation of ocular bioadhesive minitablets compressed at different forces. Journal of Controlled Release 2003; 89(2):329-340; Theng, J. T. S., Ei, T. S, and Zhou, L., et al., Pharmacokinetic and Toxicity Study of an Intraocular Cyclosporine DDS in the Anterior Segment of Rabbit Eyes. Invest Ophthalmol V is Sci 2003; 44(11):4895; Puils, R. T., Sonderkamp, T. and Daube, G. W., et al., Studies on a new device for drug delivery to the eye. European Journal of Pharmaceutics and Biopharmaceutics 2005; 59(2):283-288; Zhou, T., Lewis, H., Foster, R. E. and Schwendeman, S. P., Development of a multiple-drug delivery implant for intraocular management of proliferative vitreoretinopathy. Journal of Controlled Release 1998; 55(2-3):281-295; ALvarez-Lorenzo, C., Hiratani, H. and Gomez-Amoza, J. L., et al., Soft contact lenses capable of sustained delivery of timolol. J Pharm Sci 2002; 91(10):2182-2192; Hiratani, H. and Alvarez-Lorenzo, C., Timolol uptake and release by imprinted soft contact lenses made of N,N-diethylacrylamide and methacrylic acid. Journal of Controlled Release 2002; 83(2):223-230; Davis, R. and Bryson, M., Levofloxacin: A review of its antibacterial activity, pharmacokinetics and therapeutic efficacy. Drugs 1994; 47(4):677-700; Aderriotis, D. and Sandor, G. K. B., Outcomes of Irradiated Polyglactin 910 Vicryl Rapide Fast-Absorbing Suture in Oral and Scalp Wounds. J Can Dent Assoc 1999; 65(6):345-347; Kohn, J., Abramson, S, and Langer, R., Biodegradable and Bioerodible Materials. Ratner, B., Hoffman, A., Schoen, F. and Lemons, J., Eds. Biomaterials Science Second Edition, Elsevier Academic Press: San Diego, Calif., 2004:115-127; Cleland, J. L., Duenas, E., Daugherty, A., et al., Recombinant human growth hormone poly(lactic-co-glycolic acid)(PLGA) microspheres provide a long lasting effect. Journal of Controlled Release 1997; 49(2-3):193-205; Giordano, G. G., Refojo, M. F. and Arroyo, M. H., Sustained delivery of retinoic acid from microspheres of biodegradable polymer in PVR. Invest Opthalmol V is Sci 1993; 34(9):2743-51; Jones, K. S., Effects of biomaterial-induced inflammation on fibrosis and rejection. Semin Immunol 2008; 20(2):130-136; Baltch, A. L., Smith, R. P. and Ritz, W., Inhibitory and Bactericida) Activities of Levofloxacin, Ofloxacin, Erythromycin, and Rifampin Used Singly and in Combination against Legionella-Pneumophila. Antimicrob Agents Chemother 1995; 39(8):1661-1666; Wang, Y., Challa, P. and Epstein, D. L., Controlled release of ethacrynic acid from poly(lactide-co-glycolide) films for glaucoma treatment. Biomaterials 2004; 25(18): 4279-4285; Alexis, F., Factors affecting the degradation and drug-release mechanism of poly(lactic acid) and poly(lactic acid)-co-(glycolic acid). Polymer International 2005; 54(1): 36-46; Kenley, R. A., Lee, M. O., Mahoney, T. R. and Sanders, L. M., Poly(lactide-co-glycolide) decomposition kinetics in vivo and in vitro. Macromolecules 1987; 20(10):2398-2403; Nelson, K. D., Romero, A. and Waggoner, P., et al., Technique paper for wet-spinning Poly(L-lactic acid) and poly(DL-lactide-co-glycolide) monofilament fibers. Tissue Engineering 2003; 9(6):1323-1330; Sihvola, P. and Puustjarvi, T., Practical problems in the use of Ocusert-pilocarpine delivery system. Acta Opthalmol Scand Suppl 1980; 58(6):933-7; Gao, H., Gu, Y. and Ping, Q., The implantable 5-fluorouracil-loaded poly(1-Lactic acid) fibers prepared by wet-spinning from suspension. Journal of Controlled Release 2007; 118 (3):325-332; Fujimoto, K., Yamamura, K., Hayashi, T., Osada, T. and Sakurai, T., Effect of Levofloxacin-Albumin Dacron Graft on Graft Infection. Jpn J Pharmacol 1995; 69(4):443-445; and Siepmann, J. and Gopferich, A., Mathematical modeling of bioerodible, polymeric drug delivery systems. Advanced Drug Delivery Reviews 2001; 48-(2-3): 229-247.

DOCTRINE OF EQUIVALENTS

Those skilled in the art will appreciate that the foregoing examples and descriptions of various preferred embodiments of the present invention are merely illustrative of the invention as a whole, and that variations in the relative composition of the various components of the present invention may be made within the spirit and scope of the invention. For example, it will be clear to one skilled in the art that other structures and additives may be included in the layered fibers discussed above that would not affect the improved properties of the layered fibers of the current invention nor render the alloys unsuitable for their intended purpose. Accordingly, the present invention is not limited to the specific embodiments described herein but, rather, is defined by the scope of the appended claims.

What is claimed is:

1. A layered polymeric drug delivery system comprising:
an elongated monofilament fiber body having a length and a cross-sectional profile, the cross-sectional profile having a perimeter;
wherein the elongated monofilament fiber body comprises a plurality of connected segments disposed along a longitudinal axis of the monofilament fiber body, each of said segments formed of at least two simultaneously coagulated and coextruded polymeric layers, the polymeric layers being formed from polymeric materials extrudable in one or more compatible non-solvents, wherein:
the at least two coextruded polymeric layers are bound by polymer fusion at their interface, said interface between the at least two polymeric layers extending in a direction along the longitudinal axis of the monofilament fiber body;
at least a portion of each of the at least two polymeric layers defines at least a portion of the perimeter of the monofilament fiber body;
at least one therapeutic agent is disposed or contained within at least one of the at least two polymeric layers of at least one segment, said at least one therapeutic agent having a release rate at which the therapeutic agent is released from the layered polymeric drug delivery system into a subject; and
each of the polymeric layers of the layered polymeric drug delivery system being defined by a dissolution rate at which the polymeric layer is dissolved, wherein the dissolution rate of a least one of the polymeric layers is slower that the release rate of all of the therapeutic agents such that the therapeutic agent delivery and structural integrity of the layered polymeric drug delivery system are distinct; and
wherein the monofilament fiber body further comprises a plurality of connected segments disposed along the longitudinal axis of the monofilament fiber body.

2. The layered polymeric drug delivery system described in claim 1, wherein the at least two polymeric layers are formed of the same polymer.

3. The layered polymeric drug delivery system described in claim 2, having at least two polymeric layers each having different therapeutic agents disposed thereon.

4. The layered polymeric drug delivery system described in claim 1, wherein the at least two polymeric layers are formed of at least two different polymers.

5. The layered polymeric drug delivery system described in claim 4, having at least two polymeric layers each having the same therapeutic agent disposed thereon.

6. The layered polymeric drug delivery system described in claim 1, wherein all of the polymeric layers are formed from biodegradable polymers.

7. The layered polymeric drug delivery system described in claim 6, wherein the biodegradable polymer is one or a combination of materials selected from the group consisting of, as well as poly(lactide-coglycolide) (PLGA), polyglycolic acid (PGA), and polylactic acid (PLA), polycaprolactone (PCL) and polydioxanone (PDO).

8. The layered polymeric drug delivery system described in claim 1, wherein at least one of the at least two polymeric layers is a non-biodegradable polymer.

9. The layered polymeric drug delivery system described in claim 8, wherein the non-biodegradable polymer is one or combination of materials selected from the group consisting of, poly(lactide-coglycolide) (PLGA), polyglycolic acid (PGA), polylactic acid (PLA), polycaprolactone (PCL), polydioxanone (PDO), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl acetates, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinylchloride-diethyl fumerate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitrile copolymer.

10. The layered polymeric drug delivery system described in claim 1, wherein the elongated fiber body includes a plurality of therapeutic agents disposed in a plurality of segments.

11. The layered polymeric drug delivery system described in claim 1, wherein at least two of the segments are comprised of different numbers of the polymeric layers.

12. The layered polymeric drug delivery system described in claim 1, wherein the polymeric layers of at least two of the segments are comprised of different polymers.

13. The layered polymeric drug delivery system described in claim 1, wherein the system gradually releases the therapeutic agent over a period of time after implantation in a patient.

14. The layered polymeric drug delivery system described in claim 1, wherein the system releases an initial surge of the therapeutic agent after implantation in a patient.

15. The layered polymeric drug delivery system described in claim 1, wherein the system releases a gradually increasing amount of the therapeutic agent over a period of time after implantation in a patient.

16. The layered polymeric drug delivery system described in claim 1, wherein the therapeutic agent is disposed within the polymeric layer in accordance with a method selected from the group consisting of dissolving, dispersing and suspending.

17. The layered polymeric drug delivery system described in claim 1, wherein the therapeutic agent is associated to the polymeric layer in accordance with a method selected from the group consisting of electrostatic interaction, hydrogen bonding, hydrophobic interaction, formation of inclusion complexes with the inclusion hosts, and covalent attachment to the polymer.

18. The layered polymeric drug delivery system described in claim 17, wherein the therapeutic agent is covalently linked to the polymer by one or more linking moieties, and wherein the one or more linking moieties are cleaved under physiological conditions.

19. The layered polymeric drug delivery system described in claim 1, wherein at least the polymeric layer incorporating the therapeutic agent further comprises an additive selected from the group consisting of plasticizers, polymers, and cyclodextrins.

20. The layered polymeric drug delivery system described in claim 18, wherein the polymeric layer includes a cyclodextrin additive and the therapeutic agent forms an inclusion complex with the cyclodextrin.

21. The layered polymeric drug delivery system described in claim 20, wherein the cyclodextrin is attached to the polymer in accordance with a method selected from the group consisting of covalent linking, incorporation in the backbone of the polymer, and incorporation into a side chain of the polymer.

22. The layered polymeric drug delivery system described in claim 20, wherein the cyclodextrin is a modified cyclodextrin selected from the group consisting of benzylated, acylated, alkylated, methylated, hydroxypropylated and sulfobutyletherated.

23. The layered polymeric drug delivery system described in claim 19, wherein the additive is selected from the group consisting of sugars, salts, poly(ethylene oxide), poly(ethylene glycol), benzyl benzoate, acetyl tributyl-citrate, triethyl-citrate, trihexyl-citrate, and dibutyl sebacate.

24. The layered polymeric drug delivery system described in claim 19, wherein the at least one of the therapeutic agents is water soluble, and wherein the additive is a hydrophobic plasticizer, which is disposed on the polymeric layer containing said at least one therapeutic agent such that the therapeutic agent and the hydrophobic plasticizer form a hydrophobic ion pair.

25. The layered polymeric drug delivery system described in claim 24, wherein the hydrophobic plasticizer is selected from the group consisting of octanoic acid, decanoic acid, hexanoic acid, long chain organic acids, and salts thereof, octylamine, decylamine, long chain amines carboxylic acid and amine functionalized adamantine.

26. The layered polymeric drug delivery system described in claim 1, further comprising a hydrophobic plasticizer disposed on at least one of the polymeric layers, wherein the plasticizer is non-interacting with the therapeutic agent.

27. The layered polymeric drug delivery system described in claim 26, wherein the hydrophobic plasticizer is selected from the group consisting of benzyl benzoate, acetyl tributyl-citrate, triethyl-citrate, trihexyl-citrate, and dibutyl sebacate.

28. The layered polymeric drug delivery system described in claim 1, wherein the at least one therapeutic agent is one or a combination of substances selected from the group consisting of a nucleic acid, a protein, a peptide, and a small molecule.

29. The layered polymeric drug delivery system described in claim 28, wherein the therapeutic agent is selected from the group consisting of a steroid, a corticosteroid, retinoid, a NSAID, a vitamin D3 analog, a human carbonic anhydrase inhibitor, a neurotrophic factor, an anti-cancer agent, an antibiotic agent, an anti-inflammatory agent, an immunosuppressant, an antiviral agent, an anti-proliferative agent, an antimicrobial agent, a nerve growth inducing agent, or a combination thereof.

30. The layered polymeric drug delivery system described in claim 1, wherein the therapeutic agent is present at a substantially uniform concentration throughout the width of one or more polymeric layers of the fiber.

31. The layered polymeric drug delivery system described in claim 1, further comprising one or more adjuvants.

32. The layered polymeric drug delivery system described in claim 1, further comprising one or more coatings.

33. The layered polymeric drug delivery system described in claim 32, wherein the coating comprises one or more therapeutic agents or adjuvants.

34. The layered polymeric drug delivery system described in claim 1, wherein the fiber takes a form selected from the group consisting of a ribbon, a tube, and a lumen.

35. The layered polymeric drug delivery system described in claim 1, wherein the fiber comprises one or more bulbs along the length of the fiber.

36. The layered polymeric drug delivery system described in claim 35, wherein at least one bulb comprises one or more therapeutic agents.

37. A thread comprising a plurality of fibers as set forth in claim 1.

38. The thread of claim 37, wherein the thread takes a form selected from the group consisting of a monofilament and a polyfilament.

39. The thread of claim 37, wherein the individual fibers of the thread are braided.

40. The thread of claim 37, further comprising at least one additional conventional fiber selected from the group consisting of, poly(lactide-coglycolide) (PLGA), polyglycolic acid (PGA), polylactic acid (PLA), polycaprolactone (PCL), polydioxanone (PDO), Nylon, silk, linen, catgut, and stainless steel.

41. The thread of claim 37, further comprising one or more layers or plies.

42. A suture comprising one or more of the threads of claim 37.

43. A fabric comprising one or more of the threads of claim 37.

* * * * *